US007927870B2

(12) United States Patent
Volkin et al.

(10) Patent No.: US 7,927,870 B2
(45) Date of Patent: Apr. 19, 2011

(54) DNA VACCINE FORMULATIONS

(75) Inventors: David B. Volkin, Doylestown, PA (US);
Robert K. Evans, Soudertown, PA (US);
Mark Bruner, Norristown, PA (US)

(73) Assignee: Merck Sharp & Dohme Corp.,
Rahway, NJ (US)

( * ) Notice: Subject to any disclaimer, the term of this patent is extended or adjusted under 35 U.S.C. 154(b) by 136 days.

(21) Appl. No.: 11/431,676

(22) Filed: May 10, 2006

(65) Prior Publication Data

US 2006/0217341 A1    Sep. 28, 2006

Related U.S. Application Data

(63) Continuation of application No. 10/697,233, filed on Oct. 30, 2003, now abandoned, which is a continuation of application No. 09/948,337, filed on Sep. 7, 2001, now abandoned, which is a continuation of application No. 09/414,671, filed on Oct. 7, 1999, now abandoned, which is a continuation of application No. 08/844,525, filed on Apr. 18, 1997, now abandoned.

(60) Provisional application No. 60/017,049, filed on Apr. 26, 1996.

(51) Int. Cl.
*C12N 15/00* (2006.01)
*C07H 21/04* (2006.01)

(52) U.S. Cl. .................................. 435/320.1; 536/23.1

(58) Field of Classification Search ........................ None
See application file for complete search history.

(56) References Cited

U.S. PATENT DOCUMENTS

| | | | |
|---|---|---|---|
| 3,915,794 A | 10/1975 | Zygraich et al. | |
| 5,057,426 A | 10/1991 | Henco et al. | |
| 5,096,823 A * | 3/1992 | Gloeckler et al. | ....... 435/252.31 |
| 5,521,061 A | 5/1996 | Bresser et al. | |
| 5,561,064 A | 10/1996 | Marquet et al. | |
| 5,672,593 A * | 9/1997 | Michejda et al. | ............ 514/151 |
| 5,736,524 A | 4/1998 | Content et al. | |
| 5,811,406 A | 9/1998 | Szoka et al. | |
| 5,830,659 A * | 11/1998 | Stewart | .............................. 435/6 |
| 5,851,769 A | 12/1998 | Gray et al. | |
| 5,869,306 A | 2/1999 | Kuma et al. | |
| 5,985,327 A | 11/1999 | Burgoyne | |
| 6,004,777 A | 12/1999 | Tartaglia et al. | |
| 6,022,737 A * | 2/2000 | Niven et al. | ................ 435/320.1 |
| 7,078,511 B1 * | 7/2006 | Krieger et al. | ............... 536/23.5 |

FOREIGN PATENT DOCUMENTS

| | | |
|---|---|---|
| WO | WO93/03167 | 2/1993 |
| WO | WO94/02639 | 2/1994 |
| WO | WO96/20732 | 7/1996 |
| WO | WO96/39813 | 12/1996 |
| WO | WO96/40265 | 12/1996 |
| WO | WO96/41873 | 12/1996 |

OTHER PUBLICATIONS

Takehara et al., Physiol. Chem. Phys. & Med. NMR (1994) 26:215-226.*
Haynes et al "Gene Gun Medicated DNA Immunization Elicits Humoral, Cytotoxic and Protective Immune Response" Vaccines 1994, pp. 65-70.
Lindahl et al. "Rate of Depurination of Native Deoxyribonucleic Acid", Biochemistry, vol. 11, No. 19, 1972.
Lindahl et al. "Rage of Chain Breakage at Apurinic Sites in Double-Stranded Deoyribonucleic Acid", Biochemistry, vol. 11, No. 19, 1972.
Graf et al. "Iron-catalyzed Hydroxyl Radical Formation", The Journal of Biological Chemistry, vol. 259, No. 6, Issue of Mar. 25, pp. 3620-3624, 1984.
Greer at al. "Studies on Depurination of DNA by Heat", J. Mol. Biol. (1962), 4, 123-141.
Freitas et al "Pentoxifyline—A Hydroyl Radical Scavenger" Biol. Trace Elern. Trs. 47: p. 307-311.
Hu et al. "Para-aminobenzoic acid scavenges reactive oxygen species and protects DNA against UV and free radical damage", J. Nuts. Biochem. 6: p. 504-508.
Zinkernagel et al. "Antiviral Immunity", Immunology Today, vol. 18(6), pp. 258-260 (1997).
Robinson, "Nucleic acid vaccines: an overview"; Vaccine, vol. 15 (8), pp. 785-787, (1997).
Strugnell et al. "DNA vaccines for bacterial infections", Immunol. Cell Biol. vol. 75, pp. 364-369.
Chattergoon at al. "Genetic immunization: a new era in vaccines and immune therapeutics", FASEB J., vol. 11, pp. 753-763 (1997).
Lang, "Tertiary Structure of Purified DNA by Dehydration with Ethanol"; Tex. Rep. Biol. Med., vol. 31(2), p. 258 (1973).
Peak et al. "Similar Ultraviolet Action Spectra for the Protection by Glycerol of Transforming DNA against Single-StranD Breaks and Inactivation of Biological Activity"; Rad. Res. vol. 97, pp. 570-575 (1984).
Goodman et al. "Cloning of Hormone Genes from a Mixture of cDNA Molecules", Methods in Enzymology, vol. 68, pp. 75-90, (1979).
Sigma Catalogue, pp. 485 and 1556 (1993).
Gennaro, Remington: Practice of; 19th Edition, (1995).
Gibco BRL, Life Technologies Catalogue, (1994).
Graves et al. Pharmaceutical Research, vol. 11 (10), Suppl. S1-S490 (1994).
Sarker et al. "Oxygen radical-induced single strand DNA ... system" Mutations Res. vol. 337, pp. 85-95 (1995).
Maniatis et al., 1982, Cold Spring Harbor Laboratory, Molecular Cloning, A Laboratory Manual, "Purification of Closed Circular DNA by Centrifugation to Equilibrium in Cesium Chloride-Ethidium Bromide Gradients", pp. 93-94.
Ulmer et al., 1993, "Heterologous Protection Against Influenza by Injection of DNA Encoding a Viral Protein", Sceince, 259: 1745-1949.
Kondo et al., 1991, "Rapid Isolation of Plasmid DNA by LiCl-Ethidium Bromide Treatment and Gel Filtration", Analytical Biochemistry 198: 30-35.

* cited by examiner

*Primary Examiner* — Nancy Vogel
(74) *Attorney, Agent, or Firm* — Henry P. Wu; Sheldon O. Heber

(57) ABSTRACT

This invention relates to novel methods and formulations of nucleic acid pharmaceutical products, specifically formulations of nucleic acid vaccine products and nucleic acid gene therapy products. The formulations of the disclosure stabilize the conformation of DNA pharmaceutical products.

14 Claims, 35 Drawing Sheets

1. PBS control
2. PBS + 200 μM EDTA
3. PBS + 200 μM IHP
4. PBS + 200 μM DTPA
5. PBS + 200 μM NTA
6. PBS + 200 μM IDA

DNA VACCINE FORMULATIONS

This application is a continuation of U.S. application Ser. No. 10/697,233, filed Oct. 30, 2003, now abandoned which is a continuation of U.S. application Ser. No. 09/948,337, filed Sep. 7, 2001, now abandoned, which is continuation of U.S. application Ser. No. 09/414,671, filed Oct. 7, 1999, now abandoned, which is a continuation of U.S. application Ser. No. 08/844,525, filed Apr. 18, 1997, now abandoned, which claims benefit under 35 U.S.C. §119(e) to U.S. provisional application Ser. No. 60/017,049, filed Apr. 26, 1996.

STATEMENT REGARDING FEDERALLY-SPONSORED R&D

Not Applicable

REFERENCE TO MICROFICHE APPENDIX

Not Applicable

FIELD OF THE INVENTION

The present invention relates to novel formulations of nucleic acid pharmaceutical products, specifically formulations of nucleic acid vaccine products and nucleic acid gene therapy products. The formulations of the disclosure stabilize the conformation of DNA pharmaceutical products. The vaccines, when introduced directly into muscle cells, induce the production of immune responses which specifically recognize human influenza virus.

BACKGROUND OF THE DISCLOSURE

This invention relates to novel formulations of nucleic acid pharmaceutical products, specifically formulations of nucleic acid vaccine products and nucleic acid gene therapy products. The formulations of the disclosure stabilize the conformation of DNA pharmaceutical products. The vaccines, when introduced directly into muscle cells, induce the production of immune responses which specifically recognize human influenza virus.

During storage as a pharmaceutical entity, DNA plasmid vaccines undergo a physicochemical change in which the supercoiled plasmid converts to the open circular and linear form. A variety of storage conditions (low pH, high temperature, low ionic strength) can accelerate this process. In this invention, the removal and/or chelation of trace metal ions (with succinic or malic acid, or with chelators containing multiple phosphate ligands) from the DNA plasmid solution, from the formulation buffers or from the vials and closures, stabilizes the DNA plasmid from this degradation pathway during storage. In addition, non-reducing free radical scavengers are required to prevent damage of the DNA plasmid from free radical production that may still occur, even in apparently demetalated solutions. Furthermore, the buffer type, pH, salt concentration, light exposure, as well as the type of sterilization process used to prepare the vials, all must be controlled in the formulation to optimize the stability of the DNA vaccine. Lyophilization of the DNA vaccine in the presence of the appropriate formulation excipients can also be performed to stabilize the plasmid during storage.

From the scientific literature, the chain scission reaction causing conversion of supercoiled to open circular to linear DNA plasmid would be expected to occur via two different chemical mechanisms (since these preparations of highly purified DNA do not contain nucleases): (1) depurination followed by β-elimination and/or (2) free radical oxidation. Although removal of trace metal ions would be expected to suppress the free radical oxidation mechanism of DNA chain scission, surprisingly, our results indicate that the removal or chelation of trace metal ions from the DNA containing solution, stabilizes the DNA against both mechanisms of degradation, as judged by comparison of our stability data with the published rates of depurination and β-elimination (see Lindahl et al., 1972, *Biochemistry* 19: 3610-3618; Lindahl et al., 1972, *Biochemistry* 19: 3618-3623). Based on these and other published reports, the removal of trace metal ions would not be expected to have a significant effect on the rates of depurination or β-elimination. Therefore, the increase in DNA stability resulting from the removal of trace metal ions is much larger than expected, and cannot be explained on the basis of the published rate constants for depurination and β-elimination.

In addition, our data indicates that specific chelating agents such as inositol hexaphosphate, tripolyphosphate, succinic and malic is acid, increase the stability of plasmid DNA in storage, while other commonly used chelating agents such as EDTA, desferal, ethylenediamine-Di(o-hydoxy-phenylacetic acid (EDDHA) and diethylenetriaminepenta-acetic acid (DTPA) provide no significant enhancement of stability. These results also suggest that any chelating agent with multiple phosphate ligands (for example, polyphosphoric acid) will enhance DNA stability. It is not clear from the published literature, however, why inositol hexaphosphate stabilizes DNA, but EDDHA, desferal and DTPA do not. Since the published literature suggests that all four of these chelators inhibit the production of hydroxyl radicals catalyzed by iron, it was expected that all of these reagents would provide enhanced DNA stability (by chelating trace metal ions and inhibiting the production of free radicals), but this was not observed. Moreover, the literature reports that both EDTA and ATP support metal ion catalyzed hydroxyl radical production, but we have observed that tripolyphosphate (the metal binding moiety of ATP) enhances DNA stability while EDTA does not. Therefore, the protective effects of the metal ion chelators do not appear to be directly correlated with their ability to support the production of hydroxyl radicals. The identification of the appropriate chelators to stabilize DNA formulations will require empirical testing as described in this work.

In addition to the removal and/or chelation of trace metal ions, the use of non-reducing free radical scavengers is important for stabilizing DNA formulations during storage. Our results indicate that ethanol, methionine, glycerol and dimethyl sulfoxide enhance DNA stability, suggesting that their protective effect is due to the scavenging of free radicals. Furthermore, our results indicate that scavengers capable of serving as reducing agents, such as ascorbic acid, greatly accelerate DNA degradation, presumably by acting as a reducing agent to keep trace metal ions in their reduced (most damaging) state. Our results also indicate that several scavengers expected to stabilize DNA (based on known rate constants with hydroxyl radical) unexpectedly accelerated DNA degradation, or provided no increase in stability. For example, pentoxifylline and para-aminobenzoic acid are hydroxyl radical scavengers with large rate constants for hydroxyl radicals ($k=1.1\times10^{10}\ M^{-1}\ s^{-1}$; see Freitas and Filipe, 1995, *Biol. Trace Elem. Res.* 47: 307-311; Hu et al., 1995, *J. Nutr. Biochem.* 6: 504-508), yet pentoxifylline did not enhance stability and p-aminobenzoic acid actually accelerated DNA degradation. Because of these results, the empirical screening of a number of free radical scavengers has been the most effective means of identifying useful compounds.

To maximize DNA stability in a pharmaceutical formulation, the type of buffer, salt concentration, pH, light exposure as well as the type of sterilization process used to prepare the vials are all important parameters that must be controlled in the formulation to further optimize the stability. Furthermore, lyophilization of the DNA vaccine with appropriate formulation excipients can also be performed enhance DNA stability, presumably by reducing molecular motion via dehydration. Therefore, our data suggest that the formulation that will provide the highest stability of the DNA vaccine will be one that includes a demetalated solution containing a buffer (phosphate or bicarbonate) with a pH in the range of 7-8, a salt NaCl, KCl or LiCl) in the range of 100-200 mM, a metal ion chelator (succinate, malate, inositol hexaphosphate, tripolyphosphate or polyphosphoric acid), a non-reducing free radical scavenger (ethanol, glycerol, methionine or dimethyl sulfoxide) and the highest appropriate DNA concentration in a sterile glass vial, packaged to protect the highly purified, nuclease free DNA from light.

The instant formulations and methods are exemplified with a DNA vaccine against influenza. Nothing in this disclosure should be construed as limiting the formulations and methods to the specific DNA vaccine.

Influenza is an acute febrile illness caused by infection of the respiratory tract with influenza A or B virus. Outbreaks of influenza occur worldwide nearly every year with periodic epidemics or pandemics. Influenza can cause significant systemic symptoms, severe illness (such as viral pneumonia) requiring hospitalization, and complications such as secondary bacterial pneumonia. Recent U.S. epidemics are thought to have resulted in >10,000 (up to 40,000) excess deaths per year and 5,000-10,000 deaths per year in non-epidemic years. The best strategy for prevention of the morbidity and mortality associated with influenza is vaccination. The current licensed vaccines are derived from virus grown in eggs, then inactivated, and include three virus strains (two A strains and one B strain). Three types of vaccines are available: whole-virus, subvirion, and purified surface antigen. Only the latter two are used in children because of increased febrile responses with the whole-virus vaccine. Children under the age of 9 require two immunizations, while adults require only a single injection. However, it has been suggested [see *Medical Letter* 32:89-90, Sep. 17, 1993] that "patients vaccinated early in the autumn might benefit from a second dose in the winter or early spring," due to the observations that in some elderly patients, the antibody titers following vaccination may decline to less-than-protective levels within four months or less. These vaccines are reformulated every year by predicting which recent viral strains will clinically circulate and evaluating which new virulent strain is expected to be predominant in the coming flu season. Revaccination is recommended annually.

The limitations of the licensed vaccine include the following:

1) Antigenic variation, particularly in A strains of influenza, results in viruses that are not neutralized by antibodies generated by a previous vaccine (or previous infection). New strains arise by point mutations (antigenic drift) and by reassortment (antigenic shift) of the genes encoding the surface glycoproteins (hemagglutinin [HA] and neuraminidase), while the internal proteins are highly conserved among drifted and shifted strains. Immunization elicits "homologous" strain-specific antibody-mediated immunity, not "heterologous" group-common immunity based on cell-mediated immunity.

2) Even if the predominant, circulating strains of influenza virus do not shift or drift significantly from one year to the next, immunization must be given each year because antibody titers decline. Although hemagglutination-inhibiting (HI) and neutralizing antibodies are reported by some to persist for months to years with a subsequent gradual decline, the Advisory Committee on Immunization Practices cites the decline in antibody titers in the year following vaccination as a reason for annual immunization even when there has been no major drift or shift. (HI antibodies inhibit the ability of influenza virus to agglutinate red blood cells. Like neutralizing antibodies, they are primarily directed against the HA antigen. Hemagglutination inhibition tests are easier and less expensive to perform than neutralization assays are, and thus are often used as a means to assess the ability of antibodies raised against one strains of influenza to react to a different strain). As mentioned above, The *Medical Letter* suggests that certain high-risk, older individuals should be vaccinated twice in one season due to short-lived protective antibody titers.

3) The effectiveness of the vaccine is suboptimal. Development of the next season's vaccine relies upon predicting the upcoming circulating strains (via sentinel sampling in Asia), which is inexact and can result in a poor match between strains used for the vaccine and those that actually circulate in the field. Moreover, as occurred during the 1992-1993 flu season, a new H3N2 strain (A/Beijing/92) became clinically apparent during the latter phase of the flu season. This prompted a change in the composition of the 1993-1994 vaccine, due to poor cross-reactivity with A/Beijing/92 of the antibody induced by the earlier H3N2 strain (A/Beijing/89) due to antigenic shift. However, due to the length of time needed to make and formulate the current licensed vaccine, the new vaccine strain could not be introduced during the 1992-1993 season despite the evidence for poor protection from the existing vaccine and the increased virulence of the new circulating H3N2 strain.

Characteristics of an Ideal Universal Influenza Vaccine include the following:

1) Generation of group-common (heterologous) protection.

2) Increased breadth of antibody response. Because CTL are thought to play a role in recovery from disease, a vaccine based solely upon a CTL response would be expected to shorten the duration of illness (potentially to the point of rendering illness subclinical), but it would not prevent illness completely.

3) Increased duration of antibody responses. Because one of the very groups that is at highest risk for the morbidity and mortality of influenza infection (elderly) is also the group in whom protective antibody titers may decline too rapidly for annual immunization to be effective, an improved vaccine should generate protective titers of antibody that persist longer.

Intramuscular inoculation of polynucleotide constructs, i.e., DNA plasmids encoding proteins have been shown to result in the in situ generation of the protein in muscle cells. By using cDNA plasmids encoding viral proteins, both antibody and CTL responses were generated, providing homologous and heterologous protection against subsequent challenge with either the homologous or cross-strain protection, respectively. Each of these types of immune responses offers a potential advantage over existing vaccination strategies. The use of PNVs (polynucletide vaccines) to generate antibodies may result in an increased duration of the antibody responses as well as the provision of an antigen that can have both the exact sequence of the clinically circulating strain of virus as well as the proper post-translational modifications and conformation of the native protein (vs. a recombinant protein). The generation of CTL responses by this means offers the benefits of cross-strain protection without the use of a live potentially pathogenic vector or attenuated virus.

Therefore, this invention contemplates any of the known methods for introducing nucleic acids into living tissue to induce expression of proteins. This invention provides a method for introducing viral proteins into the antigen processing pathway to generate virus-specific CTLs. Thus, the need for specific therapeutic agents capable of eliciting desired prophylactic immune responses against viral pathogens is met for influenza virus by this invention. Of particular importance in this therapeutic approach is the ability to induce T-cell immune responses which can prevent infections even of virus strains which are heterologous to the strain from which the antigen gene was obtained. Therefore, this invention provides DNA constructs encoding viral proteins of the human influenza virus nucleoprotein (NP), hemagglutinin (HA), neuraminidase (NM), matrix (M), nonstructural (NS), polymerase (PB1 and PB2=basic polymerases 1 and 2; PA=acidic polymerase) or any of the other influenza genes which encode products which generate specific CTLs.

SUMMARY OF THE INVENTION

This invention relates to novel formulations of nucleic acid pharmaceutical products, specifically formulations of nucleic acid vaccine products and nucleic acid gene therapy products. The formulations of the disclosure stabilize the conformation of DNA pharmaceutical products. The vaccines, when introduced directly into muscle cells, induce the production of immune responses which specifically recognize human influenza virus.

During storage as a pharmaceutical entity, DNA plasmid vaccines undergo a physicochemical change in which the supercoiled plasmid converts to the open circular and linear form. A variety of storage conditions (low pH, high temperature, low ionic strength) can accelerate this process. In this invention, the removal and/or chelation of trace metal ions (with succinic or malic acid, or with chelators containing multiple phosphate ligands) from the DNA plasmid solution, from the formulation buffers or from the vials and closures, stabilizes the DNA plasmid from this degradation pathway during storage. In addition, non-reducing free radical scavengers are required to prevent damage of the DNA plasmid from free radical production that may still occur, even in apparently demetalated solutions. Furthermore, the buffer type, pH, salt concentration, light exposure, as well as the type of sterilization process used to prepare the vials, all must be controlled in the formulation to optimize the stability of the DNA vaccine. Lyophilization of the DNA vaccine in the presence of the appropriate formulation excipients can also be performed to stabilize the plasmid during storage.

From the scientific literature, the chain scission reaction causing conversion of supercoiled to open circular to linear DNA plasmid would be expected to occur via two different chemical mechanisms (since these preparations of highly purified DNA do not contain nucleases): (1) depurination followed by β-elimination and/or (2) free radical oxidation. Although removal of trace metal ions would be expected to suppress the free radical oxidation mechanism of DNA chain scission, surprisingly, our results indicate that the removal or chelation of trace metal ions from the DNA containing solution, stabilizes the DNA against both mechanisms of degradation, as judged by comparison of our stability data with the published rates of depurination and β-elimination (see Lindahl et al., 1972, *Biochemistry* 19: 3610-3618; Lindahl et al., 1972, *Biochemistry* 19: 3619-3623). Based on these and other published reports, the removal of trace metal ions would not be expected to have a significant effect on the rates of depurination or β-elimination. Therefore, the increase in DNA stability resulting from the removal of trace metal ions is much larger than expected, and cannot be explained on the basis of the published rate constants for depurination and β-elimination.

In addition, our data indicates that specific chelating agents such as inositol hexaphosphate, tripolyphosphate, succinic and malic acid, increase the stability of plasmid DNA in storage, while other commonly used chelating agents such as EDTA, desferal, ethylenediamine-Di(o-hydoxy-phenylacetic acid (EDDHA) and diethylenetriaminepenta-acetic acid (DTPA) provide no significant enhancement of stability. These results also suggest that any chelating agent with multiple phosphate ligands (for example, polyphosphoric acid) will enhance DNA stability. It is not clear from the published literature, however, why inositol hexaphosphate stabilizes DNA, but EDDHA, desferal and DTPA do not. Since the published literature suggests that all four of these chelators inhibit the production of hydroxyl radicals catalyzed by iron, it was expected that all of these reagents would provide enhanced DNA stability (by chelating trace metal ions and inhibiting the production of free radicals), but this was not observed. Moreover, the literature reports that both EDTA and ATP support metal ion catalyzed hydroxyl radical production, but we have observed that tripolyphosphate (the metal binding moiety of ATP) enhances DNA stability while EDTA does not. Therefore, the protective effects of the metal ion chelators do not appear to be directly correlated with their ability to support the production of hydroxyl radicals. The identification of the appropriate chelators to stabilize DNA formulations will require empirical testing as described in this work.

In addition to the removal and/or chelation of trace metal ions, the use of non-reducing free radical scavengers is important for stabilizing DNA formulations during storage. Our results indicate that ethanol, methionine, glycerol and dimethyl sulfoxide enhance DNA stability, suggesting that their protective effect is due to the scavenging of free radicals. Furthermore, our results indicate that scavengers capable of serving as reducing agents, such as ascorbic acid, greatly accelerate DNA degradation, presumably by acting as a reducing agent to keep trace metal ions in their reduced (most damaging) state. Our results also indicate that several scavengers expected to stabilize DNA (based on known rate constants with hydroxyl radical) unexpectedly accelerated DNA degradation, or provided no increase in stability. For example, pentoxifylline and para-aminobenzoic acid are hydroxyl radical scavengers with large rate constants for hydroxyl radicals ($k=1.1 \times 10^{10}$ $M^{-1}$ $s^{-1}$; see Freitas and Filipe, 1995, *Biol. Trace Elem. Res.* 47: 307-311; Hu et al., 1995, *J. Nutr. Biochem.* 6: 504-508), yet pentoxifylline did not enhance stability and p-aminobenzoic acid actually accelerated DNA degradation. Because of these results, the empirical screening of a number of free radical scavengers has been the most effective means of identifying useful compounds.

To maximize DNA stability in a pharmaceutical formulation, the type of buffer, salt concentration, pH, light exposure as well as the type of sterilization process used to prepare the vials are all important parameters that must be controlled in the formulation to further optimize the stability. Furthermore, lyophilization of the DNA vaccine with appropriate formulation excipients can also be performed enhance DNA stability, presumably by reducing molecular motion via dehydration. Therefore, our data suggest that the formulation that will provide the highest stability of the DNA vaccine will be one that includes a demetalated solution containing a buffer (phosphate or bicarbonate) with a pH in the range of 7-8, a salt (NaCl, KCl or LiCl) in the range of 100-200 mM, a metal ion chelator (succinate, malate, inositol hexaphosphate, tripolyphosphate or polyphosphoric acid), a non-reducing free radical scavenger (ethanol, glycerol, methionine or dimethyl sulfoxide) and the highest appropriate DNA concentration in a sterile glass vial, packaged to protect the highly purified, nuclease free DNA from light.

Data is presented in this specification which exemplifies several additional DNA vaccine formulations. More specifically, the present invention relates to DNA vaccine formulations which comprise a demetalated solution containing a physiologically acceptable buffer within a pH range from at least greater than about 8.0 to about at least 9.5, a salt (including but not limited to NaCl, KCl or LiCl) in the range of up to about at 300 mM, and the metal ion chelator EDTA (in the range of up to about 5 mM) in combination with the free radical scavenger ethanol (in the range of up to about 3%) and the highest appropriate DNA concentration in a sterile glass vial, packaged to protect the highly purified, nuclease free DNA from light and in a physiologically acceptable buffer.

In a specific aspect of the present invention, the DNA vaccine formulations comprise a combination of EDTA and ethanol, NaCl at a concentration from about 100 mM to about 200 mM, EDTA in the range from about 1 µM to about 1 mM, ethanol present up to about 2%, all in the highest appropriate DNA concentration in a sterile glass vial, packaged to protect the highly purified, nuclease free DNA from light and in a physiologically acceptable buffer.

In another embodiment of the DNA vaccine formulations comprising a combination of EDTA and ethanol, NaCl is present from about 100 mM to about 200 mM, EDTA is present from about 1 µM to about 750 µM, ethanol is present from about 0.5% to about 2.5%, all in the highest appropriate DNA concentration in a sterile glass vial, packaged to protect the highly purified, nuclease free DNA from light and in a physiologically acceptable buffer which preferably is Tris-HCl at a pH from about 8.0 to about 9.0 and glycine from about pH 9.0 to about pH 9.5. It will be understood that other known buffers with a buffering capacity within various pH ranges, such as pH 8.0 to 9.5, may be utilized in the various DNA vaccine formulations of the present invention.

In an especially preferred aspect of the present invention wherein the DNA vaccine formulations comprise a combination of EDTA and ethanol, NaCl at a concentration from about 100 mM to about 200 mM, EDTA is present at about 500 µM, ethanol is present at about 1.0%, all in the highest appropriate DNA concentration in a sterile glass vial, packaged to protect the highly purified, nuclease free DNA from light and in a physiologically acceptable buffer which preferably is Tris-HCl at a pH from about 8.5 to about 9.0.

DETAILED DESCRIPTION OF THE INVENTION

Figure 1A:
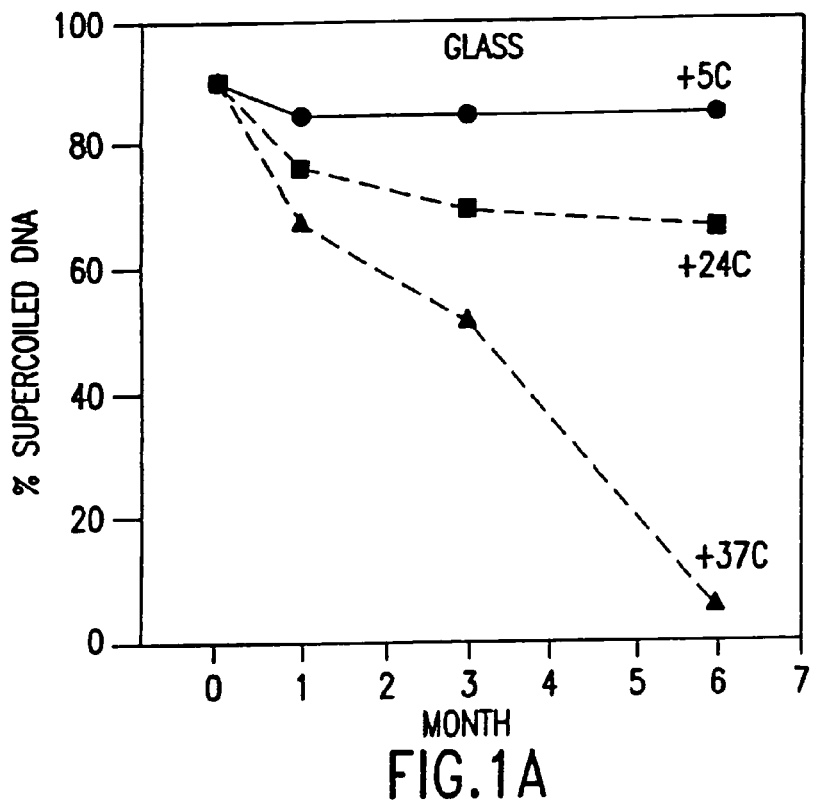
FIG. 1A, FIG. 1B, FIG. 1C and FIG. 1D show the effect of container type on supercoil content of Influenza DNA vaccine, HA (Georgia/93) during storage. DNA plasmid solution was prepared at 100 mcg/mL DNA in saline. Supercoil content of plasmid was determined by agarose gel electrophoresis. Panel A—glass; Panel B—siliconized glass; Panel C—autoclaved plastic; Panel D—gamma-plastic.
Figure 1B:
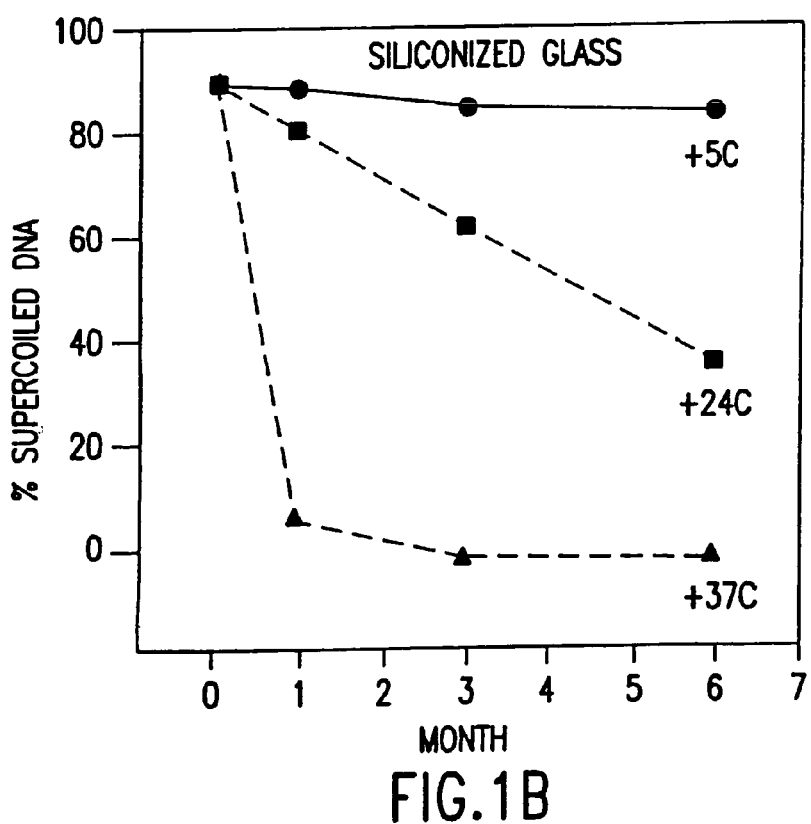
Figure 1C:
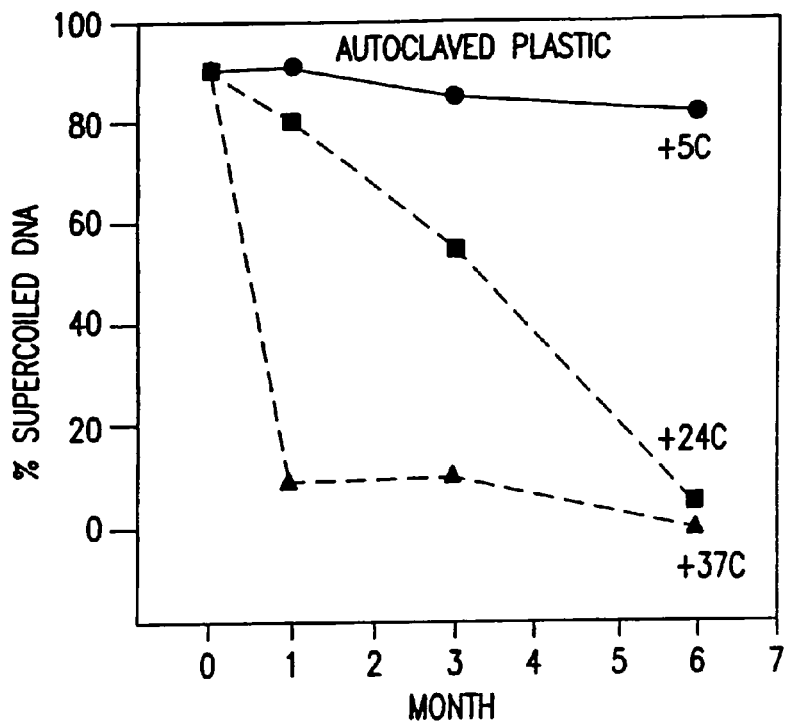
Figure 1D:
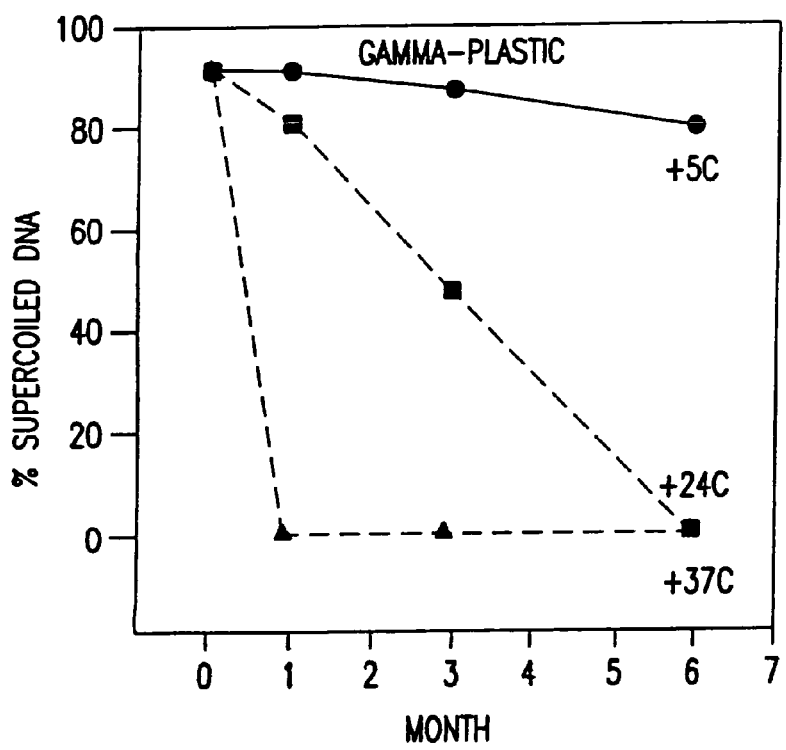

This invention relates to novel formulations of nucleic acid pharmaceutical products, specifically formulations of nucleic acid vaccine products and nucleic acid gene therapy products. The formulations of the disclosure stabilize the conformation of DNA pharmaceutical products. The vaccines, when introduced directly into muscle cells, induce the production of immune responses which specifically recognize human influenza virus.

During storage as a pharmaceutical entity, DNA plasmid vaccines undergo a physicochemical change in which the supercoiled plasmid converts to the open circular and linear form. A variety of storage conditions (low pH, high temperature, low ionic strength) can accelerate this process. In this invention, the removal and/or chelation of trace metal ions (with succinic or malic acid, or with chelators containing multiple phosphate ligands) from the DNA plasmid solution, from the formulation buffers or from the vials and closures, stabilizes the DNA plasmid from this degradation pathway during storage. In addition, non-reducing free radical scavengers are required to prevent damage of the DNA plasmid from free radical production that may still occur, even in apparently demetalated solutions. Furthermore, the buffer type, pH, salt concentration, light exposure, as well as the type of sterilization process used to prepare the vials, all must be controlled in the formulation to optimize the stability of the DNA vaccine. Lyophilization of the DNA vaccine in the presence of the appropriate formulation excipients can also be performed to stabilize the plasmid during storage.

From the scientific literature, the chain scission reaction causing conversion of supercoiled to open circular to linear DNA plasmid would be expected to occur via two different chemical mechanisms (since these preparations of highly purified DNA do not contain nucleases): (1) depurination followed by β-elimination and/or (2) free radical oxidation. Although removal of trace metal ions would be expected to suppress the free radical oxidation mechanism of DNA chain scission, surprisingly, our results indicate that the removal or chelation of trace metal ions from the DNA containing solution, stabilizes the DNA against both mechanisms of degradation, as judged by comparison of our stability data with the published rates of depurination and β-elimination (see Lindahl et al., *Biochemistry* 19: 3610-3618, 1972; Lindahl et al., *Biochemistry* 19: 3618-3623, 1972). Based on these and other published reports, the removal of trace metal ions would not be expected to have a significant effect on the rates of depurination or β-elimination. Therefore, the increase in DNA stability resulting from the removal of trace metal ions is much larger than expected, and cannot be explained on the basis of the published rate constants for depurination and β-elimination.

In addition, our data indicates that specific chelating agents such as inositol hexaphosphate, tripolyphosphate, succinic and malic acid, increase the stability of plasmid DNA in storage, while other commonly used chelating agents such as EDTA, desferal, ethylenediamine-Di(o-hydoxy-phenylacetic acid (EDDHA) and diethylenetriaminepenta-acetic acid (DTPA) provide no significant enhancement of stability. These results also suggest that any chelating agent with multiple phosphate ligands (for example, polyphosphoric acid) will enhance DNA stability. It is not clear from the published literature, however, why inositol hexaphosphate stabilizes DNA, but EDDHA, desferal and DTPA do not. Since the published literature suggests that all four of these chelators inhibit the production of hydroxyl radicals catalyzed by iron, it was expected that all of these reagents would provide enhanced DNA stability (by chelating trace metal ions and inhibiting the production of free radicals), but this was not observed. Moreover, the literature reports that both EDTA and ATP support metal ion catalyzed hydroxyl radical production, but we have observed that tripolyphosphate (the metal binding moiety of ATP) enhances DNA stability while EDTA does not. Therefore, the protective effects of the metal ion chelators do not appear to be directly correlated with their ability to support the production of hydroxyl radicals. The identification of the appropriate chelators to stabilize DNA formulations will require empirical testing as described in this work.

In addition to the removal and/or chelation of trace metal ions, the use of non-reducing free radical scavengers is important for stabilizing DNA formulations during storage. Our results indicate that ethanol, methionine, glycerol and dimethyl sulfoxide enhance DNA stability, suggesting that their protective effect is due to the scavenging of free radicals. Furthermore, our results indicate that scavengers capable of serving as reducing agents, such as ascorbic acid, greatly accelerate DNA degradation, presumably by acting as a reducing agent to keep trace metal ions in their reduced (most damaging) state. Our results also indicate that several scavengers expected to stabilize DNA (based on known rate constants with hydroxyl radical) unexpectedly accelerated DNA degradation, or provided no increase in stability. For example, pentoxifylline and para-aminobenzoic acid are hydroxyl radical scavengers with large rate constants for hydroxyl radicals ($k=1.1\times10^{10}$ $M^{-1}$ $s^{-1}$; see Freitas and Filipe, *Biol. Trace Elem. Res.* 47: 307-311, 1995; Hu et al., *J. Nutr. Biochem.* 6: 504-508, 1995), yet pentoxifylline did not enhance stability and p-aminobenzoic acid actually accelerated DNA degradation. Because of these results, the empirical screening of a number of free radical scavengers has been the most effective means of identifying useful compounds.

To maximize DNA stability in a pharmaceutical formulation, the type of buffer, salt concentration, pH, light exposure as well as the type of sterilization process used to prepare the vials are all important parameters that must be controlled in the formulation to further optimize the stability. Furthermore, lyophilization of the DNA vaccine with appropriate formulation excipients can also be performed enhance DNA stability, presumably by reducing molecular motion via dehydration. Therefore, our data suggest that the formulation that will provide the highest stability of the DNA vaccine will be one that includes a demetalated solution containing a buffer (phosphate or bicarbonate) with a pH in the range of 7-8, a salt (NaCl, KCl or LiCl) in the range of 100-200 mM, a metal ion chelator (succinate, malate, inositol hexaphosphate, tripolyphosphate or polyphosphoric acid), a non-reducing free radical scavenger (ethanol, glycerol, methionine or dimethyl sulfoxide) and the highest appropriate DNA concentration in a sterile glass vial, packaged to protect the highly purified, nuclease free DNA from light.

DNA constructs encoding influenza viral proteins elicit protective immune responses in animals. Immune responses in animals have included antibody and CTL generation in mice, antibody generation in ferrets and primates, and protection from viral challenge in mice and ferrets with homologous, drifted and shifted strains of influenza. Perhaps the most striking result of immunization with DNA encoding viral proteins was the ability to confer protection against distinct subtypes of virus. This suggests that adding a CTL-eliciting component to a vaccine should serve to mitigate the impact of new variants which arise in mid-season or are unanticipated when the vaccine strains are chosen each year for the following year. Importantly, immunization with cDNA vectors encoding an HA, NP and M1 gene was able to protect more effectively against a drifted strain of virus in ferrets than was the licensed vaccine. This provides a justification for the use of constructs encoding internal genes in the IDV (Influenza DNA vaccine).

In one embodiment, the vaccine product will consist of separate DNA plasmids encoding, for example, HA from the 3 prevalent clinical strains representing A/H1N1 (A/Texas/91), A/H3N2 (A/Georgia/93), and B (B/Panama/90) viruses as well as DNA constructs encoding the internal conserved proteins NP and M1 (matrix) from both A (Beijing/89; H3N2) and B strains in order to provide group-common protection against drifted and shifted antigens. The HA DNA will function by generating HA and resulting neutralizing antibodies against HA. This will be type-specific, with some increased breadth of protection against a drifted strain compared to the current licensed, protein-based vaccine. The NP and M1 constructs will result in the generation of CTL which will provide cross-strain protection with potentially lower viral loads and with acceleration of recovery from illness. The expected persistence of the DNA constructs (in an episomal, non-replicating, non-integrated form in the muscle cells) is expected to provide an increased duration of protection compared to the current vaccine.

The anticipated advantages over the current, licensed vaccines include: increased breadth of protection due to CTL responses±increased breadth of antibody, and increased duration of protection. The IDV approach avoids the need to make, select and propagate reassortants as is done for the current licensed vaccine since a new DNA construct can be made more directly from a clinical field isolate. lymphocyte response.

The intramuscular (i.m.). injection of a DNA expression vector encoding a conserved, internal protein of influenza A resulted in the generation of significant protective immunity against subsequent viral challenge. In particular, NP-specific antibodies and primary CTLs were produced. NP DNA immunization resulted in decreased viral lung titers, inhibition of weight loss, and increased survival, compared to controls. The protective immune response was not mediated by the NP-specific antibodies, as demonstrated by the lack of effect of NP antibodies alone (see Example 4) in combating a virus infection, and was thus likely due to NP-specific cellular immunity. Moreover, significant levels of primary CTLs directed against NP were generated. The protection was against a virulent strain of influenza A that was heterologous to the strain from which the DNA was cloned. Additionally, the challenge strain arose more than three decades after the A/PR/8/34 strain, indicating that immune responses directed against conserved proteins can be effective despite the antigenic shift and drift of the variable envelope proteins. Because each of the influenza virus gene products exhibit some degree of conservation, and because CTLs may be generated in response to intracellular expression and MHC processing, it is predictable that other influenza virus genes will give rise to responses analogous to that achieved for NP. Methods for identifying immunogenic epitopes are now well known in the art [see for example Shirai et al., 1992, *J. Immunol* 148:1657-1667; Choppin et al., 1991, *J. Immunol* 147:575-583; Calin-Laurens, et al., 1992, *Vaccine* 11:974-978]. Thus, many of these genes have been cloned, as shown by the cloned and sequenced junctions in the expression vector (see below) such that these constructs are prophylactic agents in available form.

The standard techniques of molecular biology for preparing and purifying DNA constructs enable the preparation of the DNA therapeutics of this invention. While standard techniques of molecular biology are therefore sufficient for the production of the products of this invention, the specific constructs disclosed herein provide novel therapeutics which surprisingly produce cross-strain protection, a result heretofore unattainable with standard inactivated whole virus or subunit protein vaccines.

The amount of expressible DNA to be introduced to a vaccine recipient will depend on the strength of the transcriptional and translational promoters used in the DNA construct, and on the immunogenicity of the expressed gene product. In general, an immunologically or prophylactically effective dose of about 1 μg to 1 mg, and preferably about 10 μg to 300 μg is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided.

The DNA may be naked, that is, unassociated with any proteins, adjuvants or other agents which impact on the recipients immune system. In this case, it is desirable for the DNA to be in a physiologically acceptable solution, such as, but not limited to, sterile saline or sterile buffered saline. Alternatively, the DNA may be associated with liposomes, such as lecithin liposomes or other liposomes known in the art, as a DNA-liposome mixture, (see for example WO93/24640) or the DNA may be associated with an adjuvant known in the art to boost immune responses, such as a protein or other carrier. Agents which assist in the cellular uptake of DNA, such as, but not limited to, calcium ions, viral proteins and other transfection facilitating agents may also be used to advantage. These agents are generally referred to as transfection facilitating agents and as pharmaceutically acceptable carriers. As used herein, the term gene refers to a segment of nucleic acid which encodes a discrete polypeptide. The term pharmaceutical, and vaccine are used interchangeably to indicate compositions useful for inducing immune responses. The terms construct, and plasmid are used interchangeably. The term vector is used to indicate a DNA into which genes may be cloned for use according to the method of this invention.

In another embodiment of this invention, the DNA vaccine encodes human influenza virus nucleoprotein, hemagglutinin, matrix, nonstructural, or polymerase gene product. Specific examples of this embodiment are provided below wherein the human influenza virus gene encodes the nucleoprotein, basic polymerase1, nonstructural protein1, hemagglutinin, matrix1, basic polymerase2 of human influenza virus isolate A/PR/8/34, the nucleoprotein of human influenza virus isolate A/Beijing/353/89, the hemagglutinin gene of human influenza virus isolate A/Texas/36/91, or the hemagglutinin gene of human influenza virus isolate B/Panama/46/90.

Data is presented in this specification which exemplifies several additional DNA vaccine formulations. More specifically, the present invention relates to DNA vaccine formulations which comprise a demetalated solution containing a physiologically acceptable buffer within a pH range from at least greater than about 8.0 to about at least 9.5, a salt (including but not limited to NaCl, KCl or LiCl) in the range of up to about at 300 mM, and the metal ion chelator EDTA (in the range of up to about 5 mM) in combination with the free radical scavenger ethanol (in the range of up to about 3%) and the highest appropriate DNA concentration in a sterile glass vial, packaged to protect the highly purified, nuclease free DNA from light and in a physiologically acceptable buffer.

In a specific aspect of the present invention, the DNA vaccine formulations comprise a combination of EDTA and ethanol, NaCl at a concentration from about 100 mM to about 200 mM, EDTA in the range from about 1 μM to about 1 mM, ethanol present up to about 2%, all in the highest appropriate DNA concentration in a sterile glass vial, packaged to protect the highly purified, nuclease free DNA from light and in a physiologically acceptable buffer.

In another embodiment of the DNA vaccine formulations comprising a combination of EDTA and ethanol, NaCl is present from about 100 mM to about 200 mM, EDTA is present from about 1 μM to about 750 μM, ethanol is present from about 0.5% to about 2.5%, all in the highest appropriate DNA concentration in a sterile glass vial, packaged to protect the highly purified, nuclease free DNA from light and in a physiologically acceptable buffer which preferably is Tris-HCl at a pH from about 8.0 to about 9.0. It will be understood that other known buffers with a buffering capacity within various pH ranges, such as pH 8.0 to 9.5, may be utilized in the various DNA vaccine formulations of the present invention. For example, while Tris-HCl is effective up to about pH 9.0, a glycine buffer will in turn be effective at least in the range from about pH 9.0 to about 9.5.

In an especially preferred aspect of the present invention wherein the DNA vaccine formulations comprise a combination of EDTA and ethanol, NaCl at a concentration from about 100 mM to about 200 mM, EDTA is present at about 500 μM, ethanol is present at about 1.0%, all in the highest appropriate DNA concentration in a sterile glass vial, packaged to protect the highly purified, nuclease free DNA from light and in a physiologically acceptable buffer which preferably is Tris-HCl at a pH from about 8.5 to about 9.0.

Data is presented which shows that the pH of the formulation affects the stability of the DNA, and that the optimum pH is ≧8.5. FIG. 14 indicates that the highest tested formulation (pH 9.0) provided the greatest DNA stability was also at the highest pH used (pH 9). The effect of buffer type on DNA stability was also performed and corresponding data is disclosed herein. Briefly, the greatest buffer effect on DNA stability was seen when comparing glycine and Bis-Tris-Propane. The glycine buffer at pH 9 was significantly superior to the Bis-Tris-Propane formulation at the same pH. In contrast, the Tris, Bicine and Tricine buffers at pH 8.2 provided nearly identical DNA stability out to 12 weeks. The data correlating buffering to DNA stability suggests controlling free radical oxidation of DNA results in overall DNA stability then being controlled by formulation pH.

The effect of light on DNA stability is disclosed herein and it is shown that the detrimental effect of light may be for the most part overcome by the addition of EDTA and ethanol to the formulation. The addition of these formulation components stabilizes DNA in samples stored either in the light or dark. Therefore, DNA vaccine formulations containing EDTA and ethanol will be much less sensitive to the detrimental effects of light and trace metal ions than formulations lacking either of these two stabilizers.

Various data is also disclosed within this specification which tests the effect of demetalating buffers prior to generating DNA vaccine formulations. It is disclosed herein demetalation improves DNA stability slightly in the formulation containing glycerol, but has no effect on DNA stability in an ethanol formulation. This data shows that the same level of DNA stability can be achieved either by controlling free radical oxidation with succinate and ethanol, or by removal of the trace metal ions with demetalation. Data is also presented showing that the enhancement of DNA stability by demetalation is effective over a wide range of temperatures and time in storage.

DNA stability experiments were also performed to show that ethanol is an effective free radical scavenger in the presence of EDTA. The combination of ethanol and EDTA provides a large increase in DNA stability (at pH 7.2) up to 4 weeks, but only a small increase in stability by week 8. These results suggest that ethanol is a more effective scavenger of free radicals in the presence of EDTA than in its absence. Moreover, the results suggest that EDTA alone decreases DNA stability in the absence of ethanol, but increases DNA stability in the presence of ethanol. These results strongly suggest that ethanol is a more effective scavenger in the presence of EDTA because EDTA removes metal ions bound to DNA, thereby allowing the generation of hydroxyl radicals in the bulk solution, as opposed to the generation of radicals by iron bound to the DNA. The data presented to exemplify the present invention also shows that the DNA stabilizing effects of ethanol and EDTA/EtOH are greater at pH 8.0 than at pH 7.2. It is shown further that a similar degree of protection can be obtained from the combination of succinate and ethanol.

Another exemplified portion of the invention relates to alternative metal ion chelators, including but not necessarily limited to NTA (nitrilotriacetic acid) and DTPA (diethylenetriaminepentaacetic acid). Data is presented which shows that NTA or DTPA, preferably DTPA, enhance DNA stability in the absence of ethanol.

The present invention relates to either liquid or lyophilized DNA vaccine formulations. Data is presented which shows that stability of the best lyophilized formulation exceeded that of the liquid formulations over the short term whereas liquid formulations showed good stability over longer periods of time. The results also show that demetalation improves the stability of the lyophilized DNA in formulations 1 and 2, but has little effect on the % SC DNA in the other lyophilized formulations. Therefore, lyophilization is an effective method for stabilizing DNA vaccines and demetalation of the formulation buffer improves the stability of lyophilized DNA in some formulations.

The following examples are provided to further define the invention, without limiting the invention to the specifics of the examples.

EXAMPLE 1

V1J Expression Vector—V1J is derived from vectors V1 and pUC18, a commercially available plasmid. V1 was digested with SspI and EcoRI restriction enzymes producing two fragments of DNA. The smaller of these fragments, containing the CMVintA promoter and Bovine Growth Hormone (BGH) transcription termination elements which control the expression of heterologous genes, was purified from an agarose electrophoresis gel. The ends of this DNA fragment were then "blunted" using the T4 DNA polymerase enzyme in order to facilitate its ligation to another "blunt-ended" DNA fragment.

pUC18 was chosen to provide the "backbone" of the expression vector. It is known to produce high yields of plasmid, is well-characterized by sequence and function, and is of minimum size. We removed the entire lac operon from this vector, which was unnecessary for our purposes and may be detrimental to plasmid yields and heterologous gene expression, by partial digestion with the HaeII restriction enzyme. The remaining plasmid was purified from an agarose electrophoresis gel, blunt-ended with the T4 DNA polymerase, treated with calf intestinal alkaline phosphatase, and ligated to the CMVintA/BGH element described above. Plasmids exhibiting either of two possible orientations of the promoter elements within the pUC backbone were obtained. One of these plasmids gave much higher yields of DNA in *E. coli* and was designated V1J. This vector's structure was verified by sequence analysis of the junction regions and was subsequently demonstrated to give comparable or higher expression of heterologous genes compared with V1.

EXAMPLE 2

Influenza Virus Gene Constructs In Expression Vector V1j—Many of the genes from the A/PR/8/34 strain of influenza virus were cloned into the expression vector V1J, which gives rise to expression at levels as high or higher than in the V1 vector. The PR8 gene sequences are known and available in the GENBANK database. For each of the genes cloned below, the size of the fragment cloned was checked by sizing gel, and the GENBANK accession number against which partial sequence was compared are provided. For a method of obtaining these genes from virus strains, for example from virus obtained from the ATCC (A/PR/8/34 is ATCC VR-95; many other strains are also on deposit with the ATCC).

A. Subcloning the PR8 Genes into V1J:

1. NP—The NP gene was subcloned from pAPR501 (J. F. Young, U. Desselberber, P. Graves, P. Palese, A. Shatzman, and M. Rosenberg (1983), in *The Origins of Pandemic Influenza Viruses*, ed. W. G. Laver, (Elsevier, Amsterdam) pp. 129-138). It was excised by cutting pAPR501 with EcoRI, the fragment gel purified, and blunted with T4 DNA Polymerase. The blunted fragment was inserted into V1J cut with Bgl II and also blunted with T4 DNA Polymerase. The cloned fragment was 1.6 kilobases long.

2. NS—The NS gene was subcloned from pAPR801 (J. F. Young, U. Desselberber, P. Graves, P. Palese, A. Shatzman, and M. Rosenberg (1983), in *The Origins of Pandemic Influenza Viruses*, ed. W. G. Laver, (Elsevier, Amsterdam) pp. 129-138). It was excised by cutting pAPR801 with EcoRI, the fragment gel purified, and blunted with T4 DNA Polymerase. The blunted fragment was inserted into V1J cut with Bgl II and also blunted with T4 DNA Polymerase. The cloned fragment was 0.9 kilobases long (the complete NS coding region including NS1 and NS2).

3. HA—The HA gene was subcloned from pJZ102 (J. F. Young, U. Desselberber, P. Graves, P. Palese, A. Shatzman, and M. Rosenberg (1983), in *The Origins of Pandemic Influenza Viruses*, ed. W. G. Laver, (Elsevier, Amsterdam) pp. 129-138). It was excised by cutting pJZ102 with Hind III, the fragment gel purified, and blunted with T4 DNA Polymerase. The blunted fragment was inserted into V1J cut with Bgl II and also blunted with T4 DNA Polymerase. The cloned fragment was 1.75 kilobases long.

4. PB1—The PB1 gene was subcloned from pGem1—PB1 (The 5' and 3' junctions of the genes with the vector were sequenced to verify their identity. See J. F. Young, U. Desselberber, P. Graves, P. Palese, A. Shatzman, and M. Rosenberg (1983), in *The Origins of Pandemic Influenza Viruses*, ed. W. G. Laver, (Elsevier, Amsterdam) pp. 129-138). It was excised by cutting pGem-PB1 with Hind III, the fragment gel purified, and blunted with T4 DNA Polymerase. The blunted fragment was inserted into V1J cut with Bgl II and also blunted with T4 DNA Polymerase. The cloned fragment was 2.3 kilobases long.

5. PB2—The PB2 gene was subcloned from pGem1-PB2 (The 5' and 3' junctions of the genes with the vector were sequenced to verify their identity. See J. F. Young, U. Desselberber, P. Graves, P. Palese, A. Shatzman, and M. Rosenberg (1983), in *The Origins of Pandemic Influenza Viruses*, ed. W. G. Laver, (Elsevier, Amsterdam) pp. 129-138). It was excised by cutting pGem-PB2 with BamH I, and gel purifying the fragment. The sticky-ended fragment was inserted into V1J cut with Bgl II. The cloned fragment was 2.3 kilobases long.

6. M1—The M1 gene was generated by PCR from the plasmid p8901 MITE. The M sequence in this plasmid was generated by PCR from pAPR701 (J. F. Young, U. Desselberber, P. Graves, P. Palese, A. Shatzman, and M. Rosenberg (1983), in *The Origins of Pandemic Influenza Viruses*, ed. W. G. Laver, (Elsevier, Amsterdam) pp. 129-138.). The PCR fragment was gel purified, cut with Bgl II and ligated into V1J cut with Bgl II. The cloned fragment was 0.7 kilobases long. The amino terminus of the encoded M1 is encoded in the "sense" primer shown above as the "ATG" codon, while the M1 translation stop codon is encoded by the reverse of the "TCA" codon, which in the sense direction is the stop codon "TGA".

B. Influenza Gene-V1J Expression Constructs

In each case, the junction sequences from the 5' promoter region (CMVintA) into the cloned gene is shown. The position at which the junction occurs is demarcated by a "/", which does not represent any discontinuity in the sequence. The method for preparing these constructs is summarized after all of the sequences below. Each sequence provided represents a complete, available, expressible DNA construct for the designated influenza gene.

Each construct was transiently transfected into RD cells, (ATCC CCL136), a human rhabdomyosarcoma cell line in culture. Forty eight hours after transfection, the cells were harvested, lysed, and western blots were run (except for the V1J-PR-HA construct which was tested in mice and gave anti-HA specific antibody before a western blot was run, thus obviating the need to run a western blot as expression was observed in vivo). Antibody specific for the PB1, PB2 and NS proteins was provided by Stephen Inglis of the University of Cambridge, who used purified proteins expressed as β-galactosidase fusion proteins to generate polyclonal antisera. Anti-NP polyclonal antiserum was generated by immunization of rabbits with whole A/PR/8/34 virus. Anti-M1 antibody is commercially available from Biodesign as a goat, anti-fluA antiserum, catalog number B65245G. In each case, a protein of the predicted size was observed, confirming expression in vitro of the encoded influenza protein.

The nomenclature for these constructs follows the convention: "Vector name-flu strain-gene". In every case, the sequence was checked against known sequences from GENBANK for the cloned and sequenced A/PR/8/34 gene sequence.

C. Production of V1jns

An Sfi I site was added to V1Jneo to facilitate integration studies. A commercially available 13 base pair Sfi I linker (New England BioLabs) was added at the Kpn I site within the BGH sequence of the vector. V1Jneo was linearized with Kpn I, gel purified, blunted by T4 DNA polymerase, and ligated to the blunt Sfi I linker. Clonal isolates were chosen by restriction mapping and verified by sequencing through the linker. The new vector was designated V1Jns. Expression of heterologous genes in V1Jns (with Sfi I) was comparable to expression of the same genes in V1Jneo (with Kpn I).

EXAMPLE 3

Growth of Microbial Cells, Cell Lysis and Clarification—One liter of frozen *E. coli* cell slurry was used to make 8 liters of cell suspension in STET buffer (8% sucrose, 0.5% TRITON, 50 mM TRIS buffer, pH 8.5 and 50 mM EDTA). The absorbance of the cell suspension at 600 nm was about O.D. 30. The suspension was stirred continuously to ensure homogeneity. The viscosity of the cell suspension was measured to be about 1.94 cp at room temperature (24° C.). The cell suspension was pumped through the heat exchanger at 81 mL/min which corresponded to a residence time of the cell solution in the heat exchanger of about 35 seconds. The bath temperature was maintained at 92° C. The inlet and outlet temperatures of the cell solution were measured to be about 24° C. and about 89° C. (average), respectively. About 1 liter of sample was run through the heat exchanger. No visible clogging of the tube was observed although the lysate was somewhat thicker than the starting material. The lysate was cooled to room temperature and its viscosity was measured to be about 40 cp. The cell lysate was clarified by batch centrifugation at 9000 RPM for 50 minutes using the Beckman J-21. Analysis of the supernatant confirmed effective cell lysis and product recovery. The product yield produced by flow-through heat lysis was at least comparable to that made by the Quigley & Holmes boiling method. The latter method; however, must be carried out at the laboratory scale in batch mode and is therefore unsuitable for large-scale (5 liters or greater) processing. Since the heat exchanger process is flow-through, there is no maximum limit to the volume of cell suspension that can be processed. This process can therefore accomodate very large scale fermentations of bacteria to produce large quantities of highly purified plasmid DNA.

The clarified lysate was then filtered through a membrane having a pore size of 0.45 microns to remove finer debris. The filtrate was then diafiltered using a membrane having a molecular weight cutoff of about 100,000.

EXAMPLE 4

Control and Reproducibility of Cell Lysis with the Heat Exchanger—Adjusting the flowrate (i.e., residence time) at which the cell slurry is pumped through the heat exchanger permits tight control of the temperature of lysis, i.e., the outlet temperature. A cell slurry solution was prepared as described in Example 3 and pumped through the heat exchanger at flow rates ranging from 160 to 850 mL/min. The corresponding outlet temperatures ranged between 93° C. and 65° C., respectively. The initial temperature of the cell slurry was 24° C. and the bath temperature was kept constant at 96° C. In addition, a number of runs were performed where an outlet temperature of 80° C. was targeted. Yields of 24 mg of circular DNA per L of clarified supernatant were consistently obtained demonstrating the reproducibility of the process.

EXAMPLE 5

Purification of Plasmid DNA—Microbial cells and lysates were prepared as described, and the following analyses were performed. To illustrate that the addition of 100 mM EDTA vs 50 mM EDTA increased the percentage of supercoiled DNA, and to determine an acceptable range of outlet temperatures (i.e., lysis temperature) with respect to recovery of supercoiled DNA, the following analyses were performed. The supercoiled form of plasmid DNA is desirable since it is more stable than the relaxed circle form. One way that supercoiled DNA can be converted to open circle is by nicking with DNase. We found that the addition of 100 mM EDTA vs 50 mM in the STET buffer minimized the formation of open circle plasmid. The cell suspension was prepared as described. The operating flow rate for these runs was approximately 186 ml/min. The temperatures of the inlet, outlet and bath are 24° C., 92° C. and 96° C. respectively.

An acceptable range of lysis temperatures was determined by measuring the percentage of supercoiled plasmid generated for each run. The concentration of supercoiled plasmid as a function of exit temperature. An acceptable range of lysis temperatures is between 75° C. and 92° C. At temperatures below 75° C., more relaxed circle plasmid was generated, most likely due to increased DNase activity. Above 93° C., the levels of supercoiled plasmid appear to diminish, possibly due to heat denaturation.

Following continuous heat lysis and centrifugation, 1 mL of clarified lysate was either incubated with 5 μg RNase for 2 hours, or was used untreated. The RNase treated and untreated samples were then loaded onto an anion exchange column (Poros Q/M 4.6×100) that had been previously equilibrated with a 50-50 mixture of solvents A and B [HPLC solvent A: 20 mM Tris/Bis Propane, pH 8.0; and solvent B: 1 M NaCl in 20 mM Tris/Bis Propane, pH 8.0]. The column was eluted using a gradient of 50% to 85% B run over 100 column volumes. Open circle plasmid elutes at approximately 68% B and supercoiled elutes at 72% B.

As described above, diafiltration prior to anion exchange chromatography greatly increases the amount of lysate that can be loaded onto the column.

The plasmid DNA eluted from the anion exchange column was separated into the individual forms by reversed phase HPLC analysis. The forms are supercoiled plasmid (form 1) and nicked circle (form 2). The two forms were easily separated and allowed the isolation of individual forms of the plasmid.

EXAMPLE 6

Highly Purified Plasmid DNA From a Chromatography-Based Process—A fermentation cell paste was resuspended in modified STET buffer and then thermally lysed in a batch-wise manner. Alternatively a fermentation cell paste is resuspended in modified STET buffer and then thermally lysed in the flow-through process described above. The lysate was centrifuged as described above. Twenty ml of the supernatant were filtered as described above and loaded onto an anion exchange column (Poros Q/M 4.6×100) that was previously equilibrated with a 50-50 mixture of buffers A and B described above. A gradient of 50% to 85% B was run over 50 column volumes with a flow rate of 10 ml/minute. Fractions of 2.5 ml each were collected from the column. The supercoiled plasmid DNA eluted from the column at 72% B.

The anion exchange product was then loaded onto a reversed phase chromatography column (Poros R/H) which had been previously equilibrated with 100 mM ammonium bicarbonate at pH 8.0, and a gradient of 0% to 80% methanol was used to elute the bound material. The highly purified supercoiled plasmid DNA eluted at 22% methanol.

Figure 9:
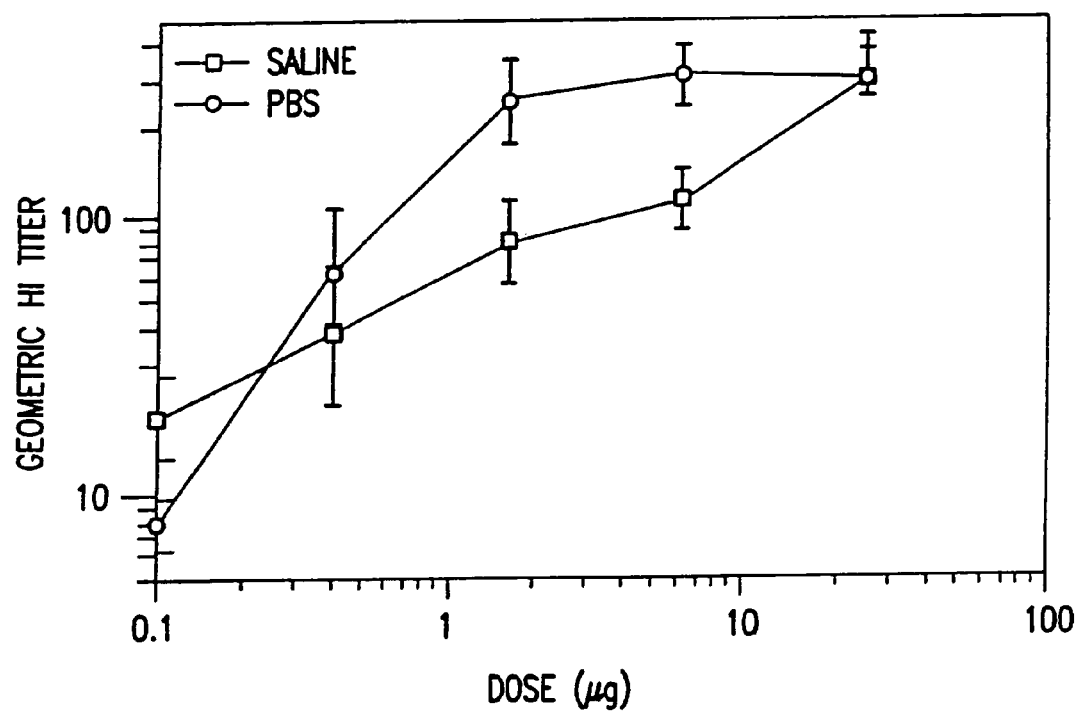
FIG. 9 shows an induced mouse immune response as measured by HI titer for a single injection of PBS vs. saline formulated Influenza DNA vaccine, HA (Georgia/93). DNA plasmid solutions were prepared at various doses and 200 microliters of the vaccine was injected in each mouse (ten mice per dose per formulation).

Based on the agarose gels and the colorimetric and HPLC assays described, the final product, shown in FIG. 9, is highly pure. The product consists of greater than 90% supercoiled and less than 10% open circle plasmid. RNA was below the limits of detection of the assay used. Genomic DNA and protein contaminant levels were also below the limits of detection in the assays used. The overall supercoiled plasmid yield at the end of the process was approximately 60% of the supercoiled plasmid in the clarified lysate.

EXAMPLE 7

Multi-Gram Scale Purification of Plasmid DNA—4.5 L of frozen E. coli cell slurry was used to make 33.7 L of cell suspension in STET buffer (8% sucrose, 2% Triton, 50 mM Tris buffer, 50 mM EDTA, pH 8.5) with 2500 units/ml of lysozyme. The absorbance of the suspension at 600 nm was about O.D. 30. The suspension was stirred at room temperature for 15 minutes to ensure proper mixing and then was incubated for 45 minutes with continuous stirring at 37° C. Following incubation, mixing was continued at room temperature and the cell suspension was pumped through the heat exchanger at a flowrate of 500 ml/min. The batch temperature was maintained at 100° C. and the inlet and outlet temperatures of the cell suspension were measured to be about 24° C. and between 70-77° C., respectively. The cell lysate exiting the heat exchanger was collected in Beckman centrifuge bottles (500 mls each) and the material was centrifuged immediately in Beckman J-21 centrifuges for 50 minutes at 9000 RPM. Following centrifugation, the supernatant was found to contain 4-5 times more plasmid product than in the case without lysozyme incubation. The supernatant product of the centrifugation was immediately diafiltered against 3 volumes of TE buffer (25 mM Tris-EDTA at pH 8.0) and then incubated with $20 \times 10^5$ units of E. coli RNase for 2-4 hours at room temperature. After completion of the incubation, the product solution was then diafiltered an additional 6 volumes with TE buffer using a 100 kD MWCO membrane and then filtered through a 0.45 micron filter to remove residual debris. The filtered lysate was diluted to 0.7 M NaCl with a 20 mM Bis/Tris Propane-NaCl buffer at pH 7.5, which prepares the diluted filtrate for loading onto the anion exchange column. The anion exchange column (3.6 L of POROS PI/M) was previously equilibrated with 20 mM Bis/Tris Propane and 0.7M NaCl. The filtered lysate was loaded to column capacity. In this case 5 grams of supercoiled plasmid was loaded onto the anion exchange column. After loading, the column was washed with 24 column volumes of 20 mM Bis/Tris Propane and 0.7 M NaCl. A 10 column volume gradient from 0.7 M NaCl to 2.0 M NaCl in 20 mM Bis/Tris Propane was performed to clear most of the E. coli protein. RNA and some endotoxin. The supercoiled plasmid fraction eluted between 1.4 M and 2.0 M NaCl. The supercoiled fraction from the anion exchange column, which contained 4 grams of supercoiled plasmid was then diluted 2-3 times with pyrogen free water, adjusted to 1.2% IPA and pH adjusted to 8.5 with 1 N NaOH. The diluted anion exchange supercoiled fraction was then loaded onto a 7 L reversed phase column (POROS R2/M) which had been previously equilibrated with 100 mM Ammonium Bicarbonate containing 1.2% IPA. In this case, 3.2 grams of supercoiled plasmid were loaded onto the reversed phase column and then the column was washed with 6-10 column volumes of 1.2% IPA in 100 mM Ammonium Bicarbonate. This extensive wash was performed to clear impurities. Next, a gradient of 1.2% IPA to 11.2% IPA in 5 column volumes was performed. The supercoiled plasmid fraction elutes at about 4% IPA. The supercoiled product fraction from the reversed phase column was then concentrated and diafiltered into normal saline using a 30 kD MWCO membrane. The final product bulk was filtered through a 0.22 micron filter. The overall product yield of the process was more than 50% of the supercoiled plasmid in the clarified cell lysate as indicated by the anion exchange HPLC assay.

EXAMPLE 8

Polynucleotide Vaccination in Primates

Antibody to NP in Rhesus monkeys—Rhesus monkeys (006 NP, 009 NP or control 101; 021) were injected with 1 mg/site of RSV-NP i.m. in 3 sites on day 1. Injections of 1 mg each of RSV-LUX and CMV-int-LUX, constructs for the reporter gene firefly luciferase expression, were given at the same time into separate sites. Animals were re-injected on day 15 with the same amounts of DNA as before and also with 1 mg of pD5-CAT, a construct for the reporter gene chloramphenical acetyl transferase expression, in 1 site each. Muscle sites containing reporter genes were biopsied and assayed for reporter gene activity. Serum was collected 3, 5, 9, 11, 13, and 15 weeks after the first injection. The first positive sample for anti-NP antibody was collected at week 11 and positive samples were also collected on weeks 13 and 15. Anti-NP antibody was determined by ELISA.

Hemagglutination inhibiting (HI) antibody in rhesus monkeys—Monkeys were injected i.m. with V1J-PR-HA on day 1. Two animals each received 1 mg, 100 µg, or 10 µg DNA in each quadriceps muscle. Each injection was administered in a volume of 0.5 ml. Animals were bled prior to injection on day 1. All animals were reinjected with DNA on day 15, and blood was collected at 2-4 week intervals thereafter. Hemagglutination inhibition (HI) titers against A/PR/8/34 were positive at 5 weeks, 9 weeks and 12 weeks after the first injection of V1J-PR-HA DNA.

EXAMPLE 9

Effect of container type and DNA concentration on DNA stability—The conversion of supercoiled plasmid DNA to its open circular and linear forms is a major physicochemical change occurring during in vitro storage. In Examples 9-16 the effects of a variety of storage conditions on the stability of plasmid DNA were determined by monitoring the chemical cleavage of the phosphodiester backbone, leading to the conformational conversion of supercoiled plasmid DNA to open circular and linear forms. To monitor this change, plasmid DNA (Influenza DNA vaccine, HA (Georgia/93) was formulated, sterilized by sterile filtration if necessary, placed in sterile capped glass vials (0.8 mL in 3 mL vials) and incubated at various temperatures. Following the incubation period, a single vial of each particular formulation was removed from the incubator and frozen at minus 70° C. Each vial was then thawed and 20 ng of DNA from the vial was applied to a 1% agarose gel and electrophoresed for 90 minutes. The gel was then stained with ethidium bromide, destained and photographed under UV illumination. To quantitate the amount of supercoiled, open circle and linear DNA in each sample, the negative of the gel photograph was scanned with a Bio-RAD (GS-670) densitometer. The absorbance data for each lane on the gel was then compared to the absorbance of a series of supercoiled, open circle and linear DNA standards on the same gel using a computer program (Molecular Analyst, version 1.3, BIO-RAD Laboratories). The absorbance of the DNA standards was used to construct a standard curve for supercoiled, open circle and linear DNA. Seven DNA standards of each form were applied to the gel (1 to 30 ng of supercoiled DNA, 0.1875 to 15 ng of open circle and linear DNA). To express the stability of the DNA over time, the amount of supercoiled DNA in the sample at time zero was normalized to 100% (the initial % supercoiled DNA normally ranged from 90-100%). The stability of the DNA samples was then expressed as the percent of initial supercoiled DNA remaining after some period of incubation. Although the were each determined from sampling a single vial, multiple time points were usually taken to allow the observation of a decreasing percent supercoiled DNA remaining over an extended period of time. For samples incubated at 50° C. the sampling time points were usually at 1, 2, 4, 6 and 8 weeks, while the 4, 25 and 37° C. samples were analyzed after 1, 2, 3 and sometimes 6 months.

Figure 2:
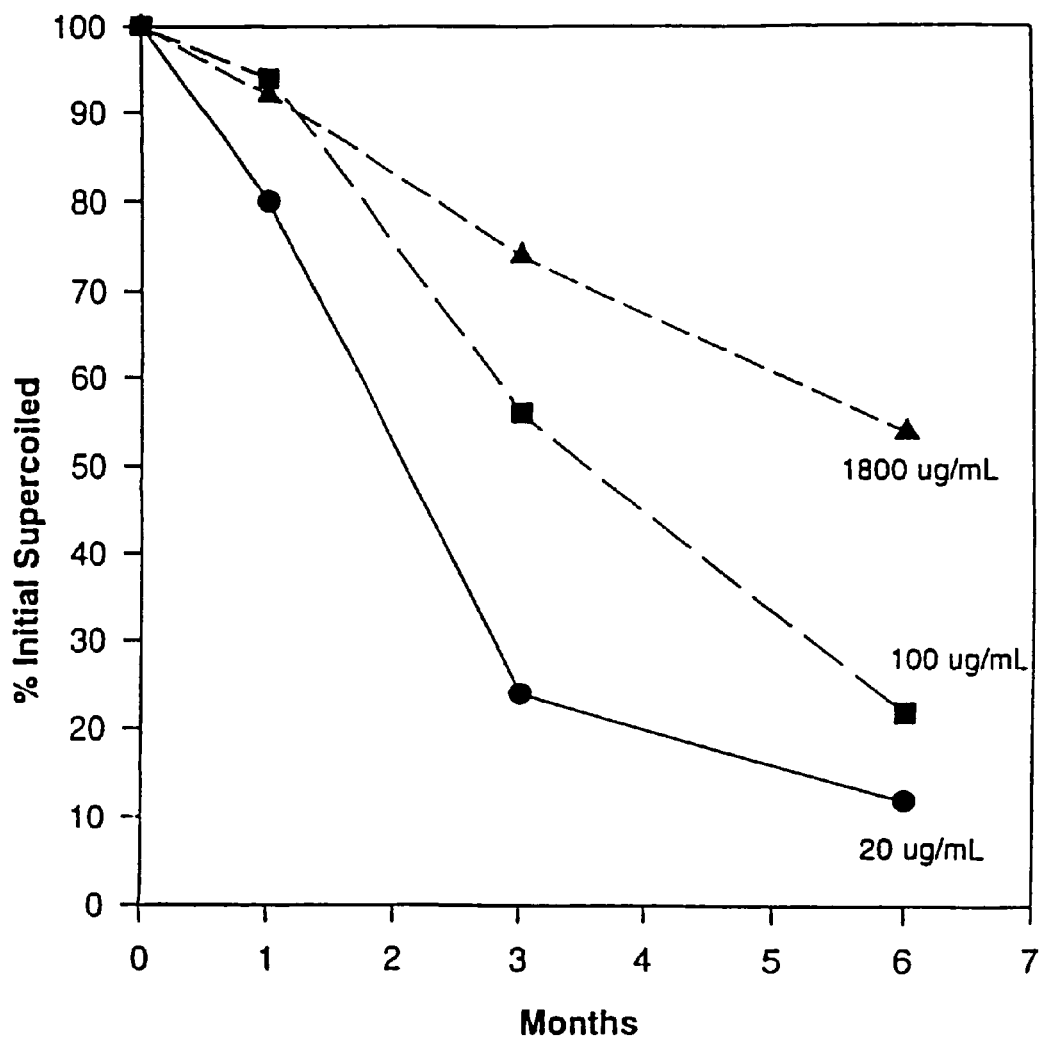
FIG. 2 shows the effect of DNA plasmid concentration on supercoil content of Influenza DNA vaccine, HA (Georgia/93) during storage at 37° C. DNA plasmid solution was prepared at 20-1800 mcg/mL. Supercoil content of plasmid was determined by agarose gel electrophoresis.

Using chromatographically purified plasmid DNA, preformulation experiments were initiated to determine the potential mechanism of plasmid degradation during in vitro storage under a variety of storage conditions. To examine the stability of the Influenza DNA vaccine (Georgia/93) during exposure to different container types plasmid DNA (100 mcg/mL in saline) was incubated in different containers for 6 months at 5, 24 and 37° C. The results (FIGS. 1A, 1B, 1C and 1D) indicated that glass vials were superior to siliconized glass, autoclaved plastic or gamma radiated plastic vials for stabilizing the DNA. To determine the effect of DNA concentration on stability, plasmid DNA at 20, 100 and 1800 mcg/mL in saline was incubated for 6 months at 37° C. An analysis of the supercoiled DNA content indicated that stability was dose dependent, with higher concentrations of plasmid being more stable during storage at 37° C. (FIG. 2). Further studies on the effect of DNA concentration, with the DNA formulated in saline or PBS, also indicated that higher concentrations were more stable at 2 to 8° C. (Table 1A) and at minus 70° C. (Table 1B).

TABLE 1

Stability data for Influenza DNA vaccine, HA (Georgia/93) formulations stored at (A) 2 to 8° C. and (B) minus 70° C.

(A)

| Formulation/Lot # | Buffer[1] | Test | initial | 1 month | 3 month |
|---|---|---|---|---|---|
| High mcg/mL[2] | Saline | % SC | 94 | 94 | 93 |
| V510-HSS-001-C001 |  | pH | 6.6 | 6.6 | 6.5 |
| V510-PBS-1.0 | PBS | % SC | 96 | 95 | 96 |
|  |  | pH | 7.3 | 7.3 | 7.3 |
| 20 mcg/mL | Saline | % SC | 91 | 66 | 63 |
| V510-HSS-001-B002 |  | pH | 6.7 | 6.3 | 6.3 |
| V510-HSS-003-A002 | PBS | % SC | 91 | 93 | 90 |
|  |  | pH | 7.2 | 7.2 | 7.2 |
| 2 mcg/mL | Saline | % SC | 87 | 67 | 48 |
| V510-HSS-001-B001 |  | pH | 6.3 | 6.0 | 6.5 |
| V510-HSS-003-B002 | PBS | % SC | 93 | 92 | 91 |
|  |  | pH | 7.2 | 7.1 | 7.2 |

[1]0.9% Saline, adj. to pH 7.2; PBS: 6 mM Phosphate Buffer Containing 150 mM Saline, pH 7.2
[2]High mcg/mL: Saline formulated at 2,200 mcg DNA/mL, PBS formulated at 1,000 mcg DNA/mL
% SC = % supercoiled TABLE 1-continued (B)

| Formulation/Lot # | Buffer[1] | Test | initial | 1 | 3 |
|---|---|---|---|---|---|
| High mcg/mL[2] | Saline | % SC | 94 | NS | 91 |
| V510-HSS-001-C001 | | pH | 6.6 | NS | 6.4 |
| V510-PBS-1.0 | PBS | % SC | 96 | 94 | 97 |
| | | pH | 7.3 | 7.3 | 7.4 |
| 20 mcg/mL | Saline | % SC | 91 | 86 | 84 |
| V510-HSS-001-B002 | | pH | 6.7 | NS | 6.3 |
| V510-HSS-003-A002 | PBS | % SC | 91 | 95 | 95 |
| | | pH | 7.3 | 7.2 | 7.2 |
| 2 mcg/mL | Saline | % SC | 87 | 83 | 76 |
| V510-HSS-001-B001 | | pH | 6.3 | 6.1 | 6.6 |
| V510-HSS-003-B002 | PBS | % SC | 93 | 93 | 95 |
| | | pH | 7.2 | 7.2 | 7.2 |

[1]0.9% Saline, adj. to pH 7.2; PBS: 6 mM Phosphate Buffer Containing 150 mM Saline, pH 7.2
[2]High mcg/mL: Saline formulated at 2,200 mcg DNA/mL, PBS formulated at 1,000 mcg DNA/mL
NS: Not scheduled DNA stability experiments show that the rubber stoppers used to cap the glass vial containers have a detrimental effect on DNA stability. Table 2 shows the effects of three stopper types on DNA stability in two different DNA vaccine formulations. The vials (containing the DNA solutions, 2 mcg/mL) were incubated at 50° C. in both the right-side up and up-side down configuration to determine the effect of the stoppers on DNA stability. The DNA was more stable when the vials were incubated in the right-side up configuration, for each stopper type tested. Furthermore, the addition of ethanol enhances DNA stability and reduces the degradative effect of the stopper. For stopper #3 (Table 2), the addition of ethanol totally eliminated the degradative effect of the stopper on DNA stability. These results suggest that the stopper contributes to DNA degradation during storage, and that ethanol can be used to control the degradative effects of some stopper types, on DNA stability.

To determine how much the stopper influences the stability of DNA in glass vials an experiment was carried out to determine the stability of DNA over 8 weeks at 50° C., in glass vials with three different types of stoppers and in sealed glass ampules. Table 3 shows formulations with and without succinate (a DNA stability enhancer), the DNA was significantly more stable in sealed glass ampules than in glass vials with any of the tested stoppers. Also, there were only small differences in DNA stability among the vials with the three different stopper types. These data show that different stopper types in four different formulations (Tables 2, 3) contribute significantly to DNA degradation. The optimization of DNA stability in glass vials will require the testing of several stopper types, and may also require the addition of free radical scavengers like ethanol to control to degradative effects of the stopper.

TABLE 2

Summary of the effects of stopper type on DNA stability, in formulations with and without ethanol. Percent of initial supercoiled DNA was determined by agarose gel electrophoresis.

DNA = Influenza DNA vaccine
Volume and concentration = 0.8 mL/vial at 2.0 ug/mL
Temperature = 50 C.
Container = 3 mL glass vials, with three different kinds of stoppers
Stopper #1-Teflon coated and siliconized, type 1888
Stopper#2-Teflon coated, non-siliconized, type 1888

TABLE 2-continued

Summary of the effects of stopper type on DNA stability, in formulations with and without ethanol. Percent of initial supercoiled DNA was determined by agarose gel electrophoresis.

Stopper#3-Teflon coated, non-siliconized, low extractables, type 4405/50 Stoppers sold by "The West Company", Lionville, PA
Time 0 = 25 Apr
Conditions C1–C3 contained demetalated PBS, pH 8.15.
Conditions C4–C6 contained demetalated PBS with 5% Ethanol, pH 8.15
C1 = stopper #1
C2 = stopper #2
C3 = stopper #3
C4 = stopper #1
C5 = stopper #2
C6 = stopper #3

| | % of Initial supercoiled DNA remaining | | | |
|---|---|---|---|---|
| Conditions | 25-Apr Initial % SC | 9-May 2 weeks | 23-May 4 weeks | 20-Jun 8 weeks |
| C1-up* | 92 | 85 | 40 | 21 |
| C1-down** | 92 | 72 | 18 | 0 |
| C2-up | 95 | 81 | 46 | 26 |
| C2-down | 95 | 77 | 3 | 0 |
| C3-up | 93 | 26 | 8 | 0 |
| C3-down | 93 | 30 | 10 | 0 |
| C4-up | 95 | 93 | 64 | 47 |
| C4-down | 95 | 86 | 39 | 25 |
| C5-up | 95 | 92 | 71 | 45 |
| C5-down | 95 | 86 | 62 | 34 |
| C6-up | 95 | 94 | 78 | 71 |
| C6-down | 95 | 93 | 71 | 71 |

*vials incubated right-side up
**vials incubated up-side down

TABLE 3

Stability of DNA in glass ampules and vials with three stopper types, using formulations with and without succinate. Percent of initial supercoiled DNA was determined by agarose gel electrophoresis.

| | % of Initial Supercoiled DNA Remaining | | | | |
|---|---|---|---|---|---|
| Conditions | 8-Oct Initial % SC | 22-Oct 2 weeks | 5-Nov 4 weeks | 19-Nov 6 weeks | 3-Dec 8 weeks |
| C1 | 93 | 38 | 19 | 7 | 7 |
| C2 | 93 | 53 | 18 | 7 | 3 |
| C3 | 93 | 53 | 23 | 5 | 2 |
| C4 | 93 | 61 | 42 | 32 | 19 |
| C5 | 94 | 59 | 37 | 27 | 11 |
| C6 | 94 | 60 | 37 | 17 | 3 |
| C7 | 94 | 66 | 37 | 16 | 5 |
| C8 | 94 | 68 | 60 | 48 | 39 |

DNA = Influenza DNA vaccine
Volume and Concentration = 0.8 mL per vial or 0.5 mL per ampule at 20 mcg/mL
Temperature = 50 C.
Container = 3 ml glass vials with three different types of stoppers or glass ampules
stopper #1-West 4405, non-siliconized but teflon coated
stopper #2-West 1888, siliconized and teflon coated
stopper #3-West Fluorotec, non-siliconized
Postion = Inverted
Time 0 = 8 Oct
Conditions
C1 = 10 mM NaPO4/150 mM NaCl, pH 8.0-stopper #1
C2 = 10 mM NaPO4/150 mM NaCl, pH 8.0-stopper #2
C3 = 10 mM NaPO4/150 mM NaCl, pH 8.0-stopper #3
C4 = 10 mM NaPO4/150 mM NaCl, pH 8.0-in glass ampules
C5 = 10 mM NaPO4/10 mM Succinate/150 mM NaCl, pH 8.0-stopper #1
C6 = 10 mM NaPO4/10 mM Succinate/150 mM NaCl, pH 8.0-stopper #2
C7 = 10 mM NaPO4/10 mM Succinate/150 mM NaCl, pH 8.0-stopper #3
C8 = 10 mM NaPO4/10 mM Succinate/150 mM NaCl, pH 8.0-in glass ampules

EXAMPLE 10

Figure 3:
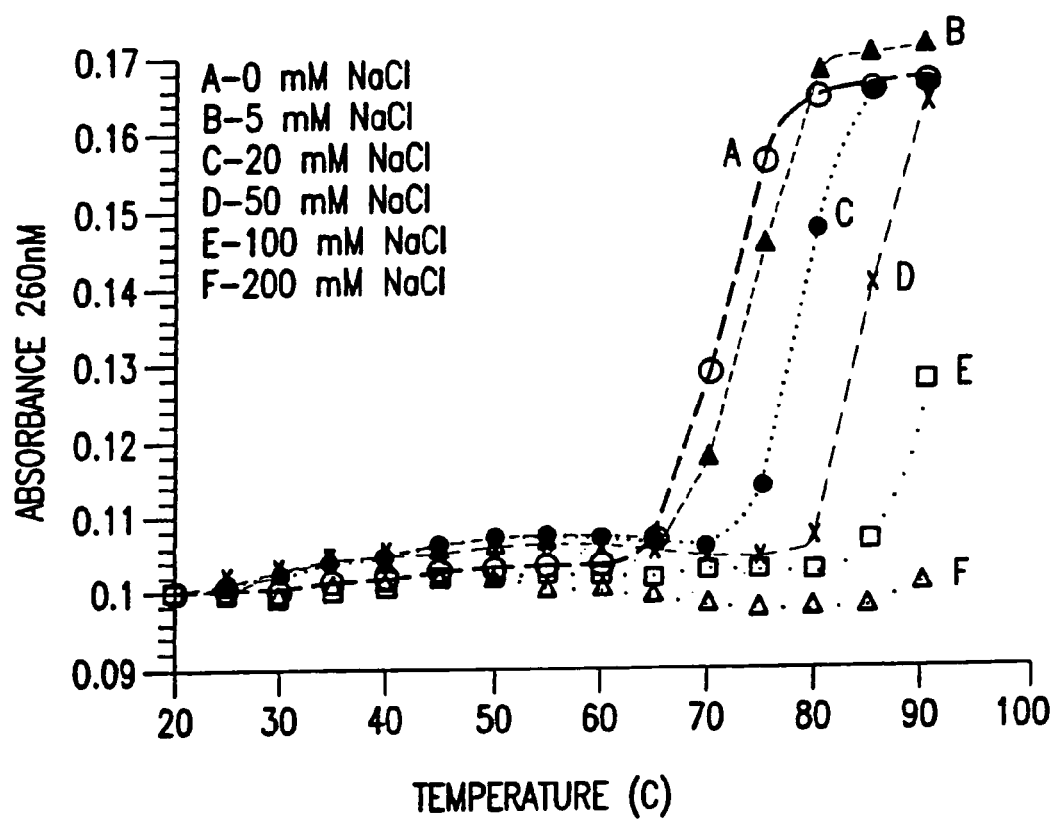
FIG. 3 shows the UV-melting curve of plasmid DNA stored in 10 mM phosphate buffer (pH 6.0) over the NaCl concentration range of 0-200 mM. Samples contained 100 mcg/ml plasmid DNA with the following concentrations of NaCl; (a) 0 mM, (b) 5 mM, (c) 20 mM, (d) 50 mM, (e) 100 mM, (f) 200 mM.

Effect of salt concentration on DNA stability—To examine the effect of salt concentration on DNA stability an initial experiment was set up to determine the melting temperature (Tm) of the DNA over a range of NaCl concentrations from 0 to 200 mM. To determine the Tm at each concentration of NaCl, the UV absorbance of plasmid DNA (10 mcg/mL DNA) formulated in 10 mM sodium phosphate (pH 6.0) was monitored at 260 nm as the temperature was increased. The results (FIG. 3) indicated a Tm of 72°, 73°, 78° and 82° C. for 0, 5, 20 and 50 mM NaCl, respectively. The Tm value for 100 and 200 mM NaCl could not be determined because the strong stabilizing effect of the salt elevated the Tm to greater than 90° C. These results suggest that the minimum NaCl concentration necessary to provide the maximum DNA thermal stability is in the 100-200 mM range.

Figure 4:
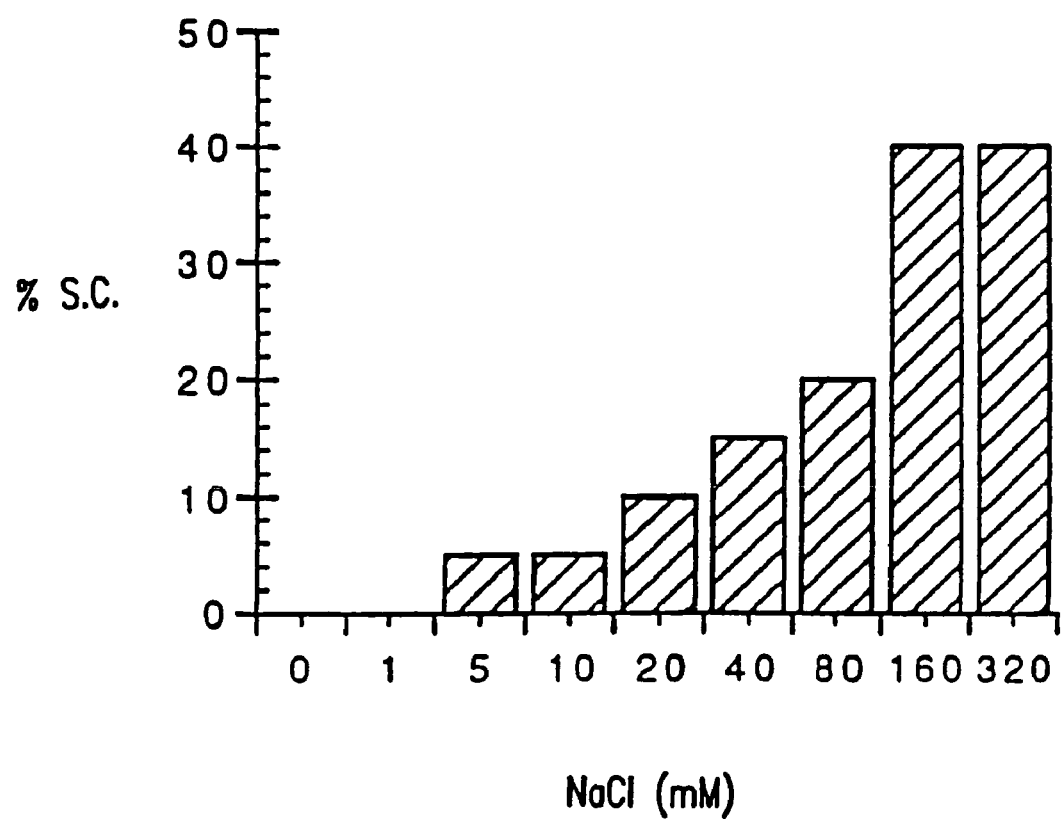
FIG. 4 shows the stability of plasmid DNA in the presence of increasing concentrations of NaCl. Samples were incubated at 60° C. for 48 hours then analyzed by agarose gel electrophoresis. At time zero samples contained 90% supercoiled DNA.

To examine the effect of NaCl concentration on the rate of conversion of supercoiled to open circle DNA during storage, plasmid DNA (100 mcg/mL) was formulated in 10 mM sodium phosphate buffer (pH 7.2) with NaCl varying from 1 to 320 mM. The solutions were incubated at 60° C. for 48 hours and analyzed by agarose gel electrophoresis. The results (FIG. 4) indicated an increase in DNA stability as NaCl concentration was increased from 1 to 160 mM and no significant difference in stability between 160 and 320 mM. These results are consistent with those of FIG. 3, suggesting that the minimum NaCl concentration necessary for maximum DNA stability is between 100-200 mM.

Figure 5A:
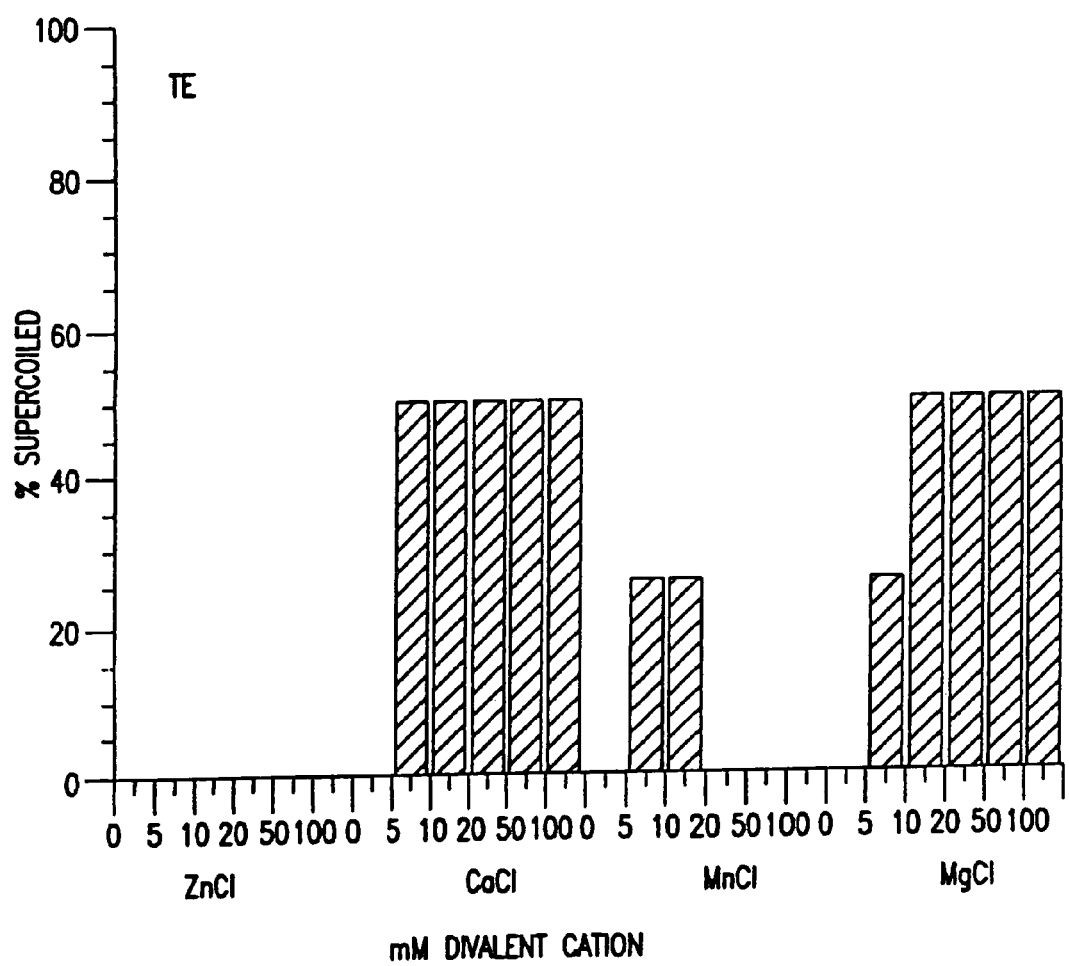
FIG. 5A, FIG. 5B and FIG. 5C show the stability of plasmid DNA in the presence of divalent cations in TE (Panel A), PBS (Panel B) and saline (Panel C). Samples were heated at 60° C. for 48 hours at a concentration of 100 mcg/mL then analyzed for degradation by agarose gel electrophoresis. At time zero, samples contained 90% supercoiled DNA.
Figure 5B:
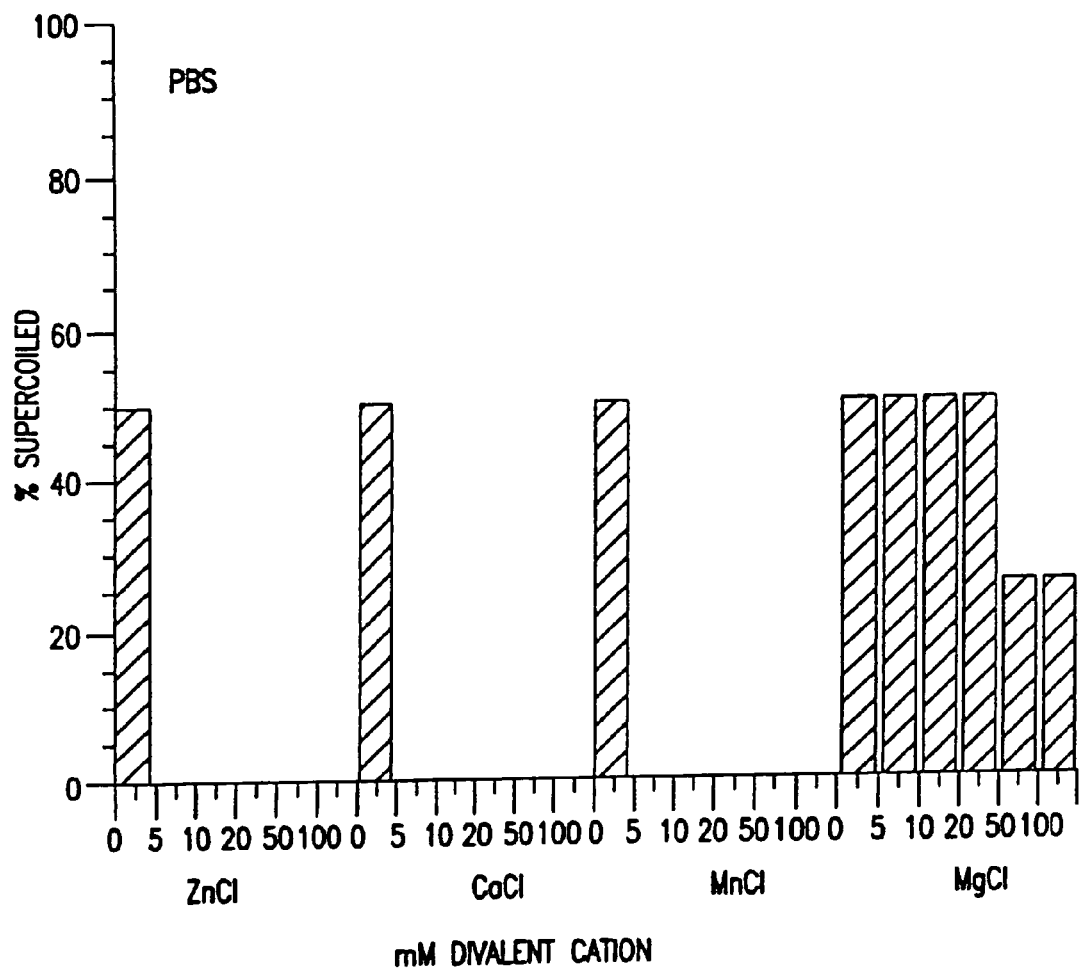
Figure 5C:
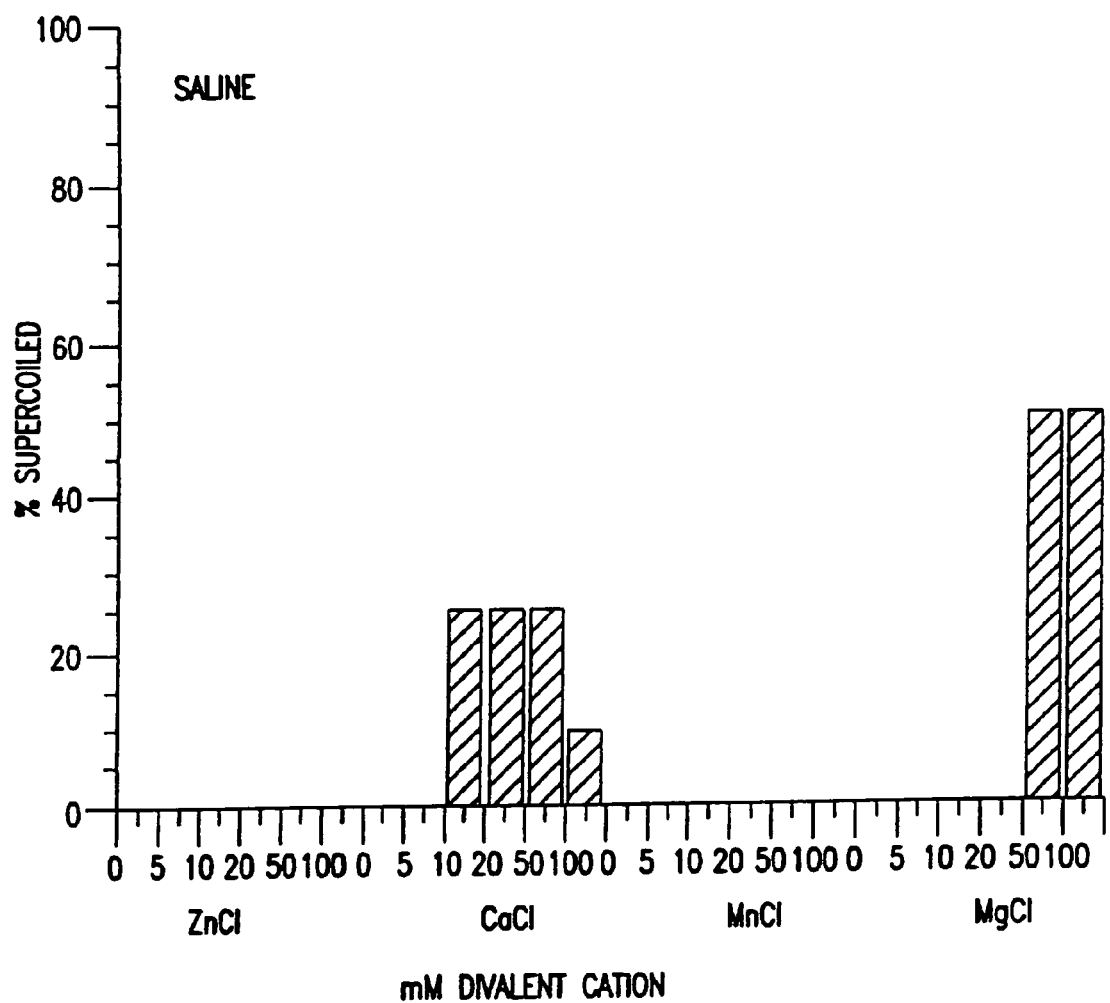

To examine the effect of divalent cations on DNA stability, plasmid DNA was formulated in either TE, phosphate buffered saline (PBS) or saline (0.9% NaCl) in the presence of $ZnCl_2$, $CaCl_2$, $MnCl_2$ or $MgCl_2$. The DNA solutions (100 mcg/mL) were incubated at 60° C. for 48 hours and analyzed by agarose gel electrophoresis. The results (FIGS. 5A, 5B and 5C) indicated that zinc ions did not improve DNA stability. However, the effect of calcium ions was variable. In TE and saline, calcium ions improved stability, while in PBS calcium ions did not increase stability. Manganese ions improved the stability in TE, but only at low concentrations. In PBS and saline, manganese ions did not improve stability. Magnesium ions increased DNA stability in all three formulations, but only at high concentrations in saline.

EXAMPLE 11

Effect of buffer type and pH on DNA stability—Historically, plasmid DNA has been stored in TE buffer (10 mM Tris, 1 mM EDTA, pH 8.0) with routine molecular biology manipulations being carried out in saline and distilled water. Consequently, we deemed it necessary to examine and define an appropriate buffer in which to both store plasmid DNA and manipulate it for future formulation experiments. As an initial study, DNA was incorporated into different buffers at various pH values, and stored at different temperatures. Plasmid DNA was formulated at 500 mcg/mL in PBS at pH 4.5, 7.2 and 9.0, TE at pH 8.0 and 10, distilled water (pH 6.0). saline (pH 6.0) and TFA (trifluoroacetic acid; 0.1%) at pH 2.0. Samples were stored at 4° and 24° C. then analyzed at 1, 4 and 12 week intervals by agarose gel electrophoresis.

TABLE 4

| Buffer | 1 Week | | 4 Week | | 12 Week | |
|---|---|---|---|---|---|---|
| | 4 C. | 24 C. | 4 C. | 24 C. | 4 C. | 24 C. |
| PBS, pH 9.0 | + | + | + | + | + | + |
| PBS, pH 7.2 | + | + | + | + | + | + |
| PBS, pH 4.5 | + | + | + | + | + | − |
| TE, pH 10 | + | + | + | + | + | + |
| TE, pH 8.0 | + | + | + | + | + | + |
| deionized $H_2O$ | + | + | + | +/− | +/− | − |
| TFA (0.1%) | +/− | − | − | − | − | − |
| saline | + | + | + | + | + | − |

Figure 6:
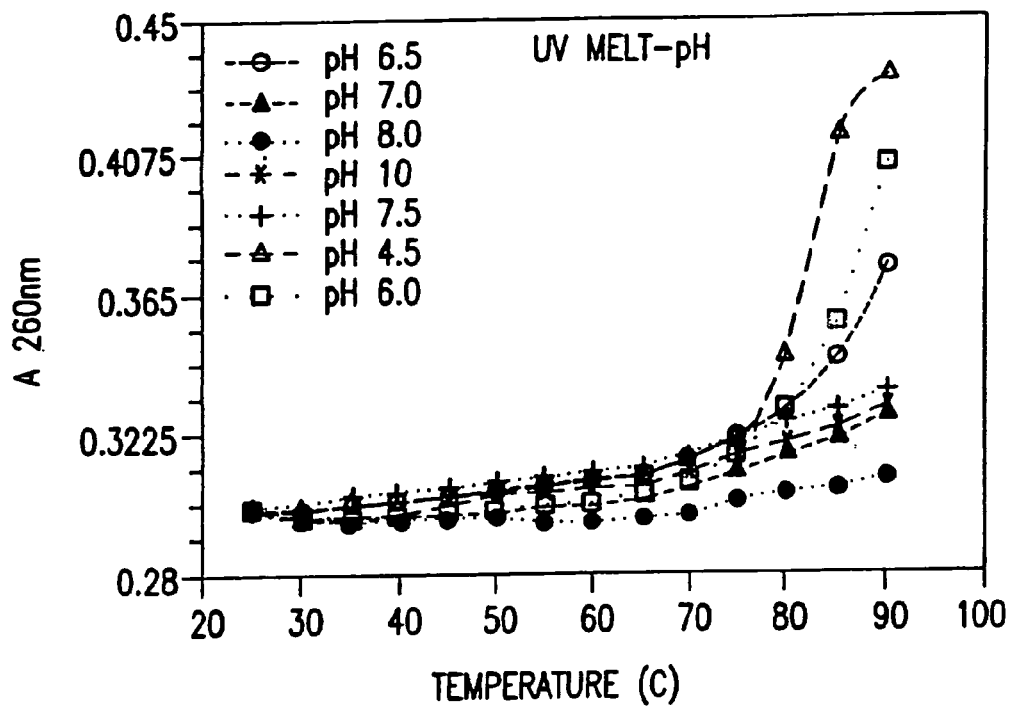
FIG. 6 shows the UV-melting curve of DNA over the pH range 4.5-10. The samples contained 20 mcg/mL plasmid in the following pH buffers: (a) citrate pH 4.5, (b) phosphate pH 6.0, (c) phosphate pH 6.5, (d) phosphate pH 7.0, (e) phosphate pH 7.5, (f) phosphate pH 8.0, (g) borate pH 10.

Table 4 shows the conformational stability of DNA plasmid stored at various pH's. Samples were analyzed by agarose gel electrophoresis; (+) supercoiled, (+/−) supercoiled/open circle, (−) mainly open circle (nicked plasmid). These data show that at low pH (2.0-4.5) DNA is rapidly degraded while at high pH (7.2-9.0) there is little degradation. For example, plasmid DNA stored in both TE and PBS at pH values from 7 to 10, was stable up to 12 weeks at 4° C. To further investigate this pH effect on the conformational stability of DNA plasmid, a UV melting curve was generated over the pH range of 4.5-10 (FIG. 6). This technique allows one to determine the relative stability of DNA at various pHs by measuring the melting point transition (Tm), which occurs as a result of base pair unpairing leading to increased absorbance at 260 nm. The results show that as the pH decreases the absorbance of the DNA, at 260 nm, increases at a lower temperature, thus a lower Tm. This indicates that double stranded DNA is less ordered at lower pHs, and that the unpaired regions of the molecule are more susceptible to breakage at lower pH. One other point to emphasize is that the plasmid DNA was quite resistant to heat denaturation under these conditions. Since heating to 90° C. did not cause complete denaturation of double stranded DNA, a precise Tm could not be determined.

Figure 7A:
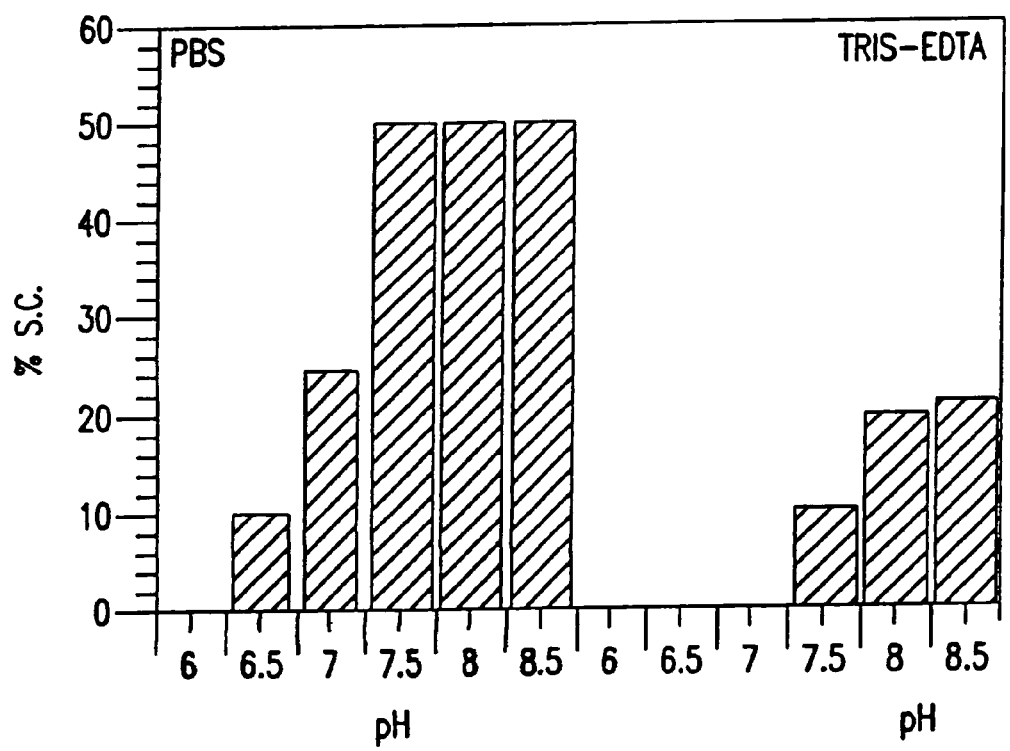
FIG. 7A shows the conformational stability of plasmid DNA in PBS and TE (10 mM Tris-Cl, 1 mM EDTA) buffered over the pH range 6.0 to 8.5. Samples were incubated at 100 mcg/mL for 48 hours at 60° C. then analyzed for degradation by electrophoresis. At time zero samples contained 90% supercoiled DNA.

To quickly explore storage conditions best suited for long term DNA storage, accelerated stability studies were established in which samples were stored at 60° C. for 48 hours and then analyzed by agarose gel electrophoresis. Previous results (Table 1) indicate that storage below pH 6.0 is problematic to DNA stability and either salt or EDTA (or both) may be necessary to stabilize it toward conformational degradation. Thus two buffers, PBS and TE (Tris-EDTA), were analyzed for their ability to stabilize plasmid in the pH range of 6.0-8.5. Plasmid DNA samples were formulated at 100 mcg/mL in the appropriate buffer. Starting material contained 90% of the supercoiled species. The results are shown in FIG. 7A. After incubation at 60° C. for 48 hours, samples stored in TE at pH 7.5-8.5 had 10-25% supercoiled plasmid remaining while those formulated in PBS (pH 7.5-8.5) contained 50% supercoiled plasmid. Furthermore, TE had no apparent stabilizing effect on the DNA at pH 6.5-7.0, while PBS did show a slight stabilizing effect in the same pH range. Neither buffer prevented degradation at pH 6.0.

The results from accelerated studies have indicated that both pH and salt are important parameters to optimize, in order to stabilize DNA during storage. These preliminary results suggested that PBS is a better stabilizer than TE. However, it was not clear whether the stabilizing effect of PBS was due to the presence of phosphate ions, or due to the presence of NaCl. Furthermore, the question of whether a metal ion chelator would stabilize DNA needed to be more adequately addressed. To answer these questions an accelerated stability study (60° C., 48 hrs, 100 mcg/mL DNA) was implemented in which PBS was supplemented with EDTA or additional phosphate, and TE was supplemented with NaCl or phosphate. The results shown in Table 3 indicate that the addition of EDTA or phosphate to PBS did not enhance the stability of DNA to degradation. However, the addition of 150 mM NaCl to TE buffer increased the stability of DNA when compared to non supplemented TE. These results suggest that the stabilizing effect of PBS over TE was due to the presence of 150 mM NaCl in the PBS.

TABLE 5

| Formulation | % supercoiled DNA remaining |
| --- | --- |
| PBS (pH 7.2) | 50 |
| PBS + 1 mM EDTA | 50 |
| PBS + 20 mM sodium phosphate | 50 |
| PBS + 100 mM sodium phosphate | 50 |
| PBS (pH 6.0) | 0 |
| PBS (pH 10.0) | 50 |
| TE + 20 mM sodium phosphate | 10 |
| TE | 10 |
| Saline (pH 8.0) | 0 |
| TE + 150 mM NaCl | 50 |
| PBS + 10 mM EDTA | 50 |

Figure 8A:
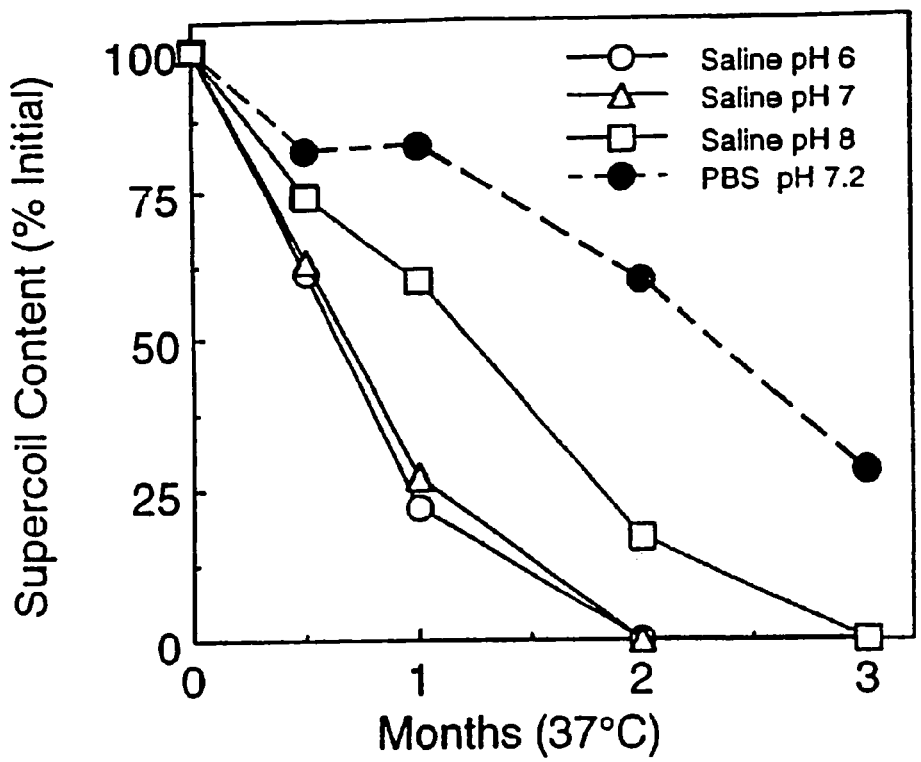
FIG. 8A and FIG. 8B show the effect of PBS vs. saline (0.9% w/v NaCl) formulation on the supercoil content of Influenza DNA (HA-Georgia/93) vaccine during storage at 25° C. (Panel B) and 37° C. (Panel A). DNA plasmid solutions were prepared at 2 mcg/mL. Supercoil content of plasmid was determined by agarose gel electrophoresis.
Figure 8B:
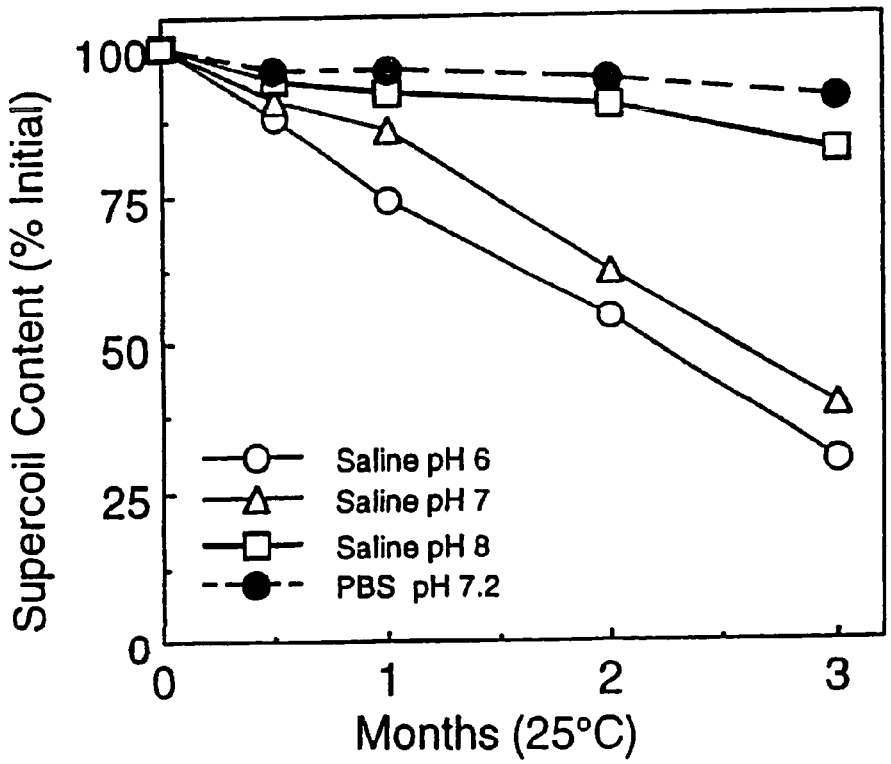

Table 5 shows the conformational stability of plasmid DNA at 60° C., for 48 hours in various buffers. At time zero, samples contained 90% supercoiled DNA. Since the presence of NaCl in the PBS appeared to be the reason for improved DNA stability, compared to TE, another study was initiated to compare saline to PBS. For these experiments, plasmid DNA (chromatographically pure) was directly formulated at high concentration (2.0-2.5 mg/mL) in 0.9% NaCl. Probe stability studies using this DNA were performed with a low concentration of plasmid (2 mcg/mL) formulated in either a PBS buffer (pH 7.2) or 0.9% NaCl adjusted to pH 6, 7, and 8. The plasmid's supercoiled DNA content was monitored by agarose gel electrophoreses over three months at 25° and 37° C. As shown in FIG. 8A (37° C.) and 8B (37° C.), when the initial pH of saline formulated material is decreased, the rate of loss of supercoiled plasmid DNA increased. The

TABLE 6

Table 6: Summary of stability probes 3–9; to examine the effect of buffer ions and pH on the stability of Influenza DNA vaccine, HA (Georgia/93) during storage at 37° C. Percent of initial supercoiled DNA remaining was determined by agarose gel electrophoresis.

Percent of initial supercoiled DNA remaining after three months at 37° C.

| Probe # | Formulation* | [DNA] mcg/mL | 3 months, 37° C. |
| --- | --- | --- | --- |
| 3 | control | 20 | 36 |
| 3 | PBS, pH 7.8 | 100 | 63 |
| 4 | control | 20 | 0 |
| 4 | control | 100 | 0 |
| 4 | saline (0.9% (w/v) NaCl) + 10 mM sodium succinate, pH 7.2 | 20 | 36 |
| 5 | Control | 20 | 57 |
| 5 | saline + 10 mM sodium succinate, pH 7.2 | 20 | 64 |
| 6 | control | 20 | 55 |
| 6 | saline + 10 mM sodium bicarbonate, pH 7.2 | 20 | 80 |
| 7 | control | 2 | 29 |
| 8 | PBS, pH 6.0 | 20 | 0 |
| 8 | control | 20 | 37 |
| 8 | PBS, pH 8.0 | 20 | 0 |
| 9 | control | 2 | 31 |
| 9 | PBS, pH 8.0 | 2 | 36 |

*The DNA in all probes was formulated in the control formulation (PBS, pH 7.2) unless noted otherwise.

saline formulated material did not maintain pH over time. For example, after 2 months at 37° C. the saline formulated plasmid (initial pH of 6, 7 and 8) had a pH value of 5.9, 6.0 and 6.3, respectively. In contrast, the PBS formulated material maintained its pH value (7.1-7.2) over the same incubation period. The PBS formulated material also contained the highest percentage of supercoiled content with a more or less consistent level of supercoiled plasmid after 3 months at 25° C.

As the supercoiled content of plasmid decreased, a concomitant increase in the open circle form of the plasmid was observed by agarose gel electrophoresis. After longer periods of time, the open circular form converts to linear plasmid DNA. For example, after 3 months at 37° C., the pH 6 and pH 7 saline formulated material (originally containing 92 to 93% supercoiled plasmid DNA) contains 0% initial supercoiled, ~36% open circle and ~64% linear plasmid DNA.

To determine if the trends observed with saline versus PBS formulated probe material under accelerated conditions corresponds to material under nonaccelerated storage conditions, a stability study was setup. Plasmid DNA was formulated at low, intermediate and high doses in both saline (2, 20 and 2200 mcg/mL plasmid) and PBS (2, 20, 1000 mcg/mL plasmid). Both solution pH and supercoiled content were monitored during storage at 2-8° C. and −70° C. As shown in Table 1, the PBS formulated material was more consistent in terms of pH and plasmid supercoiled DNA content during storage for up to 3 months.

To examine the effects of different buffer ions and pH on DNA stability several lots of plasmid DNA were formulated with several different buffer/pH combinations and incubated for 3 months at 37° C. Following the incubation, the percent of initial supercoiled DNA content was determined by agarose gel electrophoresis. The results shown in Table 6 indicate that the stability is highly variable from lot to lot of DNA, that acidic pH is detrimental to stability and that formulations having a higher DNA concentration were more stable. The lot to lot variability may have been due to varying trace metal

TABLE 7

Table 7: Comparison of the effects of different buffer ions and pH on DNA stability, at 5, 24 and 37° C. Percent of initial supercoiled DNA remaining was determined by agarose gel electrophoresis.

DNA = Influenza DNA vaccine
Volume & concentration = 0.8 mL/vial at 20 mcg/mL
Temperature = 5, 24 and 37° C.
container = 3.0 mL glass vials + Teflon stoppers
Time 0 = 6 Feb 96
7 different buffers tested, conditions A–G shown below.
A = 20 mM Sodium Succinate, 150 mM NaCl, pH 6.2
B = 20 mM Maleic acid - disodium salt, 150 mM NaCl, pH 6.2
C = Histidine, 150 mM NaCl, pH 6.2
D = 20 mM Sodium Phospate, 150 mM NaCl, pH 6.2
E = 20 mM Sodium Phosphate, 150 mM NaCl, pH 7.5
F = 20 mM Tris, pH 7.5, 150 mM NaCl
G = 20 mM Tricine, pH 7.5, 150 mM NaCl Percent of initial supercoiled DNA remaining.

| | | 1 month | | |
| --- | --- | --- | --- | --- |
| Condition | Initial % SC | 5° C. | 24° C. | 37° C. |
| A | 97 | 90 | 86 | 43 |
| B | 97 | 94 | 89 | 40 |
| C | 95 | 92 | 47 | 0 |
| D | 94 | 89 | 66 | 16 |
| E | 94 | 93 | 63 | 32 |
| F | 95 | 94 | 98 | 58 |
| G | 96 | 94 | 94 | 79 | content. The results of Table 6 suggested that certain buffer/pH combinations would require further investigation. The most promising combinations identified by this study were sodium bicarbonate (pH 7.2), PBS (pH 7.2-8.0) and sodium succinate (pH 7.2).

Figure 7B:
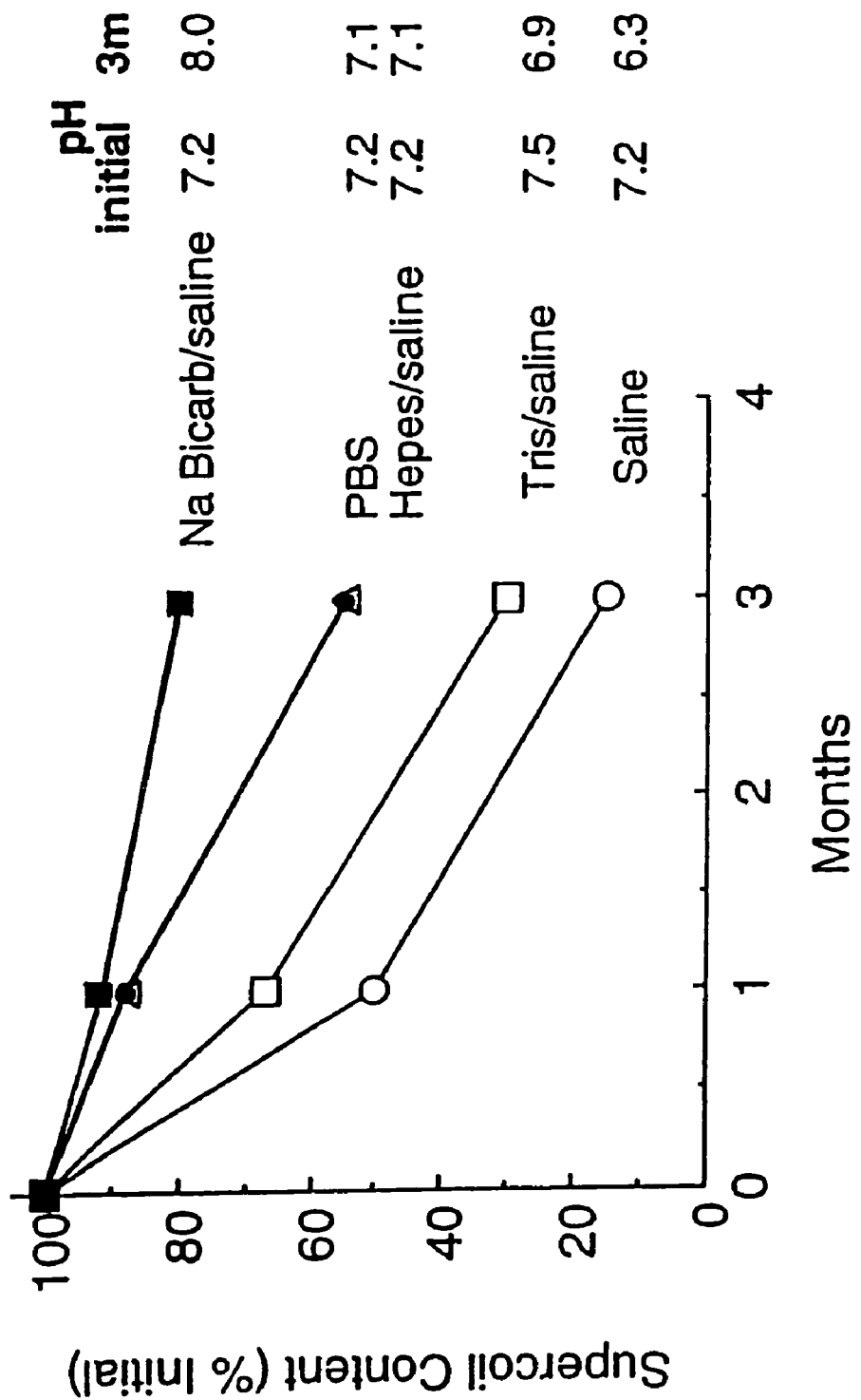
FIG. 7B shows the effect of buffer type and solution pH on the supercoil content (DNA stability) of Influenza DNA vaccine during storage at 37° C. DNA plasmid solutions were prepared at 20 mcg/mL. DNA was formulated in saline alone, or in saline with a Tris, Hepes, Phosphate or Sodium Bicarbonate buffer. Buffer pH was measured at time zero (room temperature) and at 3 months (37° C.). Supercoil content of plasmid was determined by agarose gel electrophoresis.

To address the question of whether the addition of a buffer to saline improves the stability of the DNA, a study was initiated to compare the effects of saline alone, with saline in combination with four different buffers. For this study the DNA was formulated at 20 mcg/mL and incubated at 37° C. for 3 months. The percent of initial supercoiled DNA was determined by agarose gel electrophoresis. The results, shown in FIG. 7B, clearly indicate that the addition of either a sodium bicarbonate, phosphate, Hepes or Tris buffer improved the stability of the DNA, compared to saline alone. The data also suggested that there are major differences in the stabilizing effects of the buffer ions. Furthermore, the results suggest that the DNA stability is related to the maintenance of pH. As seen in FIG. 7B, the Tris/saline combination and particularly saline alone had the least stabilizing effect on the DNA, and did not maintain a constant pH over the 3 months of incubation. Therefore, one of the functions of the buffer, with respect stabilizing DNA, is to maintain the pH in the neutral to slightly basic range. Although another function of the buffer is to stabilize the DNA against degradative pathways, these results indicate that different buffers have different capacities to stabilize DNA, and further work was needed to identify the particular buffers having the greatest stabilizing effect. In that regard, these data were the first indication that sodium bicarbonate stabilizes DNA during storage.

The effects of additional buffer/pH combinations on DNA stability are shown in Table 7. In this study the DNA was formulated in various buffer/pH combinations and incubated for one month at 5°, 24° and 37° C. Following the incubation the percent of initial supercoiled DNA was determined by agarose gel electrophoresis. The results indicated that the best buffer/pH combination was Tricine at pH 7.5. However, several other combinations provided stability above that of sodium phosphate at pH 7.5, including sodium succinate (pH 6.2), sodium malate (pH 6.2) and Tris (pH 7.5). Additional studies designed to compare the most promising buffer/pH combinations again are in progress at 4°, 25°, 37° and 50° C.

To determine if the buffer ions in the DNA vaccine formulation would affect the immune response, the induced immune response to Influenza DNA vaccine, HA (Georgia/93) was measured at several doses of DNA by measuring HI titer. The results shown in FIG. 9 indicate that the immune response to the DNA vaccine formulated in PBS was superior to the response observed for DNA formulated in saline.

Figure 13:
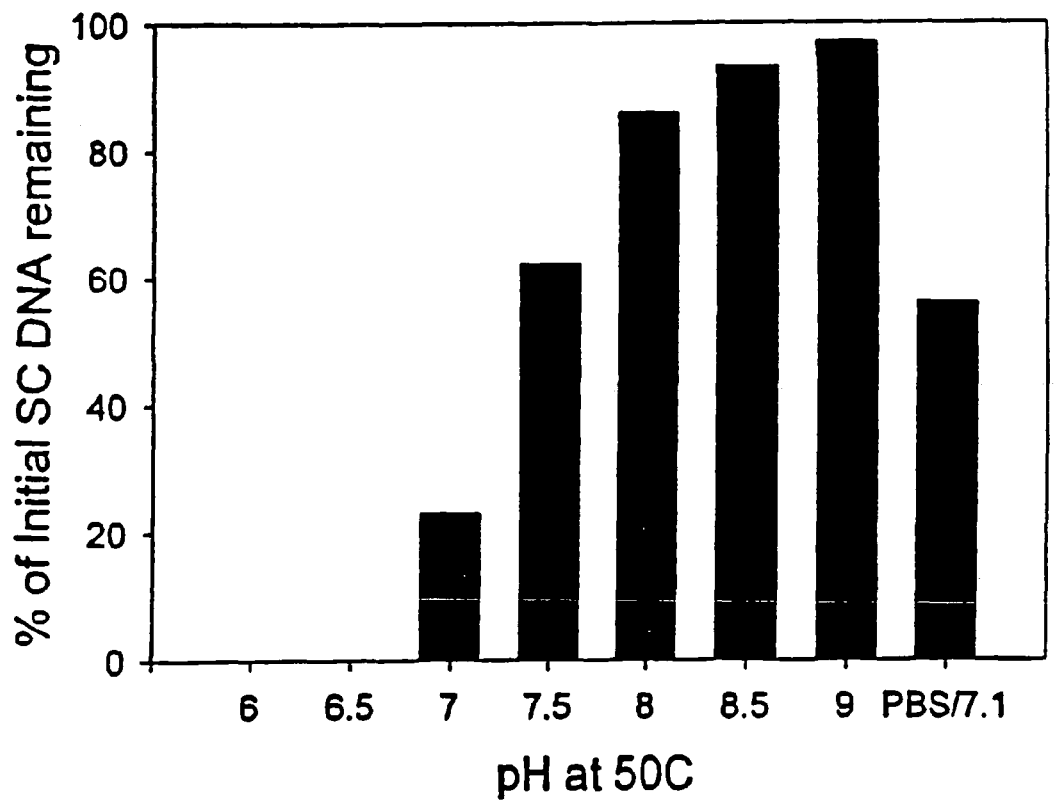
FIG. 13 shows the effect of pH on DNA stability (as a percentage of initial supercoiled plasmid DNA remaining) after two weeks at 50° C. in 20 mM Bis-Tris-Propane, 150 mM NaCl. Control is DNA in PBS at pH 7.1.

To determine the effects of pH on DNA stability over a broad range of pH, a stability experiment was performed in 20 mM Bis-Tris-Propane containing 150 mM NaCl, from pH 6.0 to 9.0. The results of the stability test are shown in FIG. 13, after 2 weeks of incubation at 50° C. (2 mcg/mL DNA). The results clearly indicate that the pH of the formulation greatly affects the stability of the DNA, and that the optimum pH is $\geq 8.5$. Since the stability of the DNA in the PBS control, at pH 7.1, was nearly equal to that of the DNA in Bis-Tris-Propane at pH 7.5, the results suggest that the buffer type also influences the stability of the DNA at a given pH.

Figure 14:
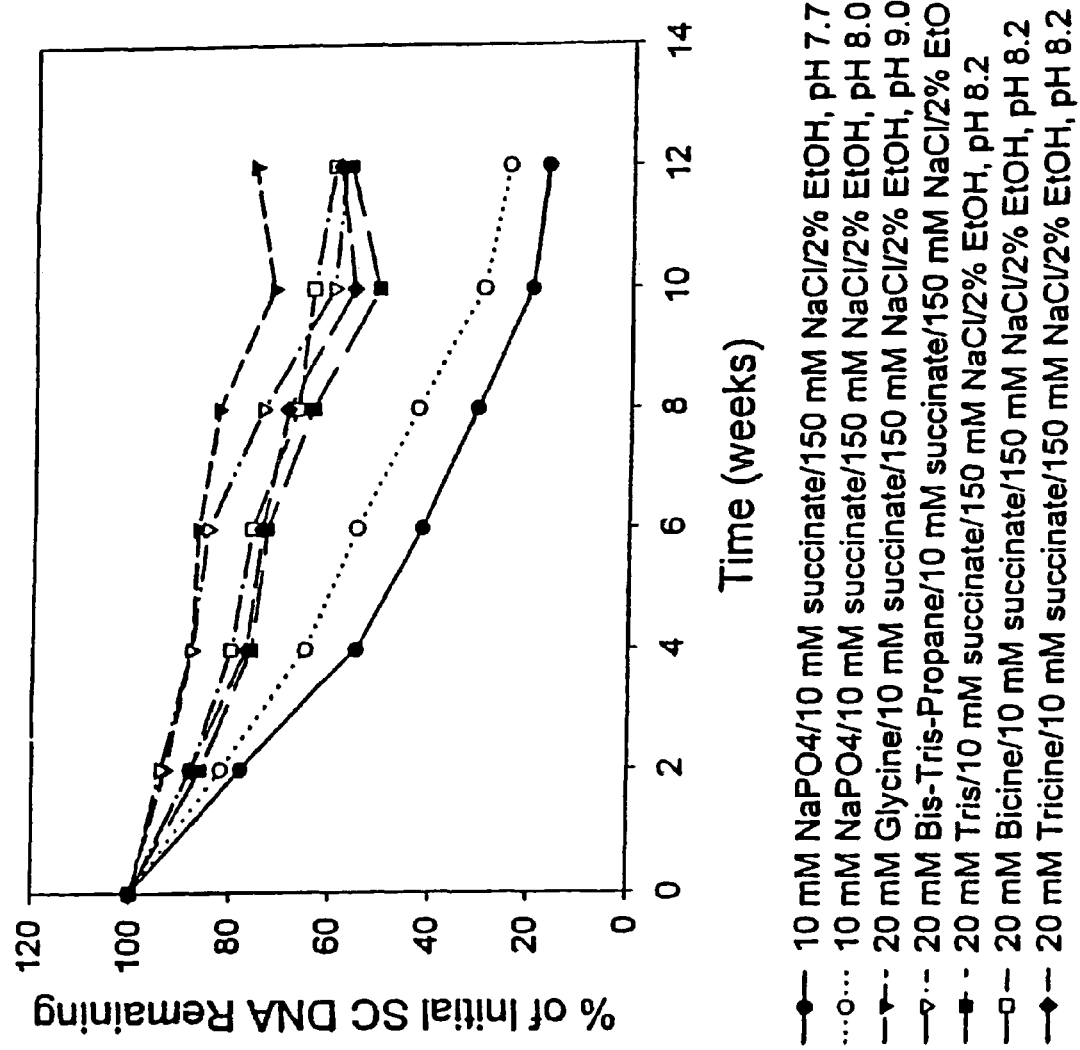
FIG. 14 shows the effect of buffer type and pH on DNA stability at 50° C. at a DNA concentration of 20 mcg/mL. DNA stability is measured as % of initial supercoiled (SC) DNA remaining.

To address the effects of buffer type on DNA stability a stability experiment was performed with DNA at 20 mcg/mL in seven different formulations. Since previous experiments had shown that the purity of the buffer influenced DNA stability, 10 mM succinate and 2% ethanol were added to each formulation to inhibit free radical oxidation of the DNA (data presented in examples 14 and 15 show that succinate and ethanol each enhance DNA stability). The results (FIG. 14) indicate that the formulation that provided the highest DNA stability was also at the highest pH used (pH 9). However, some buffer effects were also noted. The largest buffer effect was between glycine and Bis-Tris-Propane, where the data indicates that the glycine formulation at pH 9 was significantly superior to the Bis-Tris-Propane formulation at the same pH. In contrast, the Tris, Bicine and Tricine buffers at pH 8.2, provided nearly identical DNA stability out to 12 weeks. The data also indicate that the two phosphate formulations (at pH 7.7 and 8.0) provided the lowest DNA stability, but they were also the lowest pH formulations tested. Due to the low buffering capacity of phosphate buffers above pH 8.0, the phosphate formulations were limited to pH values at or below 8.0. These results suggest that once free radical oxidation of the DNA is controlled by the addition of chelators (see example 15 for data showing which chelators enhance DNA stability and under what conditions) and free radical scavengers (see example 14 for data showing the enhancement of DNA stability by ethanol) that the stability of the DNA is controlled primarily by the pH of the formulation.

EXAMPLE 12

Figure 10:
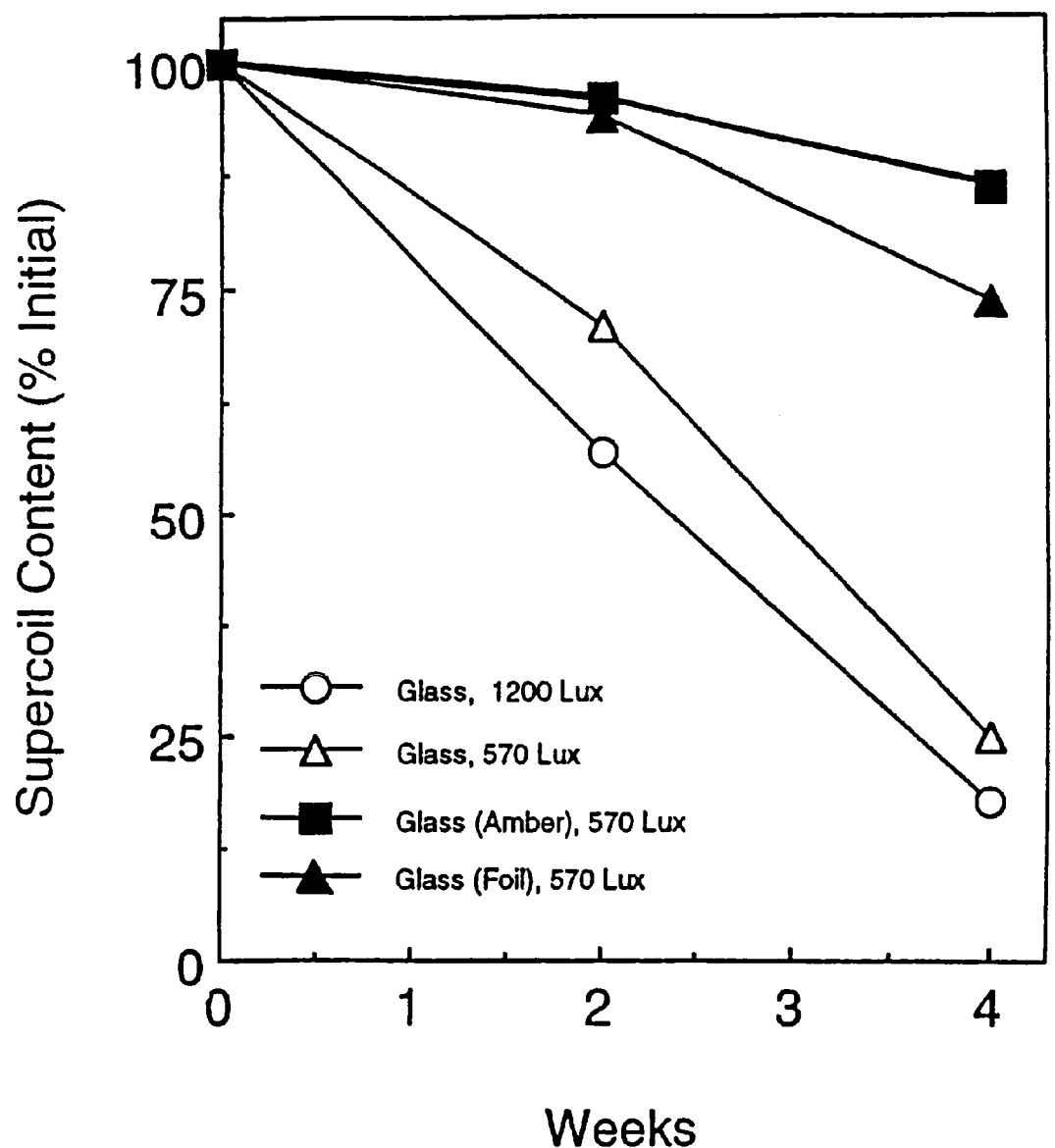
FIG. 10 shows the effect of exposure to light on the supercoil content of Influenza DNA vaccine during storage at 25° C. DNA plasmid solutions were prepared at 100 mcg/mL DNA in saline. Supercoil content of plasmid was determined by agarose gel electrophoresis.

Effect of light on DNA stability—Initially, the light sensitivity of the material was evaluated to determine if special handling procedures would be required or if amber vials would be necessary for long term storage. The results of an experiment to measure light sensitivity (FIG. 10) indicated that exposure of 100 mcg/mL plasmid DNA in saline to light accelerated the conversion of supercoiled DNA plasmid to the open circular form, as measured by agarose gel electrophoresis. The conversion to the open circular form was much more pronounced when the DNA was stored in clear glass vials as opposed to amber vials, as expected. Although a 2-4 week exposure to light caused significant degradation, no significant losses were observed over an eight hour day. Since amber vials have the potential to leach trace metal ions over time, which catalyze free radical oxidation of the DNA (see below), a packaging solution to the light sensitivity of the plasmid is required for long term storage.

Figure 15:
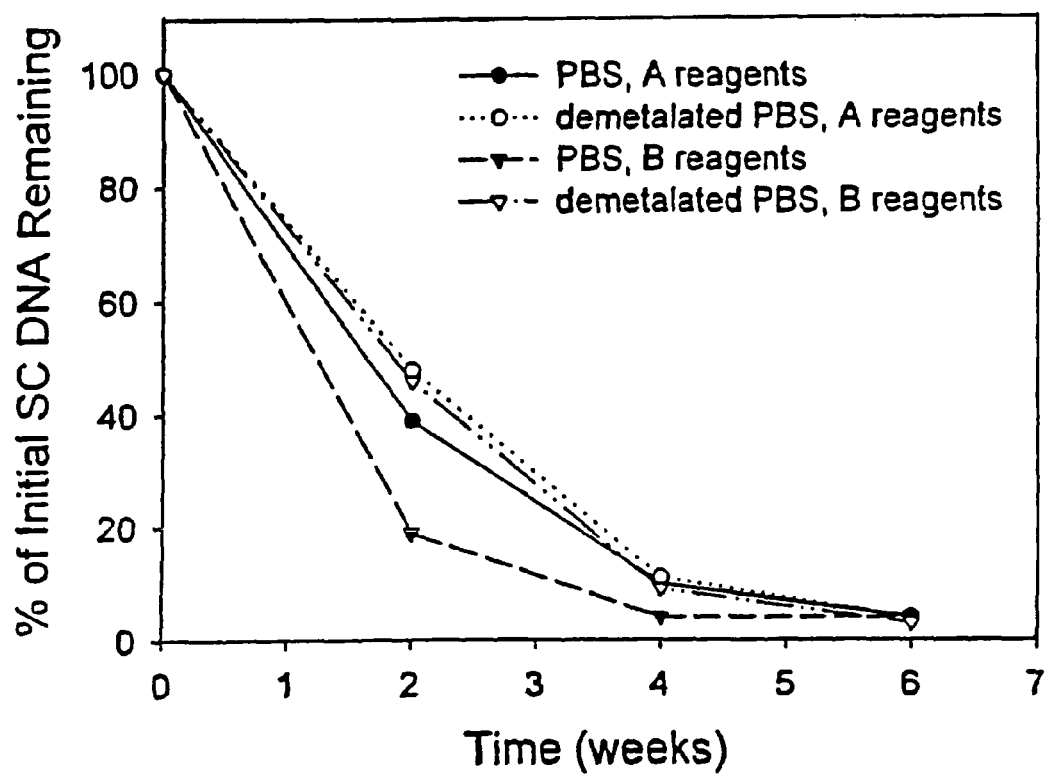
FIG. 15 shows the effect of demetalation on DNA stability at 50° C., pH 7.2 in 2 mcg/mL of DNA. DNA stability is measured as % of initial supercoiled (SC) DNA remaining.
Figure 16:
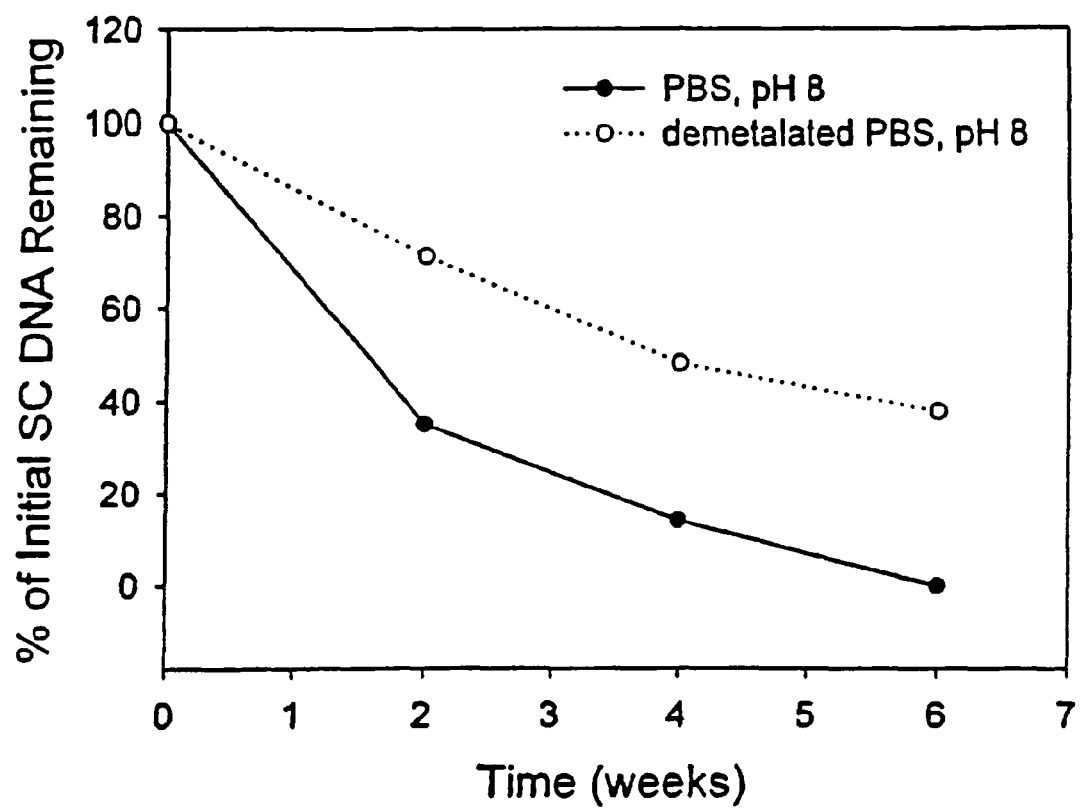
FIG. 16 shows the effect of demetalation on DNA stability at 50° C., pH 8.0 in 2 mcg/mL of DNA. DNA stability is measured as % of initial supercoiled (SC) DNA remaining.
Figure 27:
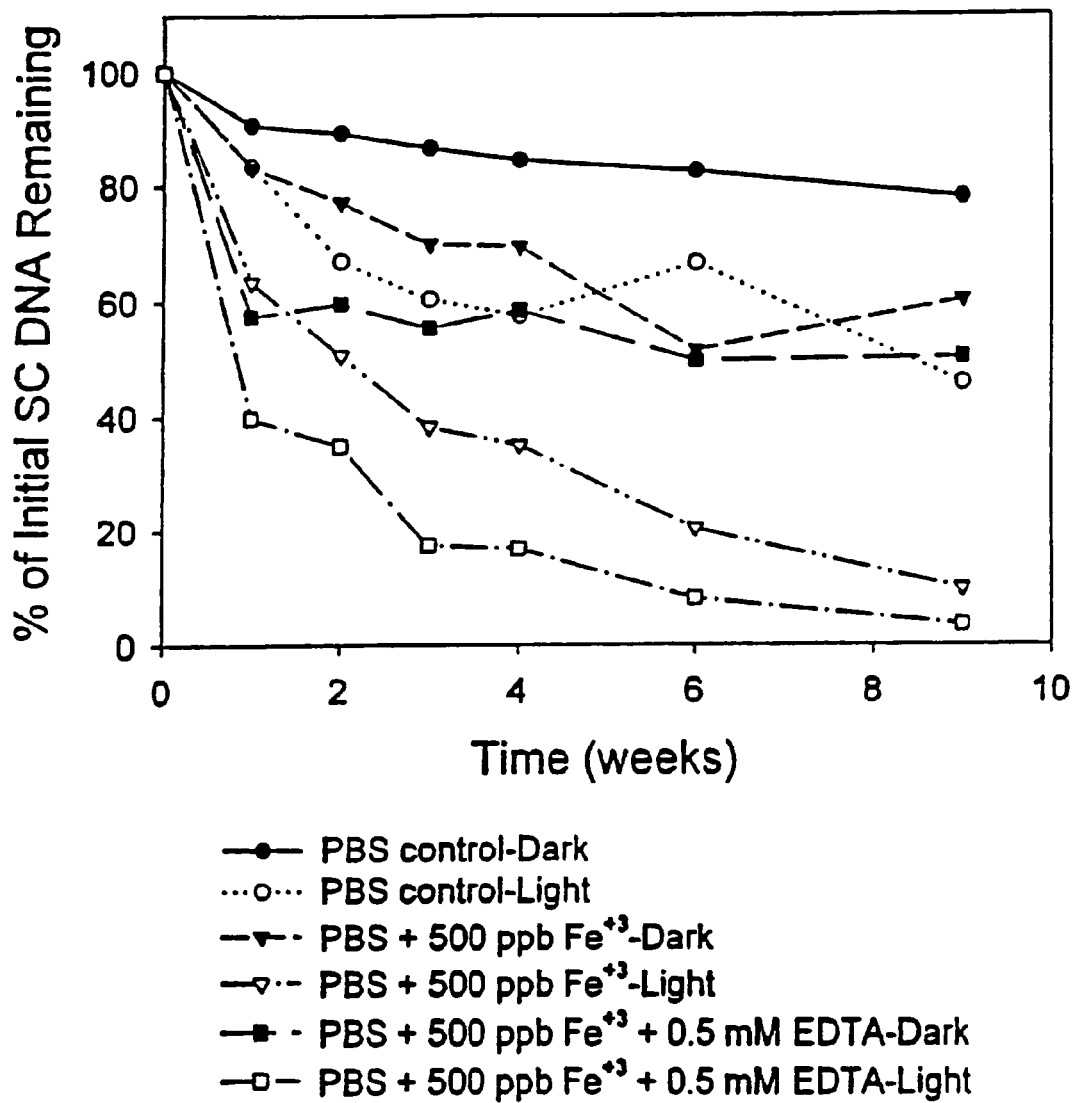
FIG. 27 shows the effect of light on DNA stability in formulations containing iron and EDTA. DNA stability is measured as % of initial supercoiled (SC) DNA remaining.
Figure 28:
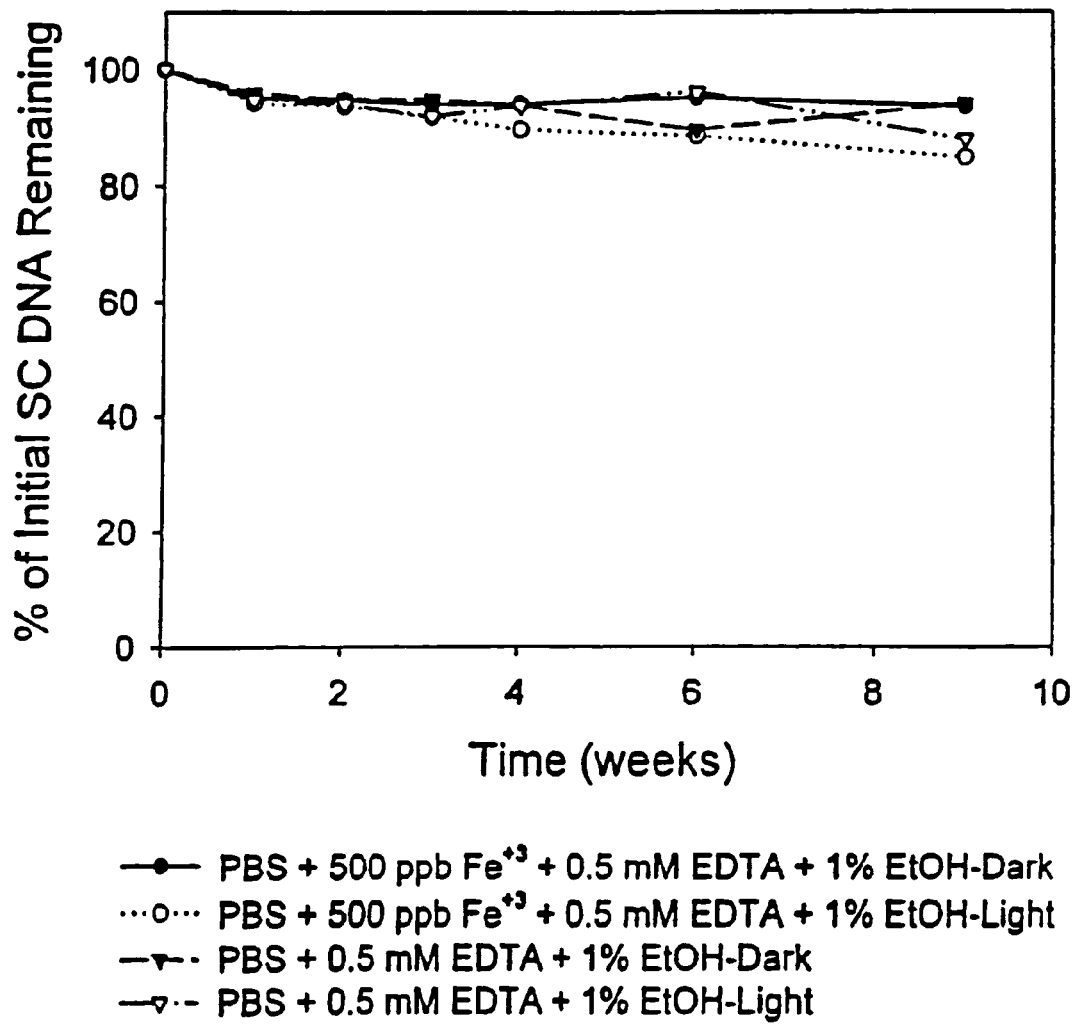
FIG. 28 shows the effect of light on DNA stability in formulations containing iron, EDTA and ethanol. DNA stability is measured as % of initial supercoiled (SC) DNA remaining.

To determine the effects of light on DNA stability in formulations containing $Fe^{+3}$, metal ion chelators and free radical scavengers a stability study was performed over 9 weeks at 30° C. in the presence and absence of visible light (fluorescent light at 2000 Lux). The DNA concentration was 20 mcg/mL and the formulation buffer was 10 mM sodium phosphate containing 150 mM NaCl at pH 8.0. The results, shown in FIGS. 27 and 28 below, indicated that light decreased the stability of the DNA significantly in the PBS control and in PBS containing 500 ppb $Fe^{+3}$ or PBS containing 0.5 mM EDTA and 500 ppb $Fe^{+3}$. The results also indicated that the presence of 0.5 mM EDTA did not diminish the detrimental effects of light on DNA stability in the presence of 500 ppb $Fe^{+3}$. The results in FIG. 16 show the effects of light on DNA stability in formulations containing EDTA and ethanol. The results indicated that the presence of EDTA and ethanol greatly stabilized the DNA, in the light and dark samples, compared to the control formulation in FIG. 15. The results also indicated that the detrimental effects of light on DNA stability were greatly diminished by the presence of EDTA and ethanol, even in formulations containing 500 ppb Fe+3. Therefore, the results suggest that DNA vaccine formulations containing EDTA and ethanol would be much less sensitive to the detrimental effects of light and trace metal ions than formulations lacking either of these two stabilizers.

EXAMPLE 13

Effect of demetalation and deoxygenation on DNA stability: Method of demetalating PBS. —To prepare demetalated PBS, 20.0 grams of Chelex 100 resin (BIO-RAD Laboratories) was washed with 400 mL of USP water using vacuum filtration over a cellulose acetate membrane (0.22 micrometer pore size). The washed resin was added to approximately 1 liter of PBS and stirred slowly overnight at 2-8° C. by placing a magnetic stir bar in the one liter bottle containing the slurry and using a magnetic stirrer set to its slowest stir rate. The following day the resin was removed by vacuum sterile filtration using a cellulose acetate membrane (Corning, 0.22 micron pore size). Care was taken to pre-wash the membrane with two 10 mL applications of the demetalated slurry prior to collecting the final filtered product. This step was performed to ensure that any potential leaching of metal ions from the membrane would not contaminate the demetalated product.

Method of demetalating Plasmid DNA—To demetalate solutions containing plasmid DNA, the DNA was diluted with demetalated PBS to a final volume of approximately 2 mL. The DNA was then applied to a 1 mL Chelex 100 column, previously equilibrated by washing the column with 5 mL of demetalated PBS. The demetalated DNA in the effluent was collected, followed by the addition of 6 mL of additional demetalated PBS to wash the remaining DNA off the column. The entire effluent was then diluted to a final volume of 12.0 mL with demetalated PBS and sterile filtered with a Millipore Millex-GV25 mm syringe filter (0.22 micron pore size). Our initial experiments involved the demetalation of only 48 micrograms of DNA with a 1 mL column, however, the capacity of the Chelex 100 resin will allow much larger quantities of DNA to be demetalated using the same size column.

Method of deoxygenating PBS, and demetalated PBS. —To prepare deoxygenated (degassed) PBS or deoxygenated and demetalated PBS, 250 mL of the buffer was heated to boiling in a Pyrex bottle. The solution was then allowed to cool to room temperature under continuous helium sparging, and capped.

Method of preparing deoxygenated, or deoxygenated and demetalated plasmid DNA—To prepare deoxygenated DNA solutions for stability studies, Influenza vaccine DNA, HA (Georgia/93), was diluted into sterile deoxygenated PBS. The original stock Influenza vaccine DNA was not deoxygenated because it was diluted over 1000-fold (from 2.55 mg/mL to 2.0 mcg/mL). The deoxygenated DNA solution was then placed in sterile glass vials, and capped after flooding the headspace with filtered nitrogen. To prepare deoxygenated and demetalated DNA solutions for stability studies, Influenza vaccine DNA, HA (Georgia/93), was first diluted into demetalated and deoxygenated PBS. This solution was then applied to a 1 mL Chelex 100 column to demetalate the DNA. The solution was then diluted with additional deoxygenated and demetalated PBS, filter sterilized and sparged with helium just prior to filling vials. The headspace of each vial was flooded with filtered nitrogen before capping.

Table 6 contains the results of an experiment to determine the stability of plasmid DNA in PBS (pH 7.2) and demetalated PBS. The results indicate an improvement of DNA stability in demetalated PBS over the control condition, and suggest that the stability of a DNA vaccine would be greatly enhanced if stored in a demetalated buffer. Furthermore, DNA stored in demetalated PBS was far more stable than would be predicted using the published rate constants for depurination and β-elimination. Depurination and β-elimination are two sequential chemical reactions in the process of breaking the phosphodiester backbone of the DNA, that occur in aqueous solution. In the first step, [H+] catalyzes the loss of the purine bases from DNA, leaving behind an apurinic site (AP site). In the second step of the hydrolysis, [OH−] catalyzes a β-elimination reaction, which breaks the bond between the oxygen atom bonded to the 3' carbon of the deoxyribose, and the 3' carbon atom. Because depurination and β-elimination are natural processes that cannot be completely prevented from occurring, in aqueous

TABLE 8

Table 8: Effects of demetalation, deoxygenation and p-hydroxybenzyl alcohol on DNA stability. Percent of initial supercoiled DNA remaining was determined by agarose gel electrophoresis.

| | | % of Initial Supercoiled DNA Remaining | | | | | |
|---|---|---|---|---|---|---|---|
| Condition | 25-Jan Initial % SC | 26-Jan 1 day | 27-Jan 2 days | 29-Jan 4 days | 8-Feb 14 days | 22-Feb 28 days | 7-Mar 42 days |
| C1 | 90 | 97 | 93 | 82 | 45 | 0 | 0 |
| C2 | 89 | 98 | 102 | 94 | 90 | 65 | 33 |
| C3 | 89 | 104 | 101 | 94 | 68 | 21 | 4 |
| C4 | 90 | 98 | 102 | 98 | 94 | 20 | 37 |
| C5 | 91 | 90 | 77 | 36 | 0 | 0 | 0 |
| C6 | 92 | 99 | 95 | 82 | 21 | 0 | 0 |
| C7 | 91 | 97 | 92 | 78 | 0 | 0 | 0 |

DNA = Influenza DNA vaccine
Volume & Concentration = 0.8 ml/vial at 2 mcg/mL
Temperature = 50 C.
container = 3.0 ml glass vials + Teflon stoppers
Time 0 = 25 Jan 96
All condtions contained PBS, pH 7.2
C1 = PBS control, pH 7.2
C2 = demetalated PBS, demetalated DNA
C3 = deoxygenated
C4 = demetalated PBS, demetalated DNA, deoxygenated
C5 = +10 mM pHBA (p-hydroxylbenzylalcohol)
C6 = demetalated PBS, demetalated DNA + 10 mM pHBA
C7 = demetalated PBS, demetalated DNA, deoxygenated + 10 mM pHBA solution, one would expect that when all other sources of DNA degradation are eliminated, that the natural rates of depurination and β-elimination would define the stability of the DNA. The published rate constant (k) and activation energy (Ea) for depurination at pH 7.4 (70° C., +10 mM $MgCl_2$) are $4.0 \times 10^{-9}$ $s^{-1}$ and 31 kcal/mol, respectively (see Lindahl et al., 1972, *Biochemistry* 19: 3610-3618). Therefore, at 50° C. the depurination rate in PBS should be approximately $2.3 \times 10^{-10}$ $s^{-1}$ in the presence of magnesium, and $3.3 \times 10^{-10}$ $s^{-1}$ in the absence of magnesium, based on the effects of magnesium at 70° C. The published rate constant (70° C., in the absence of magnesium) and Ea for the β-elimination step are $2.4 \times 10^{-5}$ $s^{-1}$ and 24.5 kcal/mol (see Lindahl et al., 1972, *Biochemistry* 19: 3610-3618). Therefore, at 50° C. the rate constant for the β-elimination step should be approximately $2.6 \times 10^{-6}$ $S^1$. Therefore, the rate of strand break (SB) formation would be equal to [AP sites]$k_2$, where the k1 is the rate constant for depurination, k2 is the rate constant for β-elimination and [AP sites] is the concentration of apurinic sites in the DNA, as shown below.

Plasmid DNA - - - $k_1$ - - - >[AP sites] - - -
$k_2$ - - - >Strand breaks (SB)

Therefore, to determine the rate of strand break formation at any point in time, after a period of incubation at 50° C.
Rate=6,600 purines (for IDV, HA, Georgia/93)×$3.3 \times 10^{-10}$ $s^{-1}$×$k_2$
Rate=$2.2 \times 10^{-6}$ $s^{-1}$×$k_2$
Rate=$2.2 \times 10^{-6}$ $s^{-1}$×$2.6 \times 10^{-6}$ $s^{-1}$
Rate=$5.7 \times 10^{-12}$ $s^{-2}$
Rate of SB formation at any time=$5.7 \times 10^{-12}$ $s^{-2}$×(time in seconds)
Then, the number of SB present at any time t is equal to the integral of $5.7 \times 10^{-12}$ (t) over time from t=0 to t=time Then, the number of SB present at any time $t=\frac{1}{2}(5.7\times10^{-12})$ $t^2$ Therefore, the number of SB present at any time $t=2.85\times10^{-12}(t^2)$ If we use the published rate constants above to determine the number of strand breaks in the Influenza DNA vaccine after 28 days of incubation at 50° C., we obtain 16.7 strand breaks per plasmid. A random distribution of 16.7 strand breaks per plasmid molecule in a population of plasmids would produce a composition completely devoid of any supercoiled DNA. However, the data in Table 6 indicate that in the demetalated sample, 65% of the initial supercoiled DNA remained after 28 days. These data suggest that demetalation greatly reduces the rate of depurination and/or β-elimination, in aqueous solution. It is not known how trace metal ions could affect the depurination or β-elimination reactions to this degree.

The results in Table 8 also indicate that deoxygenation improved DNA stability, presumably by reducing the production of oxygen containing free radicals. The most stable formulation in this study was the demetalated, deoxygenated sample, having 37% of initial supercoiled DNA remaining after 42 days at 50° C.

The results of another study on the effects of demetalation (Table 9) also indicate that demetalation and deoxygenation of the PBS buffer and the DNA greatly improves DNA stability at 50° C., over the non-demetalated PBS control. In order to remove any residual metal ions from the glass vials used for storage, some of the vials were washed with a solution of PBS containing 1 mM EDTA, deionized water and autoclaved before use. A comparison of the DNA stability between washed and unwashed vials indicated that washing the vials did not significantly improve the stability of the DNA, under accelerated conditions. However, washing the vials to reduce the surface metal ion content may improve the long term stability of the DNA vaccine.

To determine if the enhanced stability observed in demetalated PBS requires the demetalation of the plasmid DNA prior to its addition to the demetalated PBS, a study was initiated to determine

TABLE 9

Table 9: Effects of demetalation, deoxygenation and ethanol on DNA stability. Percent of inital supercoiled DNA was determined by agarose gel electrophoresis.

| | % of Initial Supercoiled DNA remaining | | | | | |
| --- | --- | --- | --- | --- | --- | --- |
| Condition | 6-Feb Initial % SC | 13-Feb 7 days | 20-Feb 14 days | 5-Mar 28 days | 19-Mar 42 days | 2-Apr 56 days |
| C1 | 95 | 86 | 59 | 19 | 3 | 0 |
| C2 | 97 | 95 | 85 | 52 | 44 | 14 |
| C3 | 95 | 99 | 86 | 47 | 53 | 9 |
| C4 | 97 | 97 | 92 | 72 | 60 | 33 |
| C5 | 95 | 93 | 89 | 63 | 58 | 29 |
| C6 | 97 | 98 | 93 | 71 | 68 | 42 |

DNA = Influenza DNA vaccine
Volume & Concentration = 0.8 ml/vial at 2 mcg/ml
Temperature = 50 C.
container = 3.0 ml glass vials + Teflon stoppers
Time 0 = 6 Feb 96
All conditions contained PBS, pH 7.2
C1 = PBS control, pH 7.2, regular vials
C2 = demetalated PBS, demetalated DNA, regular vials
C3 = demetalated PBS, demetalated DNA, washed vials
C4 = demetalated PBS, demetalated DNA + 5% ethanol (v/v), washed vials
C5 = demetalated PBS, demetalated DNA, deoxygenated, washed vials
C6 = demetalated PBS, demetalated DNA, deoxygenated + 5% ethanol, washed vials

TABLE 10

Table 10: Effects of partial and complete demetalation, EDTA and ethanol on DNA stability. Percent of initial supercoiled DNA remaining was determined by agarose gel electrophoresis.

| | % of Initial Supercoiled DNA remaining | | | | | |
| --- | --- | --- | --- | --- | --- | --- |
| Condition | 20-Feb Initial % SC | 27-Feb 7 days | 5-Mar 14 days | 19-Mar 28 days | 2-Apr 42 days | 16-Apr 56 days |
| C1 | 95 | 76 | 38 | 15 | | 0 |
| C2 | 95 | 90 | 74 | 55 | | 43 |
| C3 | 95 | 88 | 71 | 49 | | 27 |
| C4 | 94 | 83 | 41 | 14 | | 0 |
| C5 | 96 | 89 | 56 | 25 | | 12 |
| C6 | 96 | 89 | 57 | 29 | | 13 |
| C7 | 94 | 100 | 91 | 78 | | 63 |

DNA = Influenza DNA vaccine
Volume & Concentration = 0.8 ml/vial at 2.0 mcg/ml
Temperature = 50 C.
container = 3 ml vials + Teflon stoppers
Time 0 = 20 Feb 96
All conditions contained PBS, pH 7.2
C1 = PBS control, pH 7.2
C2 = demetalated PBS, demetalated DNA
C3 = demetalated PBS, DNA was not demetalated
C4 = +0.5 mM EDTA
C5 = +5% (v/v) ethanol
C6 = +0.5 mM EDTA + 5% (v/v) ethanol
C7 = demetalated PBS, demetalated DNA + 5% (v/v) ethanol

TABLE 11

Table 11: Effects of removing any residual contaminating nuclease activity, on DNA stability. Percent of initial supercoiled DNA remaining was determined by agarose gel electrophoresis.

DNA = Influenza DNA vaccine
Volume & Concentration = 0.8 ml/vial at 2.0 mcg/ml
Temperature = 50 C.
Container = 3 ml glass vials with Teflon stoppers
Time 0 = 29 Feb 96
All conditions contained PBS, pH 7.2
C1 = PBS control, pH 7.2
C2 = +0.1% (w/v) SDS
C3 = DNA treated with Micropure EZ membrane to remove contaminating enzymes
C4 = DNA treated with 1 mcg of Protease K, 1 HR at 24 C., then Micropure EZ
C5 = one phenol extraction & ethanol precipitation of the DNA, then resuspended the DNA pellet in PBS.

| | % of Initial Supercoiled DNA remaining | | | | | |
| --- | --- | --- | --- | --- | --- | --- |
| Condition | 29-Feb Initial % SC | 7-Mar 7 days | 14-Mar 14 days | 28-Mar 28 days | 11-Apr 42 days | 25-Apr 56 days |
| C1 | 95 | 78 | 50 | 19 | | |
| C2 | 96 | 82 | 56 | 22 | | |
| C3 | 95 | 70 | 32 | 13 | | |
| C4 | 95 | 69 | 45 | 7 | | |
| C5 | 95 | 82 | 56 | 20 | | | the effect on stability of a 1000-fold dilution of the non-demetalated plasmid DNA into demetalated PBS. The results (Table 10, conditions C1-C3) indicated a reduction in stability when the DNA was not demetalated, suggesting that it is necessary to demetalate the DNA and the PBS to obtain maximum stability.

In order to determine if the enhanced stability in the demetalated conditions was due to the inactivation of residual contaminating nuclease activity (caused by metal ion removal) in the DNA, we performed an experiment to determine the effects of removing or denaturing any contaminating nuclease activity on DNA stability. The results (Table 11) indicated that the addition of 0.1% SDS did not significantly enhance stability over the PBS control. Furthermore, treatment of the DNA with 1 mcg of protease K for 1 hour at 24° C., followed by removing the enzyme with a Micropure EZ membrane, did not enhance stability. The Micropure EZ membrane treatment alone, also did not improve stability. In addition, we found that a phenol extraction and ethanol precipitation of the DNA had no effect on stability. These results strongly suggest that the enhanced stability observed in demetalated PBS is not due to the inactivation of residual nuclease activity, but is instead due to the removal of metal ions capable of catalyzing free radical oxidation of the DNA.

To further examine the effects of demetalation on DNA stability a series of DNA stability experiments were carried out using demetalated buffers with an improved batch binding demetalation procedure that ensures efficient removal of trace metal ions and no alteration of the buffer pH. Buffers were demetalated by placing 5 g of Chelex resin in ~75 mL of the buffer to be demetalated. With the solution being stirred at a moderate rate on a magnetic stirrer, 1N HCl was added to the slurry dropwise, to adjust the pH to the desired pH of the buffer. Then, additional 1N HCl was added over the next 15-30 minutes until the pH of the slurry stabilized at the desired pH. When the pH had stabilized, the slurry was filtered and the washed and pH adjusted Chelex resin collected. The entire 5 grams of washed resin was then placed in 250 mL of the buffer to be demetalated (in a 250 mL capped bottle) and stirred slowly overnight, at 2-8° C. Then, the buffer was filter sterilized using a Corning vacuum filtration unit with a 0.22 mm cellulose acetate membrane. Prior to collecting the filtered buffer the membrane of the Corning filtration unit was washed twice, with 5-10 mL of the slurry each time, to remove any trace metal ions from the cellulose acetate membrane and to wash the polystyrene container. The sterile demetalated buffer was stored at 2-8° C. until used.

To determine the effects of reagent purity and demetalation on DNA stability, plasmid DNA at 2 mcg/mL was incubated in PBS made with reagents from two different sources at pH 7.2 for 6 weeks at 50° C. The results (FIG. 15) indicated that demetalation of the formulation buffer significantly enhanced DNA stability for PBS made with the B reagents, but had little effect on the stability of DNA in PBS made with the A reagents. These results suggest that trace metal ion impurities in formulation buffer reagents can lead to DNA degradation during storage, and that demetalation of the less pure formulation buffers improves DNA stability.

To determine the effects of demetalation on DNA stability in formulations of a higher pH, a stability study was performed over 6 weeks at 50° C., with DNA at 2 mcg/mL in PBS and demetalated PBS adjusted to pH 8.0. The results, shown in FIG. 16, indicate that demetalation of the formulation buffer also improved DNA stability at pH 8.0, in PBS.

Figure 17:
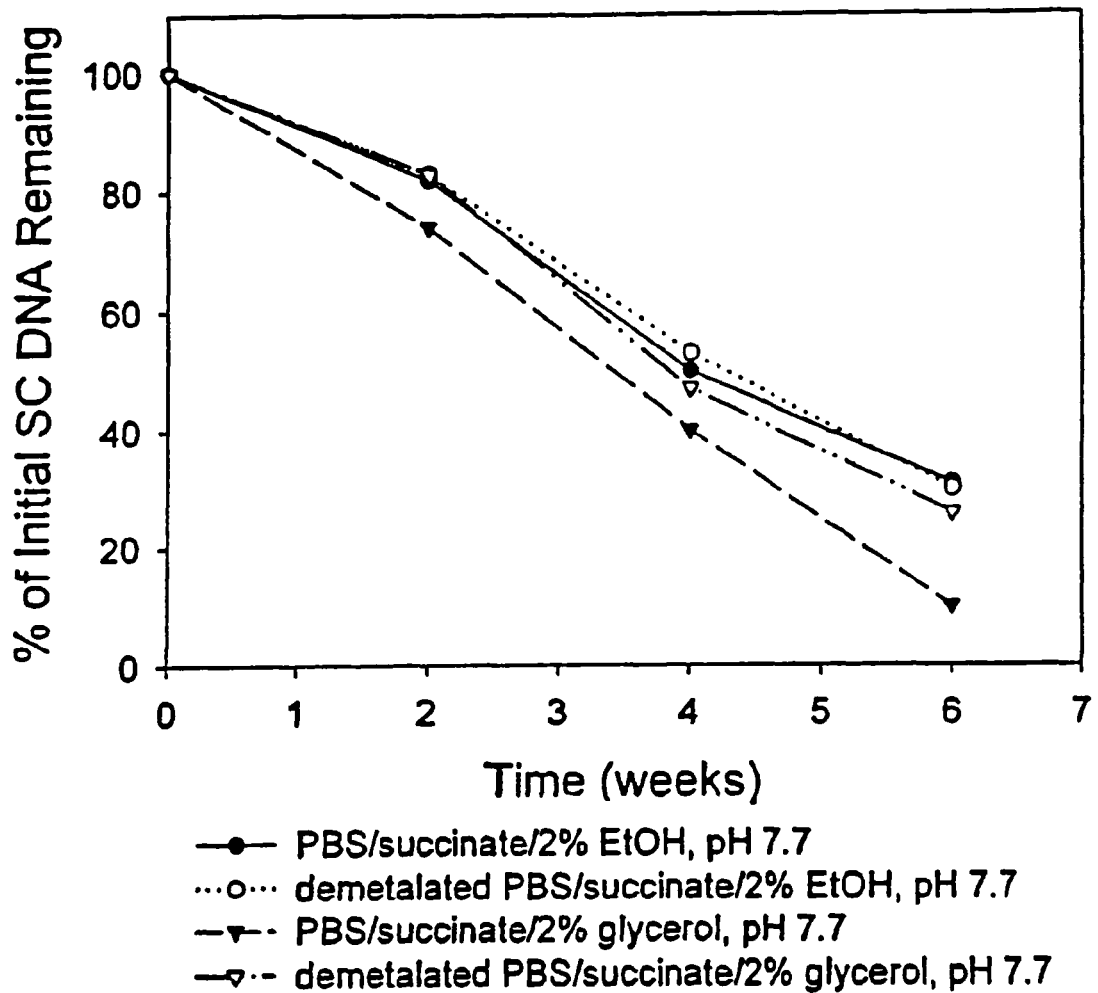
FIG. 17 shows the effect of demetalation on DNA stability in formulations containing succinate and ethanol. DNA stability is measured as % of initial supercoiled (SC) DNA remaining.

To determine the effects of demetalation on DNA stability in formulations containing free radical scavengers and metal ion chelators a DNA stability experiment was performed over 6 weeks at 50° C. with plasmid DNA at 2 mcg/mL. Two formulations were tested, each in the demetalated and non-demetalated state. PBS was used as the buffer and 10 mM sodium succinate as the chelator. Ethanol and glycerol were used as free radical scavengers, each at 2% (v/v). The results, shown in FIG. 17, indicate that demetalation improved DNA stability slightly in the formulation containing glycerol, but had no effect on DNA stability in the ethanol formulation. These results suggest that the same level of DNA stability can be achieved either by controlling free radical oxidation with succinate and ethanol, or by removal of the trace metal ions with demetalation. However, the addition of succinate and ethanol would be expected to protect the DNA from any trace metal ions introduced during DNA vaccine formulation and filling. Although demetalation would not protect the DNA from metal ions introduced after the demetalation procedure it would reduce the load of trace metal ions in the formulation and may increase DNA stability during storage over much longer periods of time.

Figure 18:
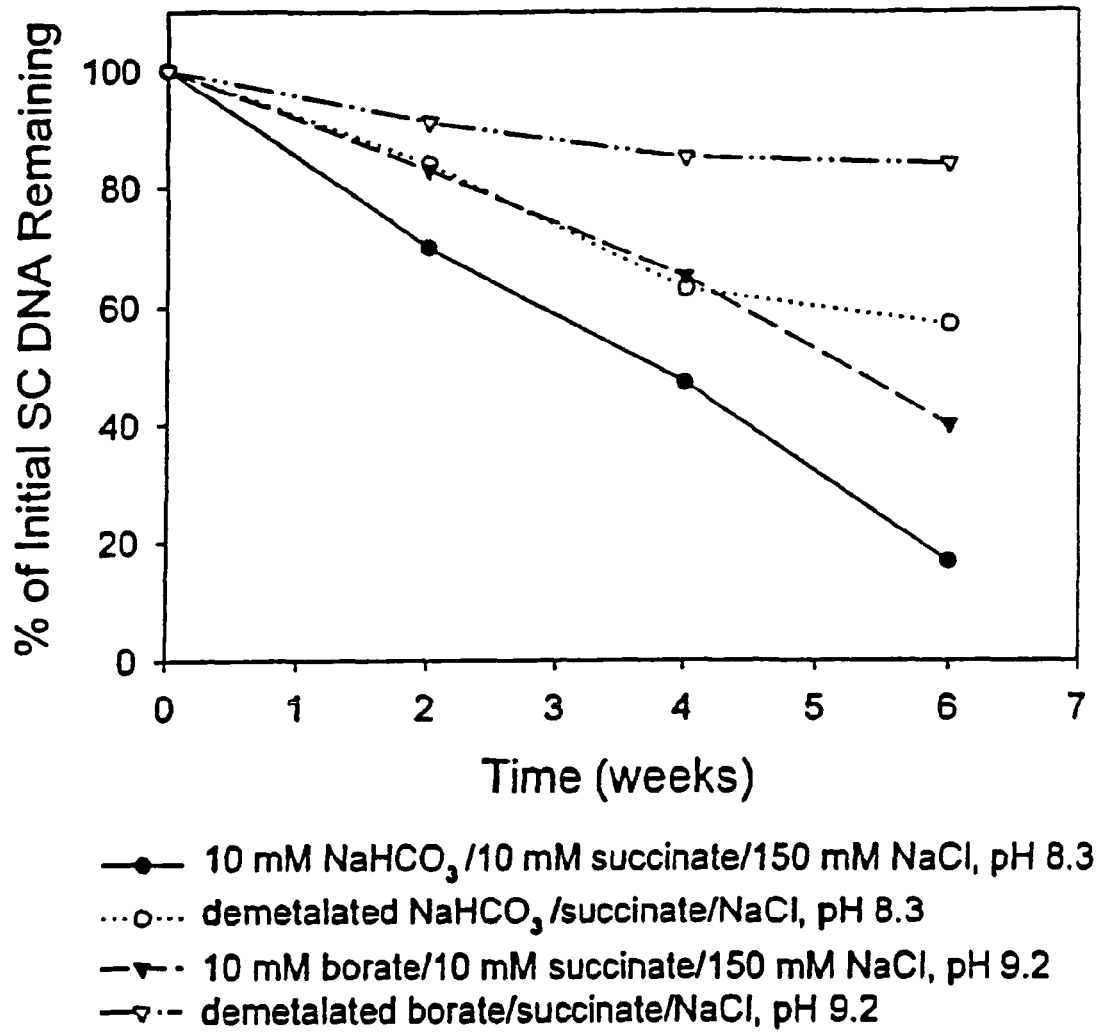
FIG. 18 shows the effect of demetalation on DNA stability in formulations containing bicarbonate and borate. DNA stability is measured as % of initial supercoiled (SC) DNA remaining.

To examine the effects of demetalation on DNA stability in other buffer types, a DNA stability experiment was performed with plasmid DNA over 6 weeks at 50° C. with DNA at 2 mcg/mL in either a bicarbonate or a borate containing buffer. The results, shown in FIG. 18 below, indicate that demetalation greatly increased DNA stability in each of the formulations. Therefore, the data suggests that demetalation is an effective way to enhance DNA stability in a variety of formulation buffers over a wide range of pH.

Figure 19:
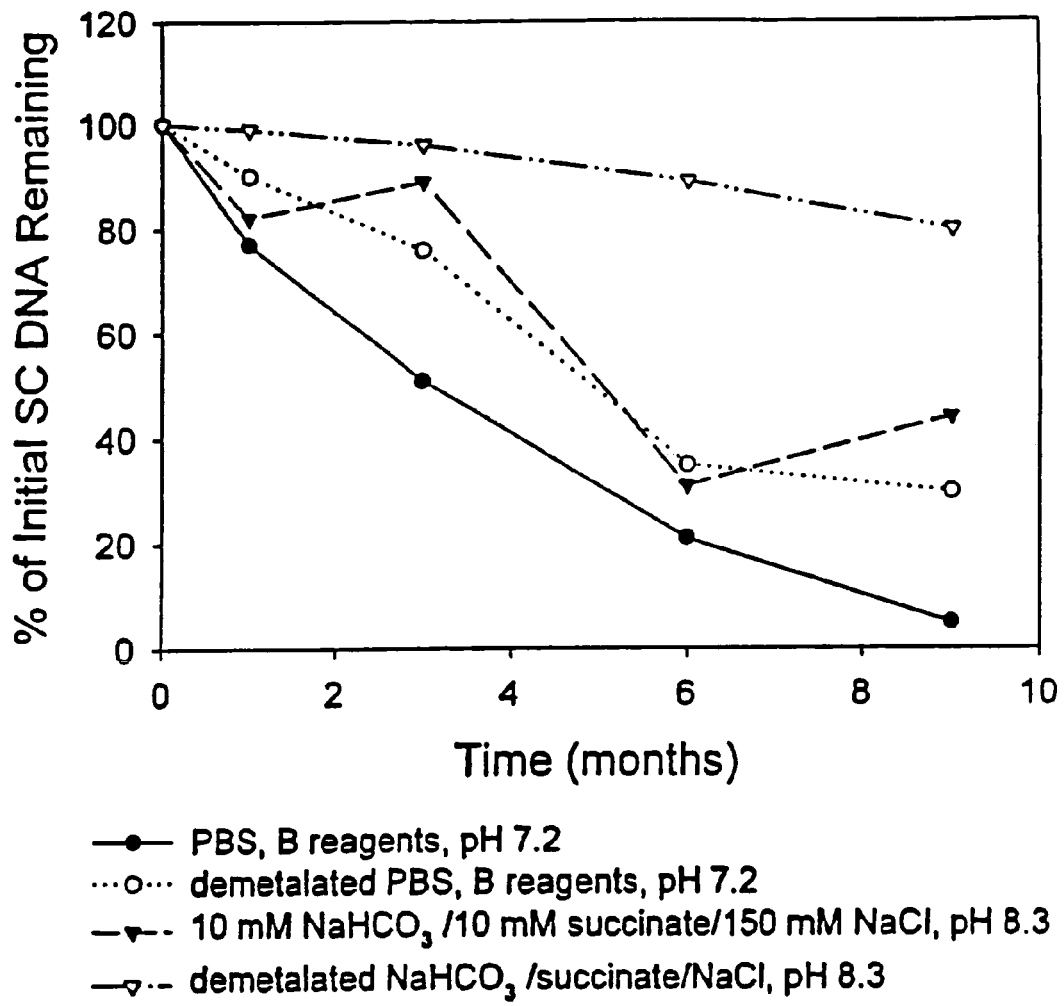
FIG. 19 shows the effect of demetalation on DNA stability in PBS and bicarbonate formulations at 30° C. DNA stability is measured as % of initial supercoiled (SC) DNA remaining.

To determine if demetalation of the formulation buffer for a DNA vaccine enhances DNA stability at lower temperatures and over much longer periods of storage, a DNA stability experiment was performed over 9 months at 30° C. with DNA at 2 mcg/mL, in two formulations. The results, shown in FIG. 19, indicate that demetalation of the PBS and bicarbonate containing formulations significantly improved DNA stability. These results suggest that the enhancement of DNA stability by demetalation is effective over a wide range of temperatures and time in storage.

EXAMPLE 14

Effect of free radical scavengers on DNA stability—It is now widely recognized that one mechanism of DNA degradation involves free radical oxidation by molecules such as hydroxyl radicals. One way to prevent or minimize the amount of DNA damage by free radicals is to add a free radical scavenger to the solution. These molecules serve the purpose of protecting the DNA, by competing with the DNA for the free radicals. Since the scavengers are compounds selected to be highly reactive towards free radicals and are often present at higher concentrations than the reactive part of the DNA (usually the deoxyribose sugar), they effectively protect the DNA from damage.

Figure 11:
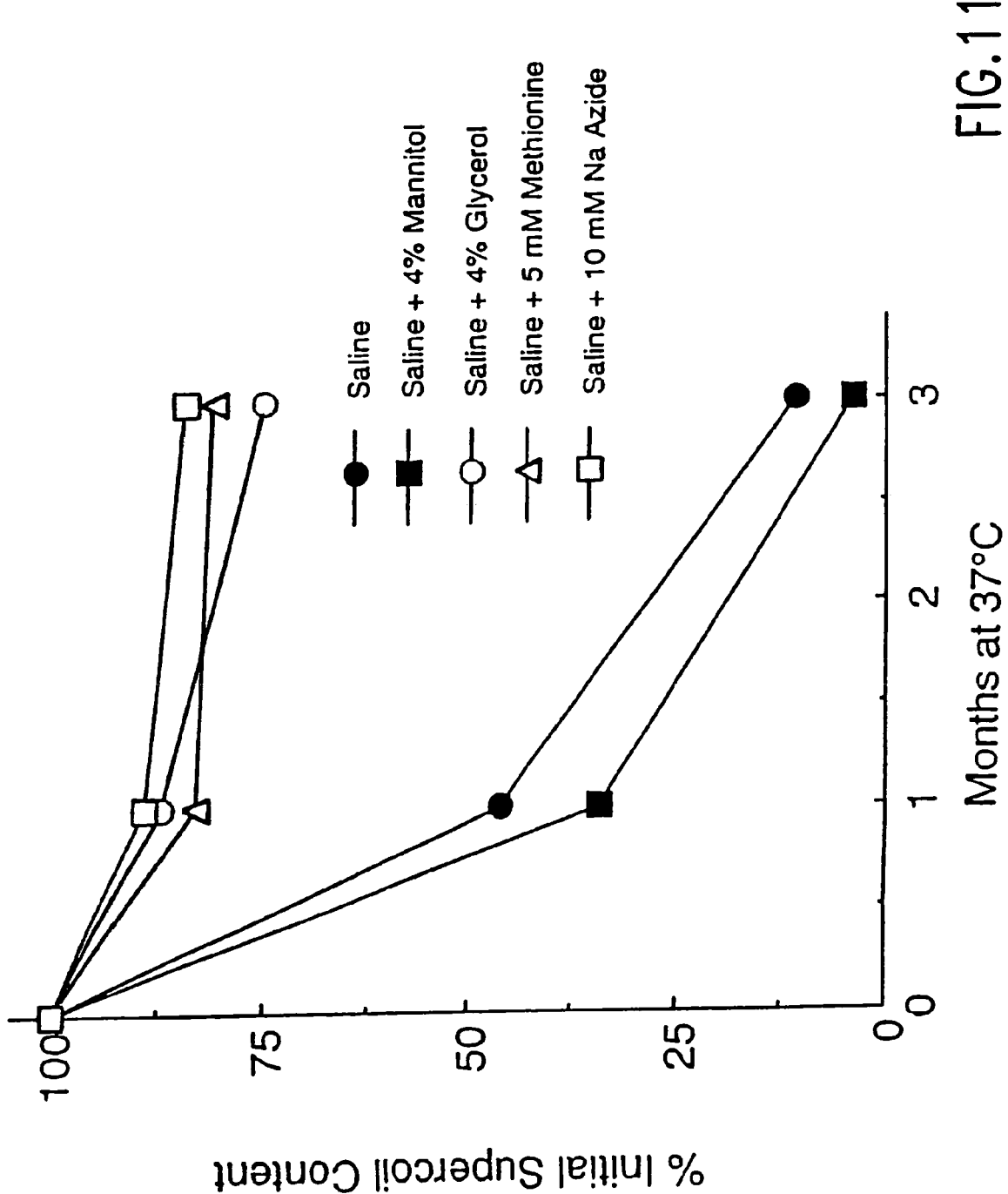
FIG. 11 shows the effect of free radical scavengers on the supercoil content of Influenza DNA vaccine during storage at 37° C. DNA plasmid solutions were prepared at 100 mcg/mL DNA in saline. Supercoil content of plasmid was determined by agarose gel electrophoresis.

To determine if free radical oxidation was occurring during storage and to text the effectiveness of several free radical scavengers, Influenza DNA vaccine, HA (Georgia/93) was formulated in saline containing 4% (w/v) mannitol, 4% (v/v) glycerol, 5 mM methionine or 10 mM sodium azide (known free radical scavengers) and incubated at 37° C. for three months. The DNA was subjected to agarose gel electrophoresis at three timepoints to determine the percent of initial supercoiled DNA remaining. The results in FIG. 11, indicate that in saline, glycerol, methione and sodium azide stabilized the DNA, compared to the saline control. These early results suggested that free radical oxidation was occurring during storage, and that three different free radical scavengers were effective stabilizers of the DNA.

The results of another study designed to examine the effects of the free radical scavenger dimethyl sulfoxide (DMSO), and the

TABLE 12

Table 12: Effects of reducing agents, Desferal and dimethyl sulfoxide on DNA stability at 5, 24 and 37° C. The percent of initial supercoiled DNA remaining was determined by agarose gel electrophoresis.

| | | Percent of initial supercoiled DNA remaining. | | | | | |
|---|---|---|---|---|---|---|---|
| | 30-Aug | 1 Month | | | 3 Month | | |
| condition | % Initial SC | 5 C. | 25 C. | 37 C. | 5 C. | 24 C. | 37 C. |
| A | 70 | 0 | 0 | 0 | 0 | 0 | 0 |
| B | 48 | 0 | 0 | 0 | 0 | 0 | 0 |
| C | 61 | 0 | 0 | 0 | 0 | 0 | 0 |
| D | 100 | 100 | 96 | 0 | 100 | 44 | 0 |
| E | 100 | 100 | 93 | 0 | 100 | 12 | 0 |
| F | 100 | 100 | 100 | 91 | 100 | 100 | 58 |
| G | 100 | 99 | 99 | 89 | 100 | 91 | 37 |

DNA = Influenza DNA vaccine
Volume & concentration = 0.8 mL/vial at 20 mcg/mL
Temperature = 5, 24 and 37° C.
container = 3.0 mL glass vials + Teflon stoppers
Time 0 = 30 Aug 95
All conditions (A–G) contained PBS, pH 7.2 in addition to the reagents below.
A = Ascorbic Acid (0.2%)
B = Sodium Metasulphite (.2%)
C = Sodium Sulphite (.2%)
D = Desferal (1 mM)
E = Thioglycerol (.2%)
F = DMSO (.2%)
G = PBS control

TABLE 13

Table 13: Effect of free radical scavengers on DNA stability at 5, 24 and 37° C. Percent of initial supercoiled DNA remaining was determined by agarose gel electrophoresis.

| | | Percent of initial supercoiled DNA remaining. | | | | | |
|---|---|---|---|---|---|---|---|
| | 29-Sep | 1 Month | | | 3 Month | | |
| Condition | Initial % SC | 5 C. | 24 C. | 37 C. | 5 C. | 24 C. | 37 C. |
| A | 100 | 100 | 100 | 90 | 100 | 95 | 46 |
| B | 100 | 100 | 100 | 84 | 100 | 90 | 46 |
| C | 100 | 100 | 97 | 77 | 99 | 83 | 30 |
| D | 100 | 77 | 45 | 5 | 63 | 26 | 0 |
| E | 97 | 100 | 100 | 51 | 99 | 83 | 0 |
| F | 100 | 100 | 100 | 55 | 98 | 78 | 0 |
| G | 100 | 100 | 100 | 94 | 99 | 90 | 54 |

DNA = Influenza DNA vaccine
Volume & concentration = 0.8 mL/vial at 20 mcg/mL.
Temperature = 5, 24 and 37° C.
Container = 3.0 mL glass vial + Teflon stoppers
Time 0 = 29 Sept 95
DNA was formulated in either PBS, pH 7.2 or in saline (0.9% (w/v) NaCl) containing methionine, glycerol or ethanol.
Seven conditions were tested (A–G), described below.
A = PBS + 10 mM methionine
B = PBS + 10% (v/v) glycerol
C = PBS control, pH 7.2
D = Saline only
E = Saline + 10 mM methionine
F = Saline + 10% (v/v) glycerol
G = PBS + 2% (v/v) ethanol reducing agents ascorbic acid, sodium metabisulfite, sodium sulfite and thioglycerol on DNA stability, is shown in Table 12. In this example, DNA was formulated at 20 mcg/mL in PBS (pH 7.2) and incubated at 5, 24 and 37° C. The results indicate a dramatic destruction of the DNA in the presence of all of the reducing agents, and an enhancement of stability with 0.2% (v/v) DMSO, compared with the PBS control. The results of this experiment are consistent with those of FIG. 11, that most of the non-reducing free radical scavengers tested, have stabilized the DNA.

A re-examination of free radical scavengers was then performed to examine the effects of 10% (v/v) glycerol, 10 mM methionine and 2% (v/v) ethanol on DNA stability. In this experiment the DNA was formulated at 20 mcg/mL in PBS (pH 7.2) and incubated at 5, 24 and 37° C. The results, shown in Table 13, indicated that 2% ethanol in PBS was the most effective stabilizer. However, glyerol and methionine also showed some stabilizing effect. Another result from this study was that the PBS formulations were much more stable than the saline formulations, presumably because the pH tended to drift down in the saline formulations over time, causing an increase in the rate of degradation.

The results of an experiment to examine the effects free radical scavengers pentoxifylline, tert-butylhydroquine and p-aminobenzoic acid on DNA stability are shown in Table 14. In this study the IDV, HA (Georgia/93), was formulated at 2.0 mcg/mL in PBS (pH 7.2) in the presence of a 10 mM concentration of the scavenger. The samples for this study were incubated at 50° C. and examined for supercoiled DNA content by agarose gel electrophoresis. The results indicated that none of the scavengers tested improved the stability of the DNA, and in fact they greatly accelerated the degradation of the DNA. It is not clear why these scavengers accelerated the degradation of the DNA, while ethanol, DMSO, glycerol and methionine provided an enhancement in stability.

The ability of ethanol to stabilize the DNA was also examined in demetalated PBS, as well as in demetalated and deoxygenated PBS. For these two studies the DNA was formulated at 2.0 mcg/mL and incubated at 50° C. The results, shown in Tables 9 and 10, indicate that 5% (v/v) ethanol stabilized the DNA in PBS, and in either of the demetalated formulations.

Recent results from the first time point (1 month) of a long-term stability study also indicate that 5% ethanol stabilizes the DNA in demetalated PBS at 37° C., in formulations containing 2.0 mcg/mL DNA. The one month time point indicated that the PBS control had 93% of the initial supercoiled DNA remaining, while the demetalated sample had 96.1% and the demetalated sample containing 5% ethanol had 100%.

Figure 20:
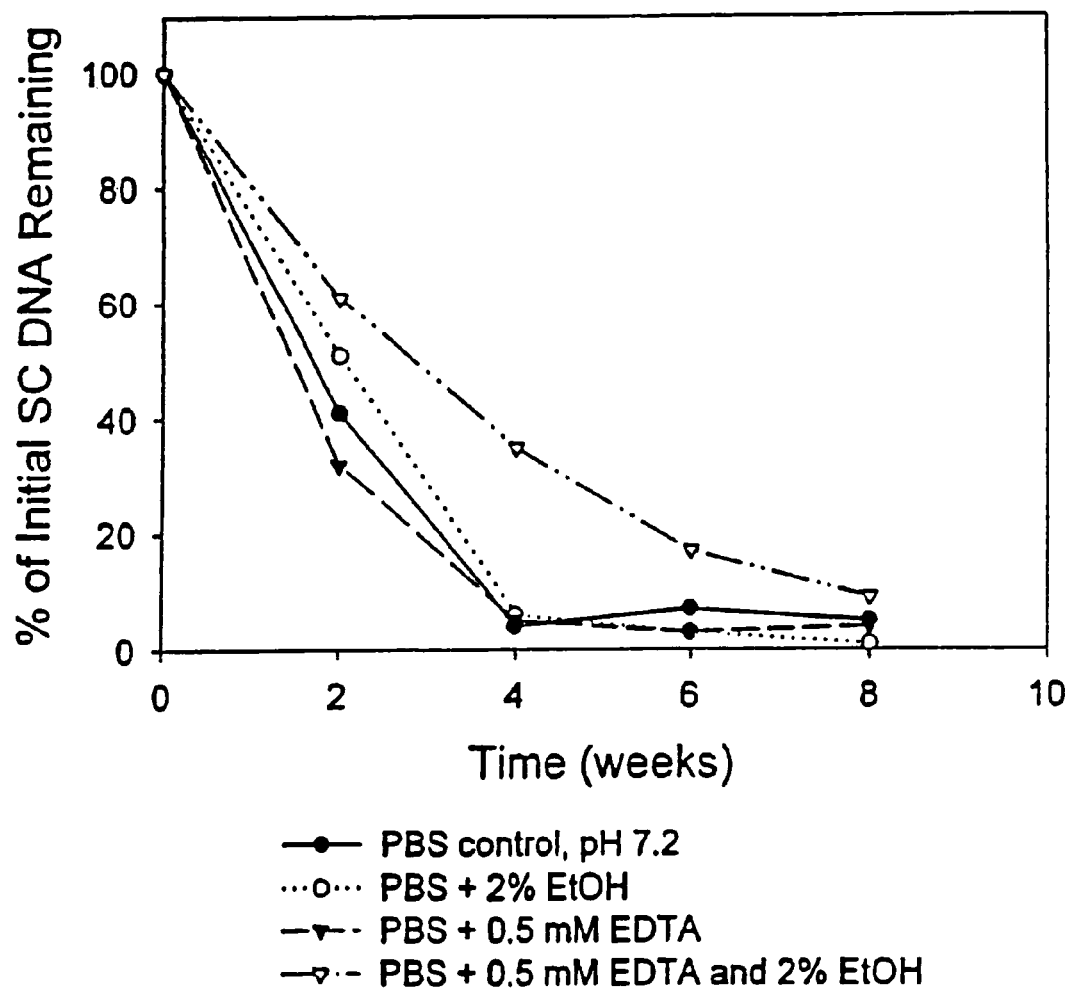
FIG. 20 shows the effect of EDTA and ethanol on DNA stability at 50° C. in PBS at pH 7.2. DNA stability is measured as % of initial supercoiled (SC) DNA remaining.

To examine the effects of free radical scavengers on DNA stability, two DNA stability experiments were performed over 8 weeks at 50° C. with DNA at 20 mcg/mL in PBS at pH 7.2 and pH 8.0. Since ethanol is an effective free radical scavenger approved for human use, ethanol was tested as the scavenger at 2% (v/v) in the presence and absence of EDTA. The results of the first experiment (at pH 7.2) are shown in FIG. 20 below. The results indicate that ethanol alone enhanced DNA stability, while EDTA alone decreased DNA stability. The combination of ethanol and EDTA provided a large increase in DNA stability up to 4 weeks, but only a small increase in stability by week 8. These results suggest that ethanol is a more effective scavenger of free radicals in the presence of EDTA, than in its absence. Moreover, the results suggest that EDTA alone decreases DNA stability in the absence of ethanol, but increases DNA stability in the presence of ethanol. These results strongly suggest that ethanol is a more effective scavenger in the presence of EDTA because EDTA removes metal ions bound to DNA, thereby allowing the generation of hydroxyl radicals in the bulk solution, as opposed to the generation of radicals by iron bound to the DNA. The production of hydroxyl radicals in the bulk solution would allow ethanol molecules more time to scavenge the radicals since the mean free path of the radical would be longer before its interaction with the DNA. Hydroxyl radicals generated by iron molecules bound to the DNA would be in very close proximity to the DNA. Therefore, the ability of ethanol to scavenge radicals produced on the "surface" of the DNA would greatly diminished. These results also suggest that chelators other than EDTA may be effective DNA stabilizers, provided that the chelator is able to remove metal ions (iron and copper) already bound to the DNA.

Figure 21:
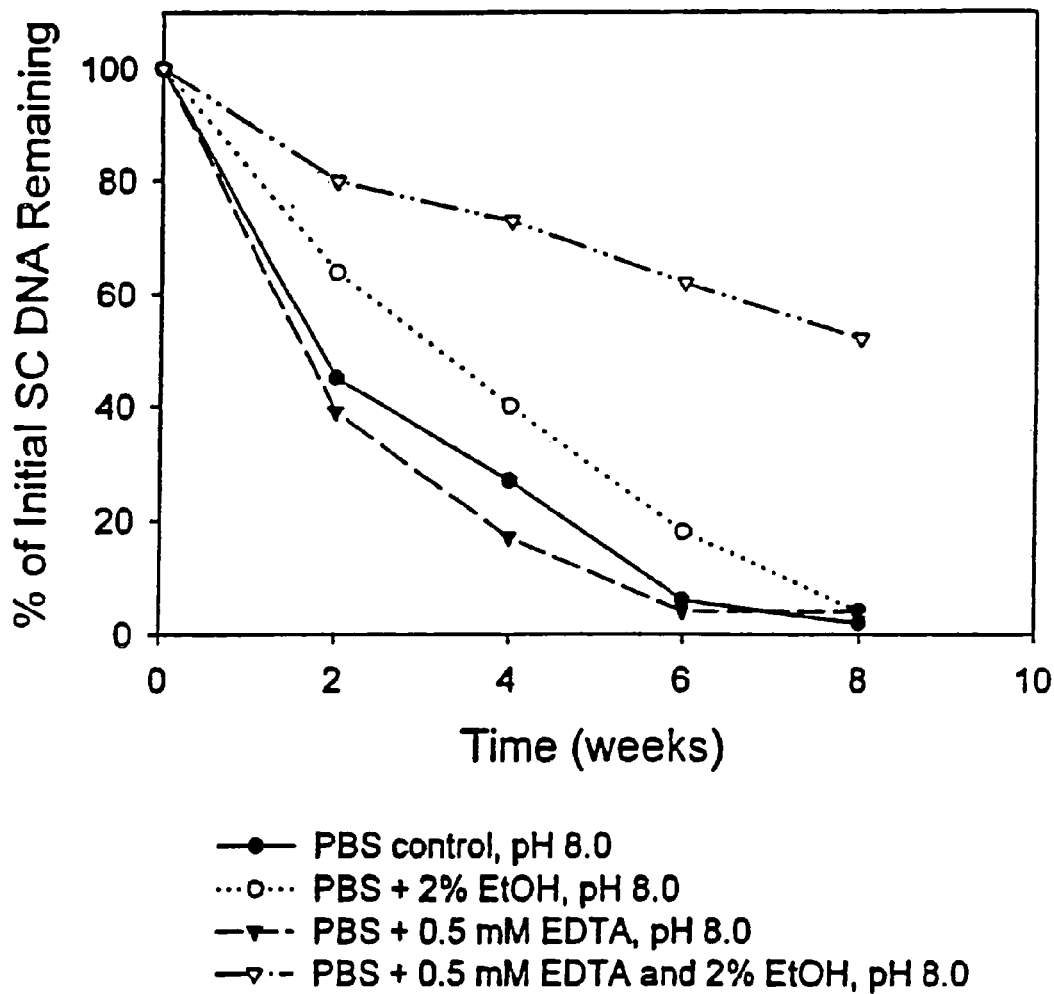
FIG. 21 shows the effect of EDTA and ethanol on DNA stability at 50° C. in PBS at pH 8.0. DNA stability is measured as % of initial supercoiled (SC) DNA remaining.

The results of the second stability study, at pH 8.0 are shown below in FIG. 21. The data from this experiment clearly show that the DNA stabilizing effects of ethanol and EDTA/EtOH are greater at pH 8.0 than at pH 7.2.

Figure 22:
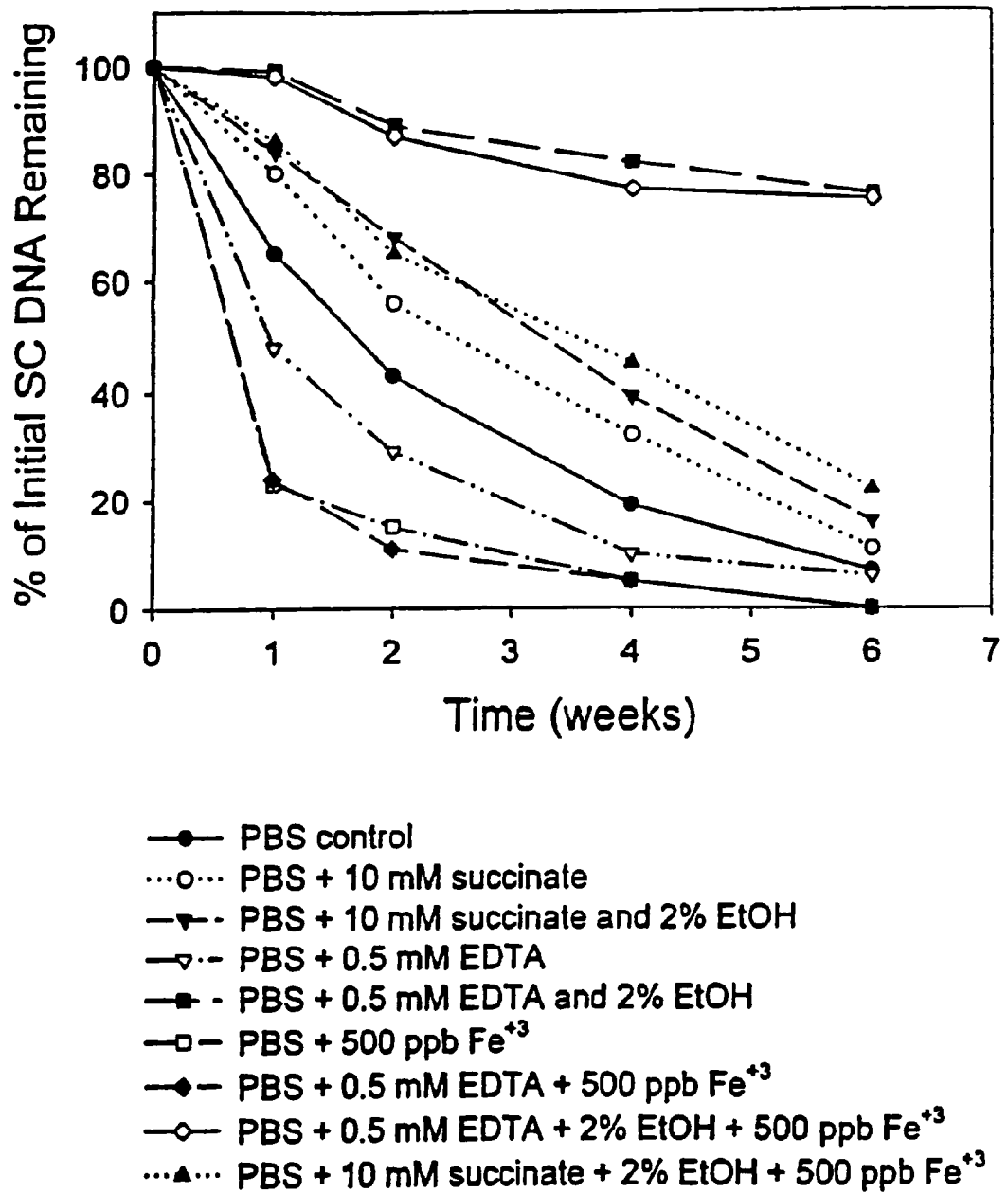
FIG. 22 shows the effect of iron on DNA stability in formulations containing EDTA/ethanol at 50° C. DNA stability is measured as % of initial supercoiled (SC) DNA remaining.

To determine whether the combination of succinate and ethanol would provide the same degree of DNA stabilization as observed with the EDTA/EtOH combination, and to determine whether either of these combinations would protect DNA from the presence of $Fe^{+3}$, a stability experiment was performed over 6 weeks at 50° C. in 10 mM sodium phosphate buffer containing 150 mM NaCl at pH 8.0 with 20 mcg/mL DNA. The results indicated that the succinate/EtOH combination did not provide the same degree of DNA stabilization as EDTA/EtOH. However, the combination of succinate and ethanol did provide nearly complete protection from the enhanced free radical generation produced by the addition of 500 ppb $Fe^{+3}$. The results, shown in FIG. 22, also indicated that the EDTA/EtOH combination provided the best DNA stability overall and provided complete protection from the addition of 500 ppb $Fe^{+3}$. These results suggest that the specific combination of EDTA and ethanol provides greatly enhanced DNA stability, and that the same degree of DNA stability cannot be achieved by using the combination of succinate and ethanol.

EXAMPLE 15

Effect of metal ion chelators on DNA stability—In preliminary studies designed to examine the effects of buffer ions, pH and salt on DNA stability, we also examined the effect of adding 1 mM and 10 mM EDTA to DNA formulated in PBS (pH 7.2). For these early experiments the plasmid DNA was formulated at 100 mcg/mL and incubated at 60° C. for 48 hours. The supercoiled DNA content was then determined by agarose gel electrophoresis. The results, shown in Table 5, indicated that EDTA had no effect on the stability of the DNA. Suggesting, at this early time, that trace metal ions were not required for the DNA degradation process we were observing.

Other experiments have also included an examination of the effects of EDTA on DNA stability. The results shown in Table 12, for example, indicated that 0.5 mM EDTA had no significant effect on the stability of DNA formulated at 2.0 mcg/mL in PBS (pH 7.2), or in PBS containing 5% (v/v) ethanol, when incubated at 50° C.

An early experiment designed to examine the effect of the iron chelator Desferal (at 1 mM) on DNA stability, indicated an enhanced rate of degradation. In this study the DNA was formulated in PBS (pH 7.2) at 20 mcg/mL and incubated at 5, 25 and 37° C. The reason for the enhanced rate of degradation is not clear.

Later experiments also confirmed the detrimental effect of Desferal on DNA stability. The results shown in Table 15, for example, show that 0.5 mM Desferal caused a rapid degradation of the DNA in PBS, even if the PBS was treated with Desferal before mixing it with the DNA. This experiment also showed that treatment of the DNA with 1.0 mM Desferal, overnight, prior to diluting it in demetalated PBS, still resulted in a rapid degradation of the DNA. For these latest experiments with Desferal, the DNA was formulated in PBS at 2.0 mcg/mL and incubated at 50° C.

TABLE 14

Table 14: Effects of metal ion chelators and free radical scavengers on DNA stability. Percent of initial supercoiled DNA remaining was determined by agarose gel electrophoresis.

DNA = Influenza DNA vaccine
Volume & Concentration = 0.8 ml/vial at 2.0 mcg/ml
Temperature = 50 C.
Container = 3 ml glass vials and Teflon stoppers
Time 0 = 6 March 96
All conditions contained PBS, pH 7.2
C1 = PBS control, pH 7.2
C2 = +0.5 mM IHP (Inositol hexaphosphate)
C3 = +0.5 mM EDDHA (Ethylenediamine-Di(o-hydroxy-phenylacetic acid)
C4 = +0.5 mM DTPA (Diethylenetriaminepenta-acetic acid)
C5 = +0.5 mM TPP (tripolyphosphate)
C6 = +10 mM PTX (pentoxyifylline)
C7 = +10 mM TBHQ (tert-Butylhydroquinone)
C8 = +10 mM PABA (p-Aminobenzoic Acid)

| | % of Initial Supercoiled DNA remaining | | | | | |
|---|---|---|---|---|---|---|
| Conditions | 6-Mar Initial % SC | 13-Mar 7 days | 20-Mar 14 days | 3-Apr 28 days | 17-Apr 42 days | 1-May 56 days |
| C1 | 97 | 77 | 53 | 9 | | |
| C2 | 98 | 85 | 69 | 34 | | |
| C3 | 95 | 68 | 43 | 12 | | |
| C4 | 97 | 65 | 29 | 0 | | |
| C5 | 97 | 83 | 64 | 27 | | |
| C6 | 97 | 78 | 47 | 5 | | |
| C7 | 19 | 0 | 0 | 0 | | |
| C8 | 98 | 17 | 0 | 0 | | |

TABLE 15

Table 15: Effects of Desferal, a metal ion chelator, on the stability of DNA. Percent of initial supercoiled DNA remaining was determined by agarose gel electrophoresis.

DNA = Influenza DNA vaccine
Volume & Concentration = 0.8 ml/vial at 2.0 mcg/ml
Temperature = 50 C.
Container = 3 ml glass vial with Teflon stoppers
Time 0 = 28 Feb 96
All conditions contained PBS, pH 7.2
C1 = PBS control, pH 7.2
C2 = +0.5 mM Desferal
C3 = +10% (v/v) ethanol
C4 = +0.5 mM Desferal + 10% (v/v) ethanol
C5 = demetalated PBS, demetalated DNA
C6 = DNA incubated with Desferal, then mixed with demetalated PBS
C7 = PBS incubated with Desferal, non-demetalated DNA was then added.

| | % of Initial Supercoiled DNA remaining | | | | | |
|---|---|---|---|---|---|---|
| Condition | 28-Feb Initial % SC | 6-Mar 7days | 13-Mar 14 days | 27-Mar 28 days | 10-Apr 42 days | 24-Apr 56 days |
| C1 | 97 | 82 | 58 | 17 | | |
| C2 | 97 | 11 | 9 | 0 | | |
| C3 | 98 | 86 | 68 | 22 | | |
| C4 | 97 | 30 | 4 | 0 | | |
| C5 | 97 | 93 | 87 | 73 | | |
| C6 | 98 | 92 | 87 | 68 | | |
| C7 | 96 | 94 | 88 | 69 | | |
| C8 | 97 | 92 | 86 | 62 | | |
| C9 | 96 | 24 | 0 | 0 | | |
| C10 | 97 | 19 | 0 | 0 | | |

The results of an experiment to examine the effects of some well characterized metal ion chelators, on DNA stability, are shown in Table 14. For these studies the DNA was formulated at 2.0 mcg/mL in PBS (pH 7.2) and incubated at 50° C. Four different chelators were tested, each at 0.5 mM. The results indicated that inositol hexaphosphate (IHP) and tripolyphosphate (TPP) improved the stability of the DNA. However, ethylenediamine-Di(o-hydoxy-phenylacetic acid (EDDHA) and diethylenetriaminepenta-acetic acid (DTPA) did not enhance stability. These results suggest that IHP and TPP may be useful to further stabilize the DNA in demetalated PBS, and in demetalated PBS containing ethanol as a free radical scavenger. Although the stabilizing effect of IHP and TPP are consistent with the enhancement of stability with demetalation, and the stabilizing effects of ethanol (based on the mechanism of DNA degradation being a metal ion catalyzed, free radical oxidation) it is not clear why other metal ion chelators do not stabilize the DNA. The published literature (see *J. Biol. Chem.* 259, 3620-3624; 1984) suggests that IHP, EDDHA, DTPA and Desferal lack a free coordination site on the metal, when coordinated to iron. Therefore, it was reported that these four chelators do not produce hydroxyl radicals when complexed to iron, as EDTA does. With this understanding of the chemistry, it is difficult to explain the differential effects of these chelators on DNA stability. However, our results do suggest that chelators containing multiple phosphate ligands may be the most effective chelators to protect DNA from metal ion catalyzed oxidation. Furthermore, additional chelators with multiple phosphate ligands would include the various salt forms of polyphosphoric acid.

The results of our most recent studies to examine different buffers in the demetalated state (see Example 16) also suggests that specific metal ion chelators are important for stabilizing DNA during storage. Since demetalated PBS containing succinate or malate was superior to demetalated PBS alone, the stabilizing effect is likely to be due to the binding of metal ions by the succinate and malate anions. However, our data also indicate that citrate, a commonly used buffer with a higher affinity for metal ions than succinate, did not provide any stabilization of the DNA. Moreover, EDTA, Desferal, inositol hexaphosphate, EDDHA and DTPA all have very high affinities for metal ions, but they do not stabilize the DNA during storage. Therefore, the ability of the metal ion chelator to stabilize DNA formulations is not related to the binding affinity of the chelator for metal ions. This conclusion suggests that the identification of effective chelators will require an empirical screening of molecules with multiple phosphate ligands, or with a chemical resemblance to succinic or malic acid.

Figure 23:
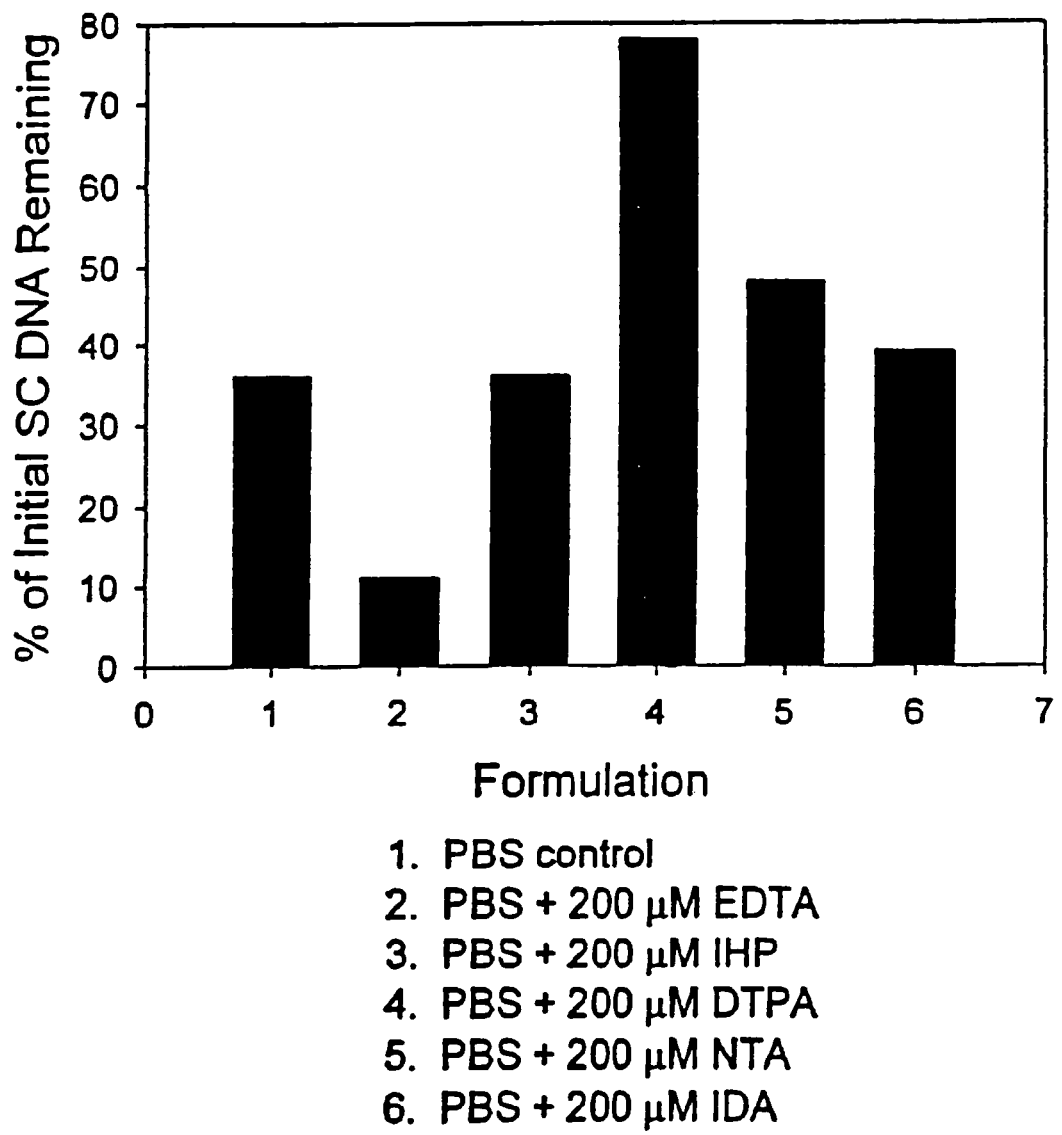
FIG. 23 shows the effect of metal iron chelators on DNA stability in PBS at pH 8.0. DNA stability is measured as % of initial supercoiled (SC) DNA remaining.

To examine the effects of metal ion chelators on DNA stability, a series of DNA stability experiments were performed. The purpose of the first experiment was to determine the effects of several different chelators on DNA stability in PBS at pH 8.0 in the absence of ethanol. The experiment was carried out over 2 weeks at 50° C. using 20 mcg/mL DNA. The results, shown in FIG. 23, indicate that only NTA (nitrilotriacetic acid) and DTPA (diethylenetriaminepentaacetic acid) enhance DNA stability in the absence of ethanol. The data in FIG. 23 is consistent with the previous results shown in FIGS. 21 and 22, in that EDTA decreased DNA stability in the absence of ethanol. These results suggest that, among these chelators, only DTPA is an effective DNA stabilizer in the absence of ethanol.

Figure 24:
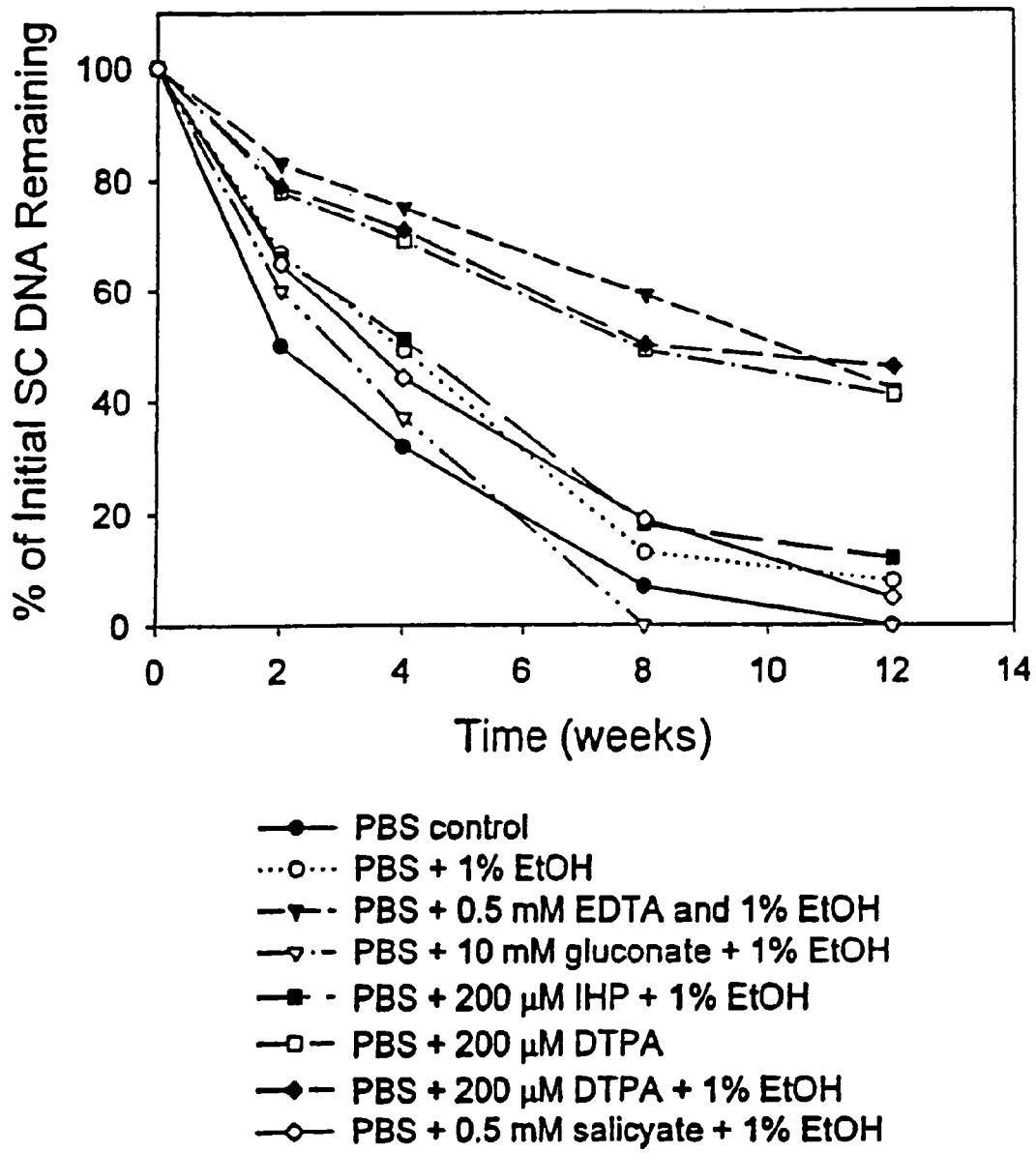
FIG. 24 shows the effect of metal ion chelators on DNA stability in PBS at pH 8.0 in the presence of ethanol. DNA stability is measured as % of initial supercoiled (SC) DNA remaining.

To examine the ability of metal ion chelators to enhance DNA stability in the presence of ethanol an experiment was performed using 5 different chelators over 12 weeks at 50° C. in PBS at pH 8.0. The results, shown in FIG. 24, indicated that only DTPA and EDTA significantly increased DNA stability over the PBS control containing 1% EtOH. However, 200 mM DTPA also enhanced DNA stability by an equivalent amount, in the presence and absence of ethanol. These results are consistent with a published report (see Graf et al. 1984, *J. Biol. Chem.* 259: 3620-3624) that iron-DTPA complexes do not support the generation of hydroxyl radicals, and therefore one would expect that ethanol would not be needed as a scavenger.

Figure 25:
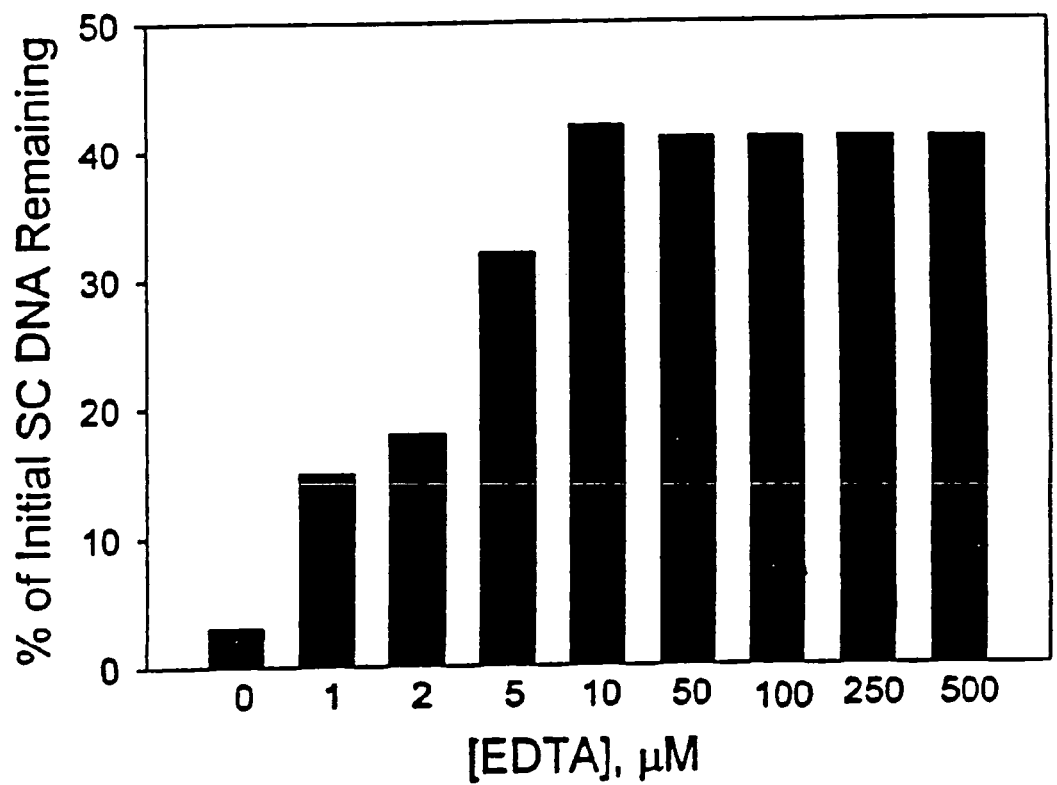
FIG. 25 shows the effect of EDTA concentration on DNA stability in PBS at 1% ethanol. DNA stability is measured as % of initial supercoiled (SC) DNA remaining.

To determine the optimum concentration of EDTA for stabilizing plasmid DNA in PBS containing 1% EtOH at pH 8.0, a stability experiment was performed over 6 weeks at 50° C. using 20 mcg/mL DNA. The results, shown in FIG. 25, indicate that 10 µM EDTA provided the same stability enhancement as 500 µM EDTA, under these conditions. These results suggest that EDTA is enhancing the stability of DNA by binding low concentrations of trace metal ions present in the formulation buffer, or in the DNA preparations. Based on these data, an increase in the DNA concentration from 20 mcg/mL to 1.0 mg/mL may only require an increase in the EDTA concentration from 10 µM to 500 µM. Therefore, the use of EDTA and ethanol to stabilize DNA vaccine formulations should not require greater than 1 mM EDTA, even with DNA vaccines with DNA concentrations of 2.0 mg/mL.

EXAMPLE 16

Effect of demetaled buffers on DNA stability—Our initial studies on the effects of buffer ions were performed with buffers that were not demetalated. However, because the trace metal ion content of the buffers probably varied, depending on the purity of the buffer, the stability of the DNA in non-demetalated buffers may be largely determined by the trace metal ion content. Therefore, it may be necessary to compare the effects of demetalated buffers, to determine the true influence of the buffer ions on DNA stability.

To examine the effects of different buffer ions on stability, four different demetalated buffers were prepared. The control buffer was demetalated PBS at pH 7.2. The other buffers tested were demetalated PBS containing 10 mM sodium succinate (pH 7.2), demetalated PBS containing 10 mM sodium malate (pH 7.2), demetalated sodium bicarbonate (10 mM) containing 150 mM NaCl, 10 mM Tris-Cl, 150 mM NaCl (pH 7.8) and 10 mM Tricine, 150 mM NaCl (pH 7.8). The Tris and Tricine buffers were not demetalated because the buffering ion is cationic and binds to the Chelex 100 column. For this study of demetalated buffers the Influenza DNA vaccine was formulated at 20.0 mcg/mL and incubated at 50° C. The results of the first time point (two weeks) indicated that demetalated PBS control had 75% of the initial supercoiled DNA remaining, while the succinate, malate, sodium bicarbonate, Tris and Tricine buffers had 98%, 94%, 100%, 31% and 65% of the initial supercoiled DNA remaining. These results indicate that the demetalated buffers containing succinate and malate were superior to demetalated PBS, and that demetalated sodium bicarbonate containing 150 mM NaCl was the most stable formulation. Although it is not clear why sodium bicarbonate is superior to PBS, the stabilizing effect of PBS containing succinate and malate is likely to be due to ability of these compounds to chelate metal ions. Because succinate and malate have a safe record of use in pharmaceutical products, and can be used at relatively high concentrations, these compounds may be the most effective way to chelate trace metal ions, and thus stabilize DNA.

EXAMPLE 17

Effect of lyophilization on DNA stability—DNA is susceptible to a number of different degradative precesses in aqueous solution, including free radical oxidation, depurination and β-elimination reactions. One approach to minimize the rate of these precesses would be to lyophilize the DNA, thus lowering the water content and molecular mobility. To determine the effects of lyophilization on DNA stability during storage, six different lyophilized formulations were prepared. The stability of the DNA in the lyophilized samples was compared to a liquid PBS formulation at 20 mcg/mL, after a one month incubation at 37° C., by agarose gel electrophoresis. To prepare the lyophilized samples, Influenza DNA vaccine was formulated at 20 mcg/mL with the appropriate stabilizers and 0.8 mL of solution was placed into 3 mL glass vials. The samples were then placed in the lyophilizer, and frozen during cooling of the shelf to approximately −45° C. over a period of 4 hours. A vacuum was then applied (20 mTorr), while the shelf temperature was maintained between −30° and −20° C. for 26 hours. The temperature of the shelf was then raised to 0° C. for 2 hours, then to a temperature of 25° C. for 6 hours at a specific rate. The vacuum was then released and the vials were stoppered under a nitrogen atmosphere.

Figure 12:
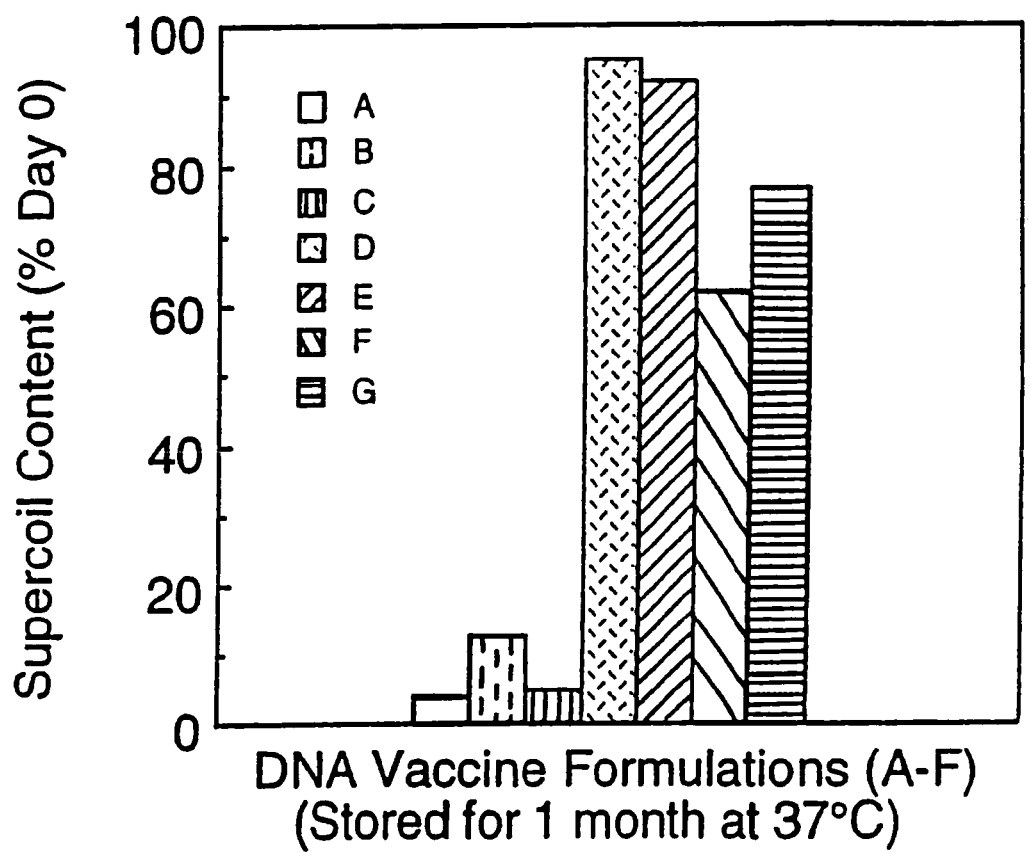
FIG. 12 shows the effect of lyophilization on the supercoil content of Influenza DNA vaccine during storage at 37° C. DNA plasmid solutions were prepared at 20 mcg/mL DNA in either phosphate buffer or phosphate buffered saline (pH 7) containing the indicated sugars. Approximately 0.7 mL of the formulated DNA solution was placed in 3 mL glass vials and then lyophilized. Freeze dried DNA formulations at Day 0 showed no change in plasmid supercoil content compared to liquid controls (no lyophilization). Supercoil content of plasmid was determined by agarose gel electrophoresis. A—PBS (liquid control; no lyophilization); B—PBS containing 5% mannitol, lyophilized; C—Phosphate buffer containing 5% mannitol, lyophilized; D—PBS containing 5% lactose, lyophilized; E—Phosphate buffer containing 5% sucrose, lyophilized; F—Phosphate buffer containing 4% mannitol and 1% lactose, lyophilized; G—Phosphate buffer containing 4% mannitol and 1% sucrose, lyophilized. The formulations were stored for 1 month at 37° C.

The results of the lyophilization study, shown in FIG. 12, indicated that the DNA in four of the six lyophilized formulations was much more stable than the DNA in the liquid PBS control, suggesting that lyophilization will be a very effective way of stabilizing DNA vaccines. Interestingly, DNA vaccine formulations containing amorphous sugars such as sucrose and lactose, greatly stabilize the DNA, while crystalline sugars such as mannitol do not enhance DNA stability compared to the solution control (in PBS). Studies to be initiated soon include the use of demetalated buffers to prepare the lyophilized DNA samples. Since metal ions are very detremental to DNA stability in the liquid state, demetalated and lyophilized DNA formulations may provide greatly enhanced stability over liquid formulations.

Figure 26:
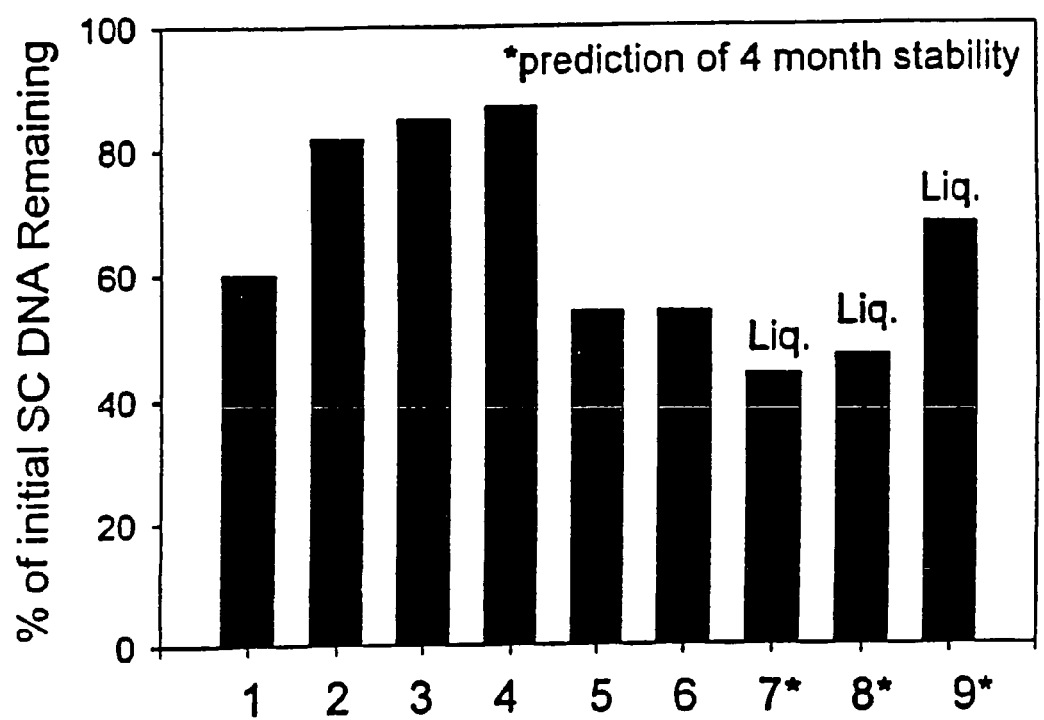
FIG. 26 shows the stability of lyophilized (formulations #1-6) and liquid (formulations 7-9) DNA formulations after 4 months at 50° C. Formulation #1 is 5% sucrose, 5 mM $NaPO_4$; formulation #2 is 5% sucrose, 5 mM $NaPO_4$, demetalated; formulation #2 is 5% sucrose, 5 mM $NaPO_4$, 150 mM NaCl; formulation #4 is 5% sucrose, 5 mM $NaPO_4$, 150 mM NaCl, demetalated; formulation #5 is 4% mannose, 1% sucrose, 5 mM $NaPO_4$; formulation #6 is 4% mannose, 1% sucrose, 5 mM $NaPO_4$, demetalated; formulation #7 is 10 mM $NaPO_4$, 150 mM NaCl, 0.5 mM EDTA and 2% ethanol at pH 8.0; formulation #8 is 20 mM Tris, 150 NaCl, 10 mM succinate, 2% ethanol at pH 8.2; and formulation #9 is 20 mM glycine, 150 mM NaCl, 10 mM succinate, 2% ethanol at pH 9.0. DNA stability is measured as % of initial supercoiled (SC) DNA remaining.

To determine the stability of lyophilized DNA vaccines and to determine the effects of demetalating the formulation buffer on the stability of lyophilized DNA, a stability study was performed on the lyophilized samples over 4 months at 50° C. Three formulations were tested, each in the demetalated and non-demetalated state. The DNA concentration prior to the lyophilization was 20 mcg/mL. The lyophilization conditions were the same as described in this Example section. After 4 months of incubation the samples were resuspended in sterile water and analyzed by agarose gel electrophoresis to determine the % SC, OC and linear DNA. The results, shown in FIG. 26, indicated that the stability of the best lyophilized formulation exceeded that of the liquid formulations. However, the predicted 4 month stability of the best liquid formulation exceeded that of lyophilized formulations 1, 5 and 6. The 4 month stability data for the liquid formulations were based on extrapolations of stability data from 3 months (formulations 8 & 9) or 6 weeks (formulation 7) at 50° C. and 20 mcg/mL DNA. The results also indicated that demetalation improved the stability of the lyophilized DNA in formulations 1 and 2, but had little effect on the % SC DNA in the other lyophilized formulations. These results suggest that lyophilization is an effective way to stabilize DNA vaccines and that demetalation of the formulation buffer improves the stability of lyophilized DNA in some formulations.

EXAMPLE 18

Effect of EDTA and Ethanol on the Depurination and β-Elimination rate Constants

The results of DNA stability studies disclosed herein suggest that in the absence of free radical scavengers and metal ion chelators free radical oxidation is the major mechanism of DNA degradation in storage. The data also supports the hypothesis that trace metal ions and dissolved oxygen in formulation buffers cause free radical oxidation of the DNA. Based on this hypothesis, the major mechanisms of DNA degradation in formulations where free radical oxidation is effectively controlled (by EDTA and ethanol) would be the processes of depurination and β-elimination, which occurs to DNA in aqueous solutions (Lindahl et al., 1972, *Biochemistry* 11: 3610-3618). If depurination and β-elimination are the predominant mechanisms of degradation for DNA in storage, then it is possible to accurately predict the % SC DNA over time, using the published values of the depurination and β-elimination rate constants and the activation energies ($E_a$) for these reactions. However, the results of several DNA stability studies involving DNA vaccine formulations containing ethanol and EDTA/EtOH have suggested that the DNA in these formulations is much more stable than one would predict, based on the published rate constants. The reason for the higher than expected DNA stability in formulations containing ethanol is likely to be due to the much lower levels of free radical oxidation. This hypothesis is consistent with known art disclosing ethanol as an effective scavenger of hydroxyl radicals. Therefore, to determine the inherent stability of DNA in aqueous solution a stability study was initiated with DNA at 100 mcg/mL in PBS containing 1% EtOH and 0.5 mM EDTA at pH 7.4. To further control free radical oxidation of the DNA, the solutions were placed in sealed glass ampules. The ampules were incubated at 40, 50, 60 and 80° C. After various periods of time ampules were removed from the incubator and the solutions assayed for % SC DNA, in the presence and absence of *E. coli* Exonuclease III, to determine the number of AP (apurinic) sites per plasmid and to determine the rate constants for depurination ($k_1$) and β-elimination ($k_2$). A description of the AP site assay and the method for determining the depurination ($k_1$) and β-elimination $k_2$) rate constants are recorded below.

Description of the AP Assay—The assay is based on the conversion of supercoiled plasmid DNA (containing AP sites) to the open-circle form, after treatment with Exonuclease III. Exonuclease III from *E. coli* has an associated AP-endonuclease activity that will cleave the DNA backbone at AP sites, leaving DNA that lacks AP sites fully supercoiled. Since supercoiled plasmid DNA having only a single AP site per plasmid is completely converted to open-circle DNA by Exo III, the assay is sensitive enough to detect the presence of AP sites when only 5 to 10% of the DNA molecules contain an AP site.

The assay is performed by incubating 100 ng of plasmid DNA with and without 0.25 units of Exo m for 30 minutes at 37° C., in a total volume of 35 mL. An aliquot of the DNA (18 ng) is then subjected to agarose gel electrophoresis and ethidium bromide staining. The negative of the gel photograph is then scanned and the results are compared to supercoiled, open-circle and linear standards that are applied to the same gel, to allow quantitation of each form of DNA. To determine the number of AP sites in a sample of DNA, we use the data for percent supercoiled DNA before and after treatment with Exo III. For example, if a sample of DNA was 90% supercoiled before treatment and 50% supercoiled after treatment, the calculation of the number of AP sites would be as follows. First, based on past work, we assume that the rate of depurination is independent of DNA sequence and that the introduction of AP sites follows a Poisson distribution. Then, the equation is used that describes the number of strand breaks in a population of DNA molecules (SB) as a function of the fraction of DNA that is supercoiled ($f_f$).

$$SB = -\ln f_f$$

For DNA that is 90% supercoiled, the number of strand breaks per plasmid, on average, is:
SB=−ln(0.90) or 0.105
For DNA that is 50% supercoiled:
SB=−ln(0.50) or 0.693
Therefore, the difference between 0.693 and 0.105 (0.588) is the number of strand breaks introduced by cleaving the DNA at the AP sites and is therefore equal to the number of AP sites in the DNA.

Method for determining the depurination ($k_1$) and β-elimination ($k_2$) rate constants—To determine the depurination ($k_1$) and β-elimination ($k_2$) rate constants it is first necessary to derive an equation to establish the mathematical relationship between these rate constants and some DNA stability parameter that is easily measured. In this case we have derived an equation that establishes the relationship between the number of strand breaks per plasmid (SB) and the number of AP sites per plasmid, with $k_1$ and $k_2$. Since we have already described the relationship between SB and the % SC DNA (above), we may then use DNA stability data (measuring % SC DNA over time) and the AP site assay to determine $k_1$ and $k_2$, in DNA vaccine formulations containing EDTA and ethanol.

In a population of molecules we can begin with the assumption that the number of strand breaks per plasmid (SB) at any point in time, is equal to the total number of AP sites produced up to that time (TAP) minus the number of AP sites remaining, per plasmid (AP). To simplify the calculations we will also assume that the starting DNA contains no AP sites or strand breaks at time zero. Then,

SB=TAP−AP

Since TAP=$k_1$(PB)t, where $k_1$ is the depurination rate constant, PB=number of purine bases and t=time. Then, SB=$k_1$(PB)t−AP However, AP must be expressed in terms of $k_1$, $k_2$ and PB. Therefore, the rate of change of AP is set to equal to the rate of production of AP sites, minus the rate of conversion to strand breaks. Then solve for AP by integration.

$$dAP/dt = k_1(PB) - k_2(AP)$$

$$dAP = k_1(PB)dt - k_2(AP)dt$$

$$\int dAP = \int k_1(PB)dt - \int k_2(AP)dt$$

Assuming that AP initial is zero, then;

$$\int k_2(AP)dt = k_2(AP)t$$

and; AP=$k_1$(PB)t−$k_2$(AP)t

Then, solving for AP;

AP=$k_1$(PB)t/1+$k_2$t

Now, substituting this form of AP into our equation for SB, an equation is obtained indicating the number strand breaks per plasmid at any time.

SB=$k_1$(PB)t−[$k_1$(PB)t/1+$k_2$t]

Or, SB may be expressed in terms of AP.

Since, $$\int k_2(AP)dt = k_2(AP)t, \text{ and } \int k_2(AP)dt = SB$$

Then, SB=$k_2$(AP)t.

Results of $k_1$ and $k_2$ Determinations—Using the above equations, determined $k_1$ and $k_2$ were determined for a DNA vaccine formulation containing EDTA and ethanol at 40, 50, 60 and 80° C. The results are shown in Table 16. Table 16 also shows a comparison of the measured $k_1$ and $k_2$ to the published $k_1$ and $k_2$ values at the same pH and temperature. At 50° C., $k_1$ in this formulation is nearly 7-fold less than the published value, determined at the same pH and temperature. The results clearly indicate that the values of $k_1$ and $k_2$ in this formulation are much smaller than the published rate constants (Lindahl et al., 1972, *Biochemistry* 11: 3610-3618). This conclusion suggests that if free radical oxidation of DNA is effectively controlled, that the DNA is more stable than one would predict, based on the published rate constants for depurination and β-elimination. Moreover, the results suggest that the published rate constants are erroneously high, due to uncontrolled free radical oxidation.

TABLE 16

Measurements of $k_1$ and $k_2$ Using Exonuclease III*.

| Temperature | m$k_1$ | p$k_1$/m$k_1$ | m$k_2$ | p$k_2$/m$k_2$ |
|---|---|---|---|---|
| 40 C. | 1.38E−11 | 5.1 | 3.97E−07 | 2 |
| 50 C. | 4.91E−11 | 6.8 | 1.44E−06 | 1.8 |
| 60 C. | 2.73E−10 | 5.3 | 4.67E−06 | 1.7 |
| 80 C. | 2.15E−09 | 9.8 | 3.83E−05 | 1.7 |

*m$k_1$/m$k_2$ refer to the measured values, p$k_1$/p$k_2$ refer to published values.

Figure 29:
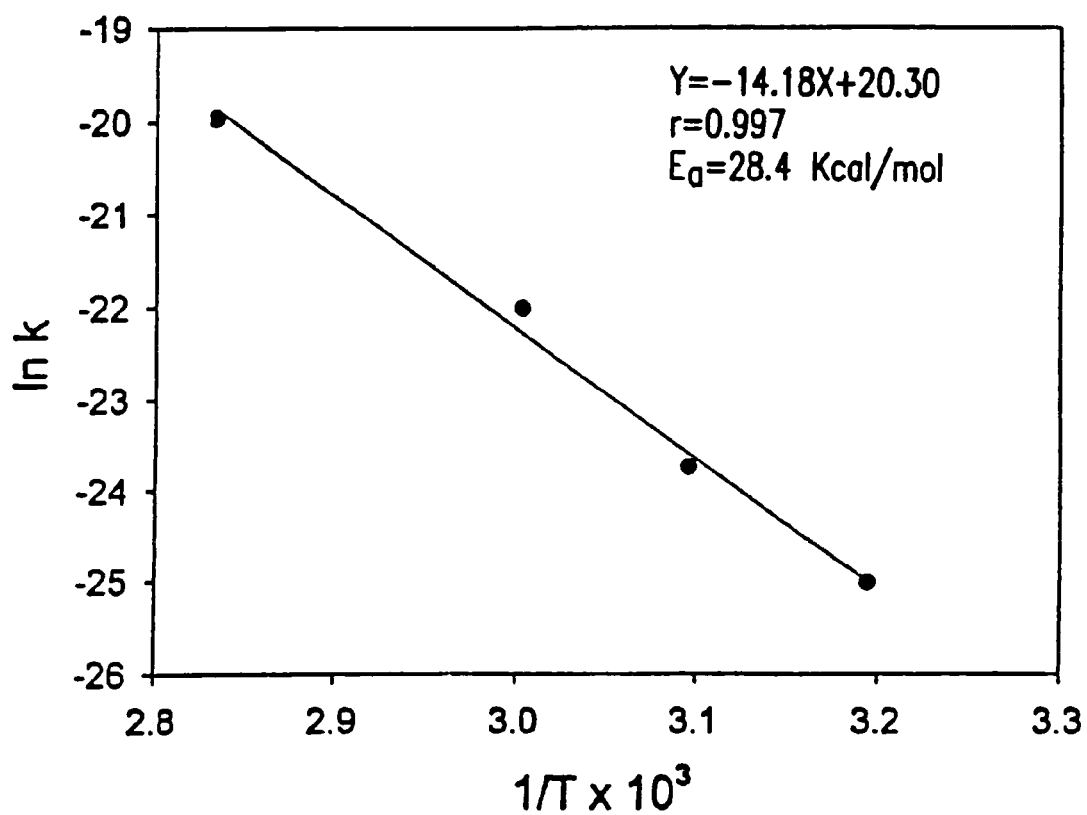
FIG. 29 shows an Arrhenius plot of depurination in PBS, 1% ethanol, and 0.5 mM EDTA at pH 7.4.
Figure 30:
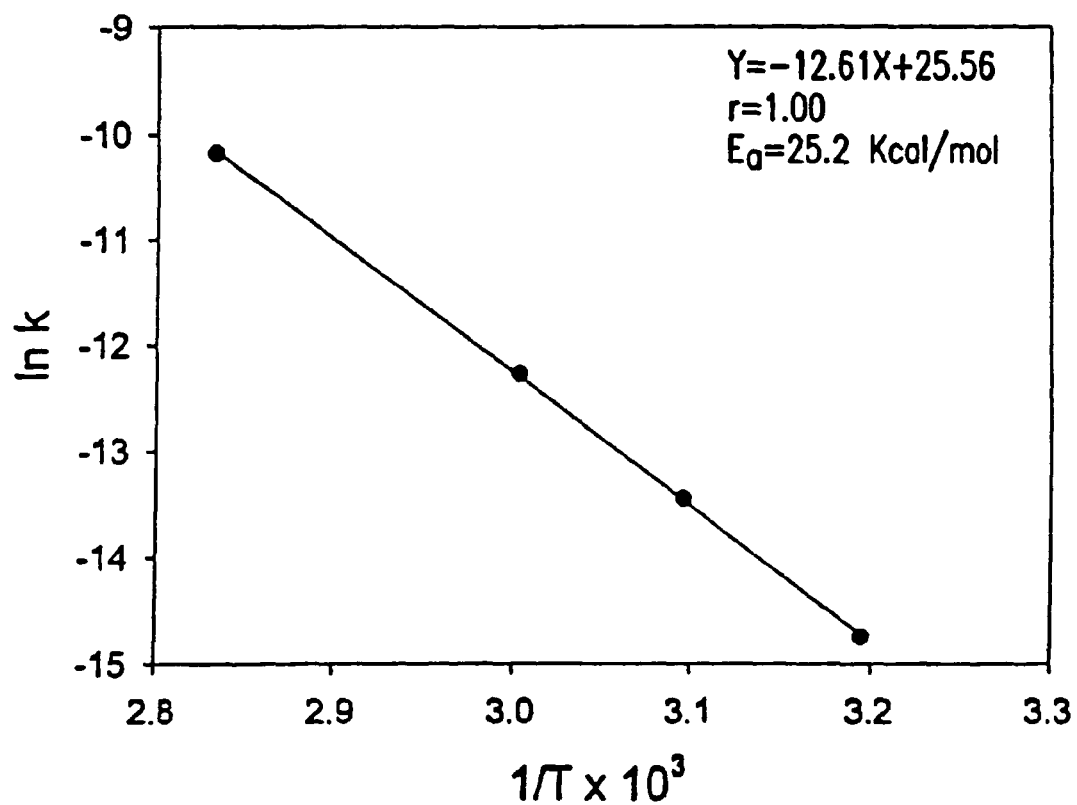
FIG. 30 shows an Arrhenius plot of β-elimination in PBS, 1% ethanol, and 0.5 mM EDTA at pH 7.4.

To determine the activation energies for depurination ($k_1$) and β-elimination ($k_2$) in the presence of EDTA/EtOH, and to determine if the mechanism of degradation of DNA in PBS containing EDTA/EtOH is predominately due to depurination and β-elimination, the above data were used to make Arrhenius plots. The results are shown in FIGS. 29 and 30. The results indicate that the activation energies for depurination and β-elimination are 28.4 and 25.2 kcal/mol, respectively. These values agree extremely well with the published values of 31±2 kcal/mol and 28 kcal/mol for depurination (Lindahl et al., 1972, *Biochemistry* 11: 3610-3618; Greer and Zamenhof, 1962, *J. Mol. Biol.* 4: 123), and 24.5 kcal/mol for β-elimination (Lindahl and Andersson, 1972, *Biochemistry* 11: 3618). These data suggest that the major mechanisms of DNA degradation in PBS containing EDTA/EtOH are depurination and β-elimination, and that the mechanism of these reactions is not altered by the presence of EDTA and ethanol. These data also allow prediction of the percent supercoiled DNA remaining for DNA stability studies performed at other temperatures (at pH 7.4), provided that the formulation effectively controls for free radical oxidation.

Figure 31:
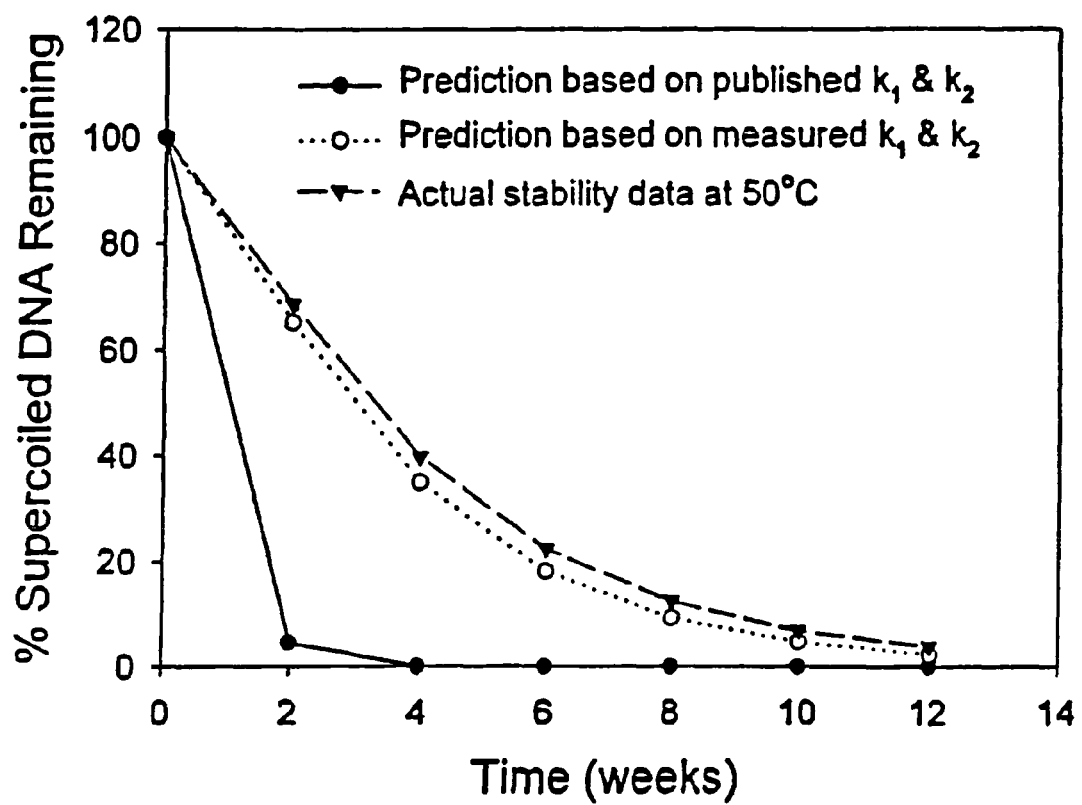
FIG. 31 shows a prediction of DNA stability at 50° C. using published and measured values of $k_1$ and $k_2$.

To show that the stability of DNA in a DNA vaccine formulation containing 100 mM EDTA and 1% ethanol (at pH 7.4) is much greater than predicted by the published rate constants, the DNA stability data is plotted below (FIG. 31), along with two stability predictions. The results clearly indicate that the DNA in this formulation is much more stable than the published rate constants would suggest. Moreover, the results indicate that the experimentally determined rate constants allow a much better prediction of DNA stability than does the use of the published rate constants.

Figure 32:
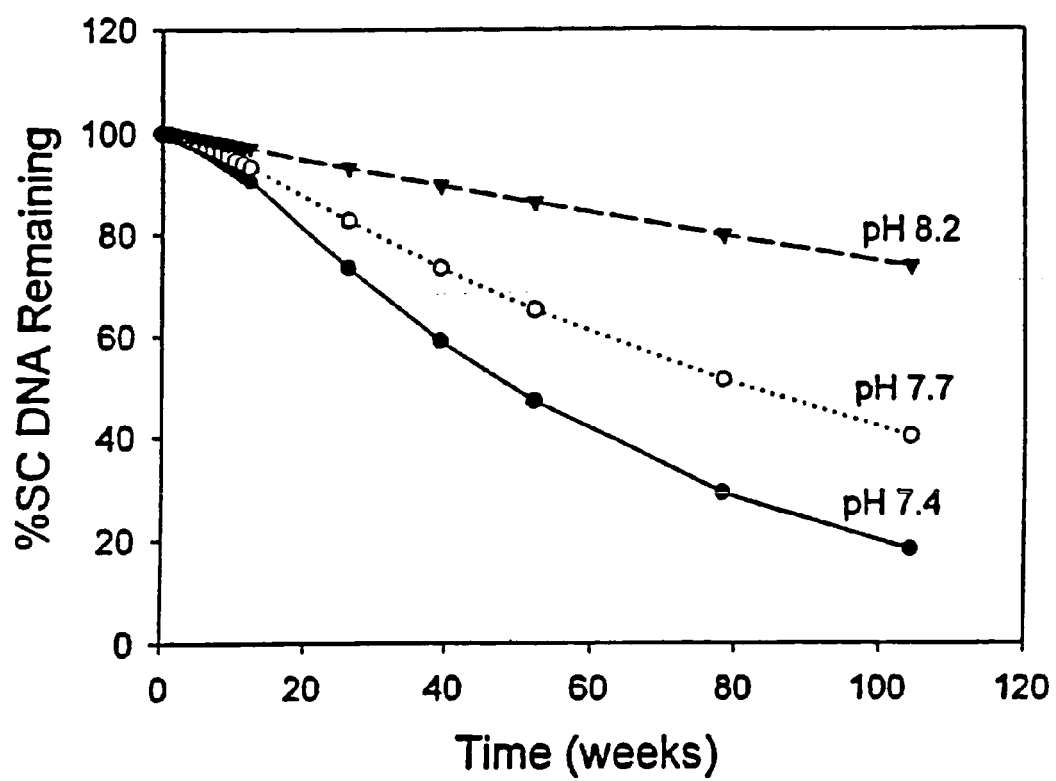
FIG. 32 shows a prediction of DNA stability at 30° C. based on measured values of $k_1$ and $k_2$ at pH 7.4.

Using the experimentally determined rate constants ($k_1$ and $k_2$) and the derived relationships between the rate constants and % SC DNA, it is possible to predict the formulation pH that would be required to achieve long-term stability at room temperature. These predictions (see FIG. 32) suggest that the pH of a DNA vaccine formulation (containing EDTA/EtOH) would need to be approximately 8.0, in order to maintain greater than 50% SC DNA for two years at 30° C., in a glass ampule.

These results show that EDTA/EtOH effectively controls free radical oxidation in DNA vaccine formulations, and thereby enhances DNA stability to levels that would not be expected, based on the use of the published rate constants for depurination and β-elimination.

What is claimed is:

1. A plasmid DNA formulation which comprises:
   a) purified plasmid DNA whereby metal ions have been optionally removed;
   b) EDTA present at a concentration from 1 μM to 5 mM;
   c) ethanol at a volume to volume concentration from 1% to 3%;
   d) a physiologically acceptable buffer selected from the group consisting of Tris-HCl, glycine, sodium phosphate, potassium phosphate, lithium phosphate, sodium succinate, potassium succinate, lithium succinate, sodium malate, potassium malate, lithium malate, sodium bicarbonate, potassium bicarbonate, lithium bicarbonate and combinations thereof; and,
   e) a salt selected from the group consisting of NaCl, KCl, LiCl and combinations thereof at a concentration up to 300 mM.

2. A plasmid DNA formulation which comprises:
   (a) purified plasmid DNA whereby metal ions have been optionally removed;
   (b) Tris-HCl buffer at a pH from about 8.0 to about 9.0;
   (c) ethanol present from 1% to 3% v/v;
   (d) EDTA present in a concentration range from 1 μM to 5 mM; and,
   (e) NaCl at a concentration from 50 mM to 500 mM.

3. A DNA plasmid formulation of claim 2 wherein the NaCl concentration is from 100 mM to 200 mM.

4. A DNA plasmid formulation of claim 2 wherein EDTA is present at a concentration from 1 μM to about 1 mM.

5. A DNA plasmid formulation of claim 2 wherein ethanol is present at a concentration from 1% to about 2.5%.

6. A DNA plasmid formulation of claim 1 wherein EDTA is present at a concentration from 1 μM to about 1 mM.

7. A DNA plasmid formulation of claim 1 wherein ethanol is present at a concentration from 1% to about 2.5%.

8. The DNA plasmid formulation of claim 1 wherein the salt concentration is from 100 mM to 200 mM.

9. The DNA plasmid formulation of claim 1 wherein the buffer is in the pH range from 8.0 to 9.5.

10. The DNA plasmid formulation of claim 1 wherein EDTA is present at about 500 μM.

11. The DNA plasmid formulation of claim 2 wherein EDTA is present at about 500 μM.

12. The DNA plasmid formulation of claim 1 wherein ethanol is present at 1%.

13. The DNA plasmid formulation of claim 2 wherein ethanol is present at 1%.

14. The DNA plasmid formulation of claim 1 wherein the buffer is selected from the group consisting of Tris-HCl at a pH from about 8.0 to about 9.0, glycine from about pH 9.0 to about 9.5, sodium phosphate at a pH from 7 to 8, potassium phosphate at a pH from 7 to 8, lithium phosphate at a pH from 7 to 8, sodium bicarbonate at a pH from 7 to 8, potassium bicarbonate at a pH from 7 to 8, and lithium bicarbonate at a pH from 7 to 8.

* * * * *